(12) United States Patent
Inglese et al.

(10) Patent No.: US 10,368,814 B2
(45) Date of Patent: Aug. 6, 2019

(54) METHOD FOR CEPHALOMETRIC ANALYSIS

(71) Applicant: Carestream Dental Technology Topco Limited, Rochester, NY (US)

(72) Inventors: Jean-Marc Inglese, Bussy-Saint-Georges (FR); Shoupu Chen, Rochester, NY (US); Jacques Faure, Tournefeuille (FR); Jacques Treil, Toulouse (FR)

(73) Assignee: Carestream Dental Technology Topco Limited, London (GB)

( * ) Notice: Subject to any disclaimer, the term of this patent is extended or adjusted under 35 U.S.C. 154(b) by 23 days.

(21) Appl. No.: 15/395,190

(22) Filed: Dec. 30, 2016

(65) Prior Publication Data

US 2018/0184989 A1    Jul. 5, 2018

(51) Int. Cl.
| | |
|---|---|
| *A61B 6/14* | (2006.01) |
| *A61B 6/02* | (2006.01) |
| *A61B 6/00* | (2006.01) |
| *A61C 7/00* | (2006.01) |
| *A61C 19/05* | (2006.01) |
| *G06T 7/00* | (2017.01) |

(52) U.S. Cl.
CPC ............. *A61B 6/14* (2013.01); *A61B 6/025* (2013.01); *A61B 6/463* (2013.01); *A61B 6/5217* (2013.01); *A61B 6/5235* (2013.01); *A61C 7/002* (2013.01); *A61C 19/05* (2013.01); *G06T 7/0012* (2013.01); *G06T 2207/10081* (2013.01); *G06T 2207/30036* (2013.01)

(58) Field of Classification Search
CPC combination set(s) only.
See application file for complete search history.

(56) References Cited

U.S. PATENT DOCUMENTS

| | | | |
|---|---|---|---|
| 6,250,918 B1 | 6/2001 | Sachdeva et al. | |
| 6,879,712 B2 | 4/2005 | Tuncay et al. | |
| 8,805,048 B2 | 8/2014 | Batesole | |
| 9,549,794 B2* | 1/2017 | Kopelman | ............... G06F 17/50 |
| 9,922,170 B2* | 3/2018 | Trosien | .................. G06Q 10/10 |

(Continued)

OTHER PUBLICATIONS

Vandana Kumar et al., "In Vivo Comparison of Conventional and Cone beam CT Synthesized Cephalograms," Angle Orthodontics, Sep. 2008, 78(5), pp. 873-879.

(Continued)

*Primary Examiner* — Tsung Yin Tsai

(57) ABSTRACT

A method for 3-D cephalometric analysis of a patient, executed at least in part on a computer processor, displays reconstructed volume image data from a computed tomographic scan of a patient's head from at least a first 2-D view and accepts an operator instruction that positions and displays at least one reference mark on the at least the first displayed 2-D view. One or more dentition elements within the mouth of the patient are segmented and cephalometric parameters for the patient computed and displayed according to data from the at least one reference mark and the one or more segmented dentition elements. Using the computed cephalometric parameters, one or more results indicative of maxillofacial asymmetry are computed and a graphical or text display energized to show the computed results indicative of asymmetry.

11 Claims, 47 Drawing Sheets

(56) References Cited

U.S. PATENT DOCUMENTS

| | | | |
|---|---|---|---|
| 9,943,382 B2* | 4/2018 | Wen | A61C 7/002 |
| 2007/0003907 A1* | 1/2007 | Chishti | A61C 7/00 |
| | | | 433/217.1 |
| 2009/0311647 A1* | 12/2009 | Fang | A61C 19/045 |
| | | | 433/24 |
| 2011/0244415 A1* | 10/2011 | Batesole | A61C 7/00 |
| | | | 433/24 |
| 2012/0041440 A1* | 2/2012 | Tong | A61F 5/566 |
| | | | 606/60 |
| 2012/0282573 A1* | 11/2012 | Mao | A61L 27/46 |
| | | | 433/202.1 |
| 2013/0022252 A1 | 1/2013 | Chen et al. | |
| 2013/0022254 A1 | 1/2013 | Chen | |
| 2013/0022255 A1 | 1/2013 | Chen et al. | |
| 2014/0348405 A1* | 11/2014 | Chen | G06T 7/60 |
| | | | 382/131 |

OTHER PUBLICATIONS

P. Planche and J. Treil, "Cephalometrics for the next millennium," The Future of Orthoontics, ed. Carine Carels, Guy Willems, Leuven University Press, 1998, pp. 182-192.

Cecil C. Steiner, "Cephalometrics in Clinical Practice," paper read at the Charles H. Tweed Foundation for Orthodontic Research, Oct. 1956, pp. 8-29.

J. Treil et al., "3D Tooth Modeling for Orthodontic Assessment," Seminars in Orthodontics, vol. 15, No. 1, Mar. 2009, pp. 42-47.

J. Treil et al., "The Human Face as a 3D Model for Cephalometric Analysis," World Journal of Orthodontics, World Journal of Orthodontics; 2005 Supplement, vol. 6 Issue 5, 6 pages.

International Search Report and Written Opinion dated Mar. 26, 2018 from International Application Serial No. PCT/GB2017/053885; 13 pages.

De Moraes, et al., "Evaluating Craniofacial Asymmetry with Digital Cephalometric Images and Cone-Beam Computed Tomography", American Journal of Orthodontics and Dentofacial Orthopedics, vol. 139, No. 6, dated Jan. 1, 2011, 10 pages.

Choi, Kang Young, "Analysis of Facial Asymmetry", Archives of Craniofacial Surgery, vol. 16, No. 1, dated Jan. 1, 2015, 10 pages.

Treil, Jacques, B. Waysenson, J. Braga and J. Casteigt, "The Human Face as a 3D Model for Cephalometric Analysis", Digital Radiography and Three-Dimensional Imaging, 32nd Annual Moyers Symposium, Feb. 26-27, 2005, Ann Arbor, MI, vol. 43, Craniofacial Growth Series, Department of Orthodontics and Pediatric Dentistry, School of Dentistry; and Center for Human Growth and Development, pp. 139-147.

\* cited by examiner

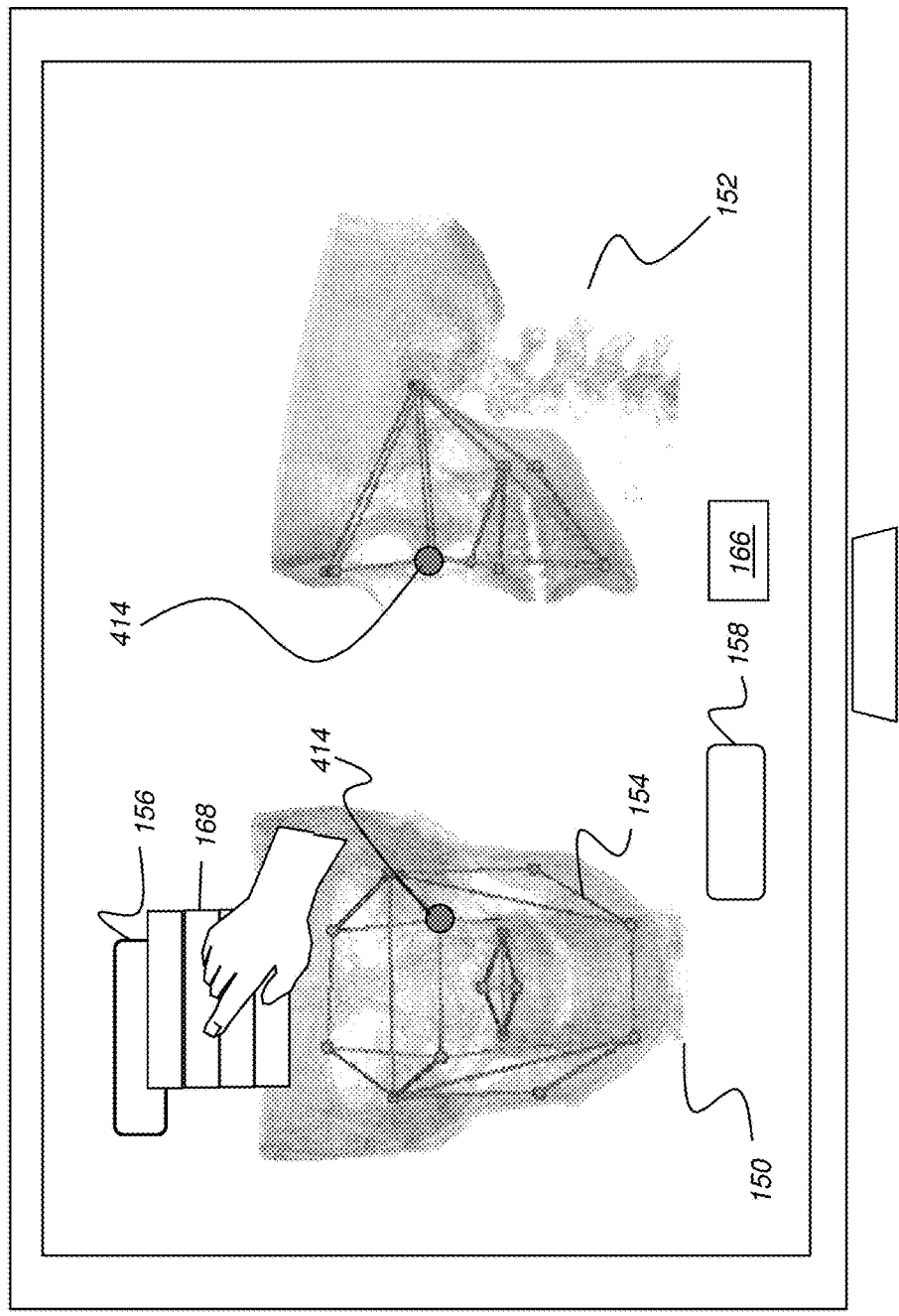

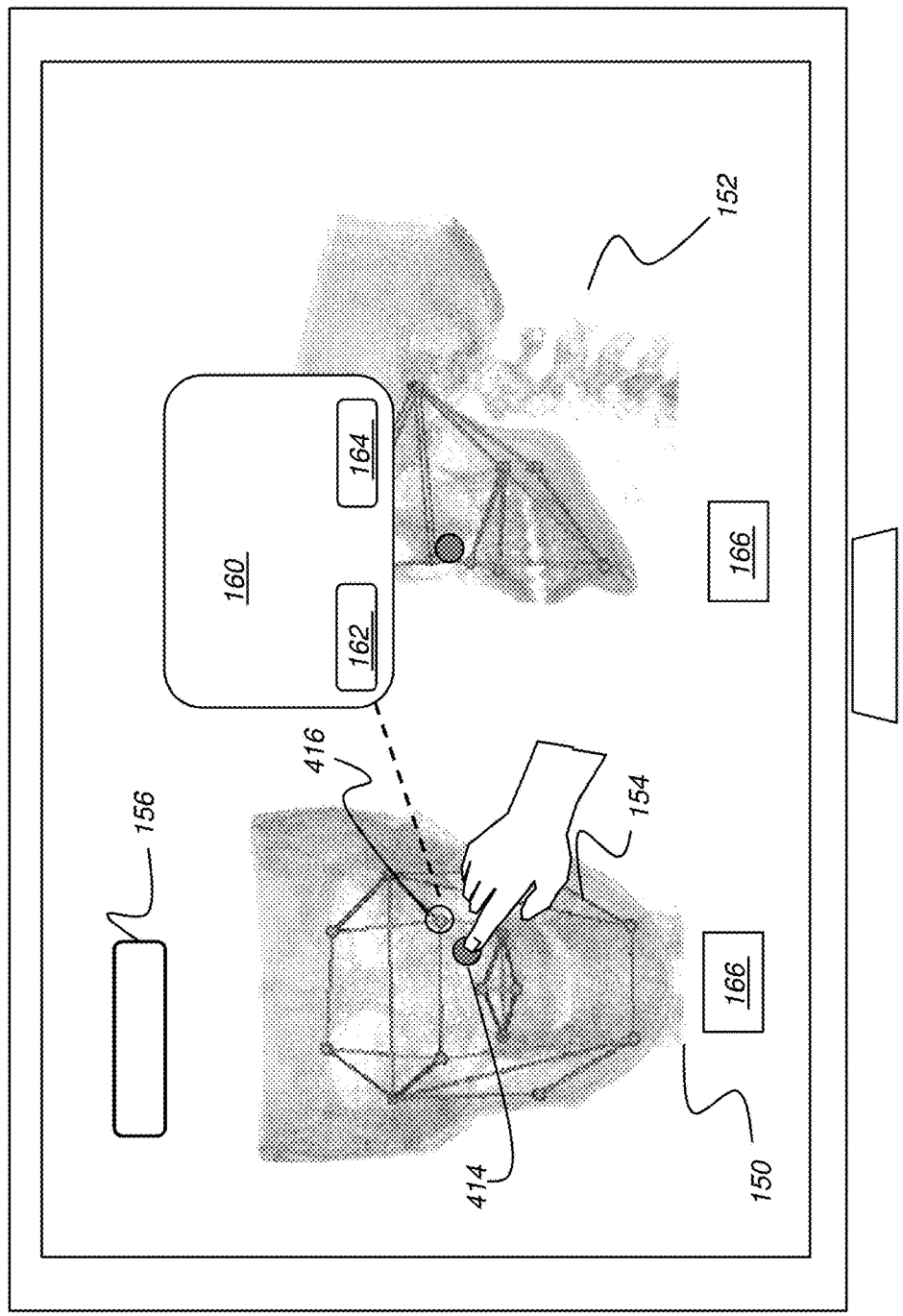

*independent_diagnosis_algorithm*

$x_m, y_m \in [normal\_parameters, abnormal\_parameters]$ $x_m \neq y_m; \quad m \in [1,2,\cdots,13]$

*given variables* $x_m, y_m$:
*define diagnosis_result_matrix(3x3)* $\mathbf{D}_m$
*evaluate vector* $\mathbf{c}_m := [-\infty < x_m \leq \mu_{x_m} - \sigma_{x_m}, \mu_{x_m} - \sigma_{x_m} < x_m < \mu_{x_m} + \sigma_{x_m}, \mu_{x_m} + \sigma_{x_m} \leq x_m < \infty]$
*evaluate vector* $\mathbf{r}_m := [-\infty < y_m \leq \mu_{y_m} - \sigma_{y_m}, \mu_{y_m} - \sigma_{y_m} < y_m < \mu_{y_m} + \sigma_{y_m}, \mu_{y_m} + \sigma_{y_m} \leq y_m < \infty]$
$\mu = Class\_1\_mean \quad ; \quad \sigma = Class\_1\_deviation$
$\mathbf{D}_m(i,j) = true \quad if \quad \mathbf{c}_m(j) = true \quad and \quad \mathbf{r}_m(i) = true;$
$i, j \in [1,2,3].$

FIG. 29

*dependent_diagnosis_algorithm*

$x_k, y_k \in [normal\_parameters, abnormal\_parameters]$ $x_k \neq y_k; k \in [m,n]; \quad m,n \in [1,2,\cdots,12,13]; m \neq n$

*given variables* $x_k, y_k$:
*define diagnosis_matrices(3x3)* $\mathbf{D}_m, \mathbf{D}_n$
*evaluate vector* $\mathbf{c}_k := [-\infty < x_k \leq \mu_{x_k} - \sigma_{x_k}, \mu_{x_k} - \sigma_{x_k} < x_k < \mu_{x_k} + \sigma_{x_k}, \mu_{x_k} + \sigma_{x_k} \leq x_k < \infty]$
*evaluate vector* $\mathbf{r}_k := [-\infty < y_k \leq \mu_{y_k} - \sigma_{y_k}, \mu_{y_k} - \sigma_{y_k} < y_k < \mu_{y_k} + \sigma_{y_k}, \mu_{y_k} + \sigma_{y_k} \leq y_k < \infty]$
$\mu = Class\_1\_mean \quad \sigma = Class\_1\_deviation$
$\mathbf{D}_m(i,j) = true \quad if \quad \mathbf{c}_m(j) = true \quad and \quad \mathbf{r}_m(i) = true;$
$\mathbf{D}_n(i,j) = true \quad if \quad \mathbf{c}_n(j) = true \quad and \quad \mathbf{r}_n(i) = true;$
$\mathbf{D}_m(i,j) = \mathbf{D}_m(i,j) + \mathbf{D}_n(i,j); \quad if \quad i+j \neq 4 (exemplary)$
$i, j \in [1,2,3]; k \in [m,n].$

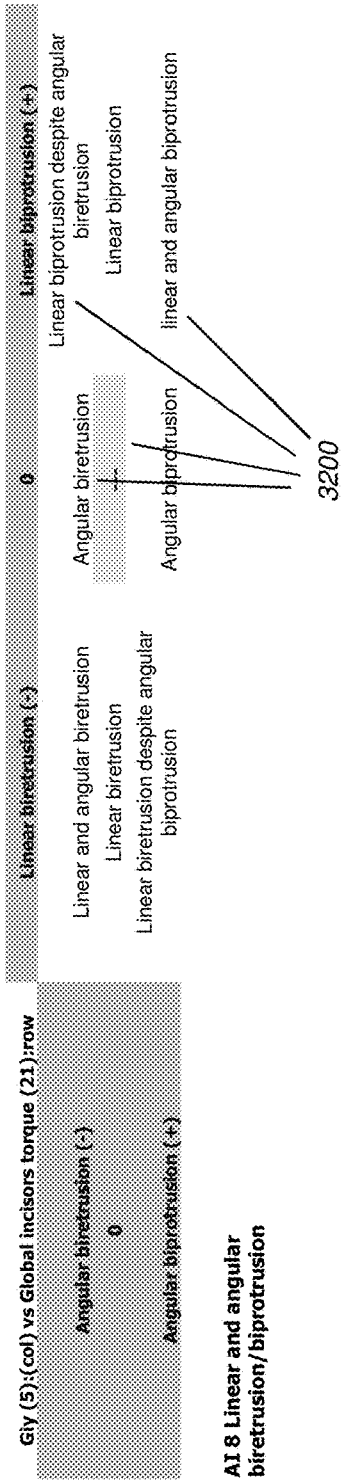

Case Name: 9500 9500 VOL 16

| AI | Parameters | Diagnosis |
|---|---|---|
| AI 1 Matching incisors and global arches antero-posterior upper/lower dyscrepancy | Incisors relation (1):col vs Arches angle relation (2):row | Underjet without Class III |
| AI 2 Matching incisors dyscrepancy and separate linear upper (and lower) incisors positions | Incisors relation (1):col vs Upper incisor position (19):row | Underjet by upper incisors retrusion |
| AI 3 Matching incisors dyscrepancy and separate linear (upper and) lower incisors positions | Incisors relation (1):col vs Lower incisor position (20):row | 0 |
| AI 4 Matching incisors gap & upper-lower CL II torque differential (CL III compensation) | Incisors relation (1):col vs Torque Upper/Lower difference (22):row | 0 |
| AI 5 Upper-lower separate responsibilities concerning upper-lower CL II torq. diff. (CL III compen.) | Upper incisors torque (3):(col) vs lower incisors torque (4):row | --- |
| AI 6 Matching alveolar and basic upper/lower relationship | Dental Class II (2):(col) vs basic Class II (6):row | Occlusal Class I despite basic Class III |
| AI 7 Upper/lower separate responsibilities concerning skeletal CL II and CL III | MNPy (23):(col) vs MMy (8):row | --- |
| AI 8 Linear and angular birebrusion/biprotrusion | Gly (5):(col) vs Global incisors torque (21):row | --- |
| AI 9 Global linear facial vertical height and its distribution | MMz (10):(col) vs Gdz/(MMz-Gdz) (26):row | Long face syndrom (linear) due to mandible excess |
| AI 10 Linear and angular facial dysharmony | MMz (10):(col) vs I3 (14):row | Basic hyperdivergence in agreement with facial hyperdivergence |
| AI 11 Alveolar and basi divergences | MxII-MdII (11):(col) vs FMA (12):row | --- |
| AI 12 Transverse linear and angular upper/lower alveolar relationship | dM-dm (15):(col) vs TqM-Tqm (16):row | --- |
| AI 13 Transverse linear and angular upper/lower basic relationship | RGP-LGP/RFM-LFM (17):(col) vs RIO-LIO/RM-LM (18):row | Maxilla basic excess and mental deficit |

*FIG. 32D*

T1; P19,17;C2,1; Upper/Lower incisors right deviation
T2; P20;C1,2; 0
T3; P8,7;C2,2; 0
T4; P1,17;C2,1; Upper/lower incisors right deviation
T5; P2,17;C2,1; 0
T6; P5,19;C2,2; 0
T7; P6,19;C2,2; 0
T8; P27,28;C2,1; 0
T9; P23,28;C2,1; 0
T10; P24,28;C3,1; Upper/Lower anterior landmarks right deviation is due to chin left deviation
T11; P28,17;C1,1; The upper/Lower incisors right deviation is in agreement with upper/lower base dev
T12; P3,1;C2,2; ---
T13; P4,2;C2,2; ---
T14; P8,7;C2,2; ---
T15; P15,14;C2,2; 0
T16; P2,1;C2,2; 0
T17; P6,5;C3,2; Left Class II
T18; P9,8;C2,2; ---
T19; P13,7;C3,3; Excess of the right hemiface and of the right horizontal branch S1 Anterior-posterior direction synthetic comment = strong right anteroposterior excess
S2 Vertical direction synthetic comment = none
S3 Transversal direction synthetic comment = left upper deviation (right excess) tendency

*FIG. 35*

METHOD FOR CEPHALOMETRIC ANALYSIS

FIELD OF THE INVENTION

The present invention relates generally to image processing in x-ray computed tomography and, in particular, to acquiring 3-D data for three dimensional cephalometric analysis.

BACKGROUND OF THE INVENTION

Cephalometric analysis is the study of the dental and skeletal relationships for the head and is used by dentists and orthodontists as an assessment and planning tool for improved treatment of a patient. Conventional cephalometric analysis identifies bony and soft tissue landmarks in 2-D cephalometric radiographs in order to diagnose facial features and abnormalities prior to treatment, or to evaluate the progress of treatment.

For example, a dominant abnormality that can be identified in cephalometric analysis is the anteroposterior problem of malocclusion, relating to the skeletal relationship between the maxilla and mandible. Malocclusion is classified based on the relative position of the maxillary first molar. For Class I, neutrocclusion, the molar relationship is normal but other teeth may have problems such as spacing, crowding, or over- or under-eruption. For Class II, distocclusion, the mesiobuccal cusp of the maxillary first molar rests between the first mandible molar and second premolar. For Class III, mesiocclusion, the mesiobuccal cusp of the maxillary first molar is posterior to the mesiobuccal grooves of the mandibular first molar.

An exemplary conventional 2-D cephalometric analysis method described by Steiner in an article entitled "Cephalometrics in Clinical Practice" (paper read at the Charles H. Tweed Foundation for Orthodontic Research, October 1956, pp. 8-29) assesses maxilla and mandible in relation to the cranial base using angular measures. In the procedure described, Steiner selects four landmarks: Nasion, Point A, Point B and Sella. The Nasion is the intersection of the frontal bone and two nasal bones of the skull. Point A is regarded as the anterior limit of the apical base of the maxilla. Point B is regarded as the anterior limit of the apical base of the mandible. The Sella is at the mid-point of the sella turcica. The angle SNA (from Sella to Nasion, then to Point A) is used to determine if the maxilla is positioned anteriorly or posteriorly to the cranial base; a reading of about 82 degrees is regarded as normal. The angle SNB (from Sella to Nasion then to Point B) is used to determine if the mandible is positioned anteriorly or posteriorly to the cranial base; a reading of about 80 degrees is regarded as normal.

Recent studies in orthodontics indicate that there are persistent inaccuracies and inconsistencies in results provided using conventional 2-D cephalometric analysis. One notable study is entitled "In vivo comparison of conventional and cone beam CT synthesized cephalograms" by Vandana Kumar et al. in *Angle Orthodontics*, September 2008, pp. 873-879.

Due to fundamental limitations in data acquisition, conventional 2-D cephalometric analysis is focused primarily on aesthetics, without the concern of balance and symmetry about the human face. As stated in an article entitled "The human face as a 3D model for cephalometric analysis" by Treil et al. in *World Journal of Orthodontics*, pp. 1-6, plane geometry is inappropriate for analyzing anatomical volumes and their growth; only a 3-D diagnosis is able to suitably analyze the anatomical maxillofacial complex. The normal relationship has two more significant aspects: balance and symmetry, when balance and symmetry of the model are stable, these characteristics define what is normal for each person.

U.S. Pat. No. 6,879,712, entitled "System and method of digitally modeling craniofacial features for the purposes of diagnosis and treatment predictions" to Tuncay et al., discloses a method of generating a computer model of craniofacial features. The three-dimensional facial features data are acquired using laser scanning and digital photographs; dental features are acquired by physically modeling the teeth. The models are laser scanned. Skeletal features are then obtained from radiographs. The data are combined into a single computer model that can be manipulated and viewed in three dimensions. The model also has the ability for animation between the current modeled craniofacial features and theoretical craniofacial features.

U.S. Pat. No. 6,250,918, entitled "Method and apparatus for simulating tooth movement for an orthodontic patient" to Sachdeva et al., discloses a method of determining a 3-D direct path of movement from a 3-D digital model of an actual orthodontic structure and a 3-D model of a desired orthodontic structure. This method simulates tooth movement based on each tooth's corresponding three-dimensional direct path using laser scanned crown and markers on the tooth surface for scaling. There is no true whole tooth 3-D data using the method described.

Although significant strides have been made toward developing techniques that automate entry of measurements and computation of biometric data for craniofacial features based on such measurements, there is considerable room for improvement. Even with the benefit of existing tools, the practitioner requires sufficient training in order to use the biometric data effectively. The sizable amount of measured and calculated data complicates the task of developing and maintaining a treatment plan and can increase the risks of human oversight and error.

Thus it can be seen that there would be particular value in development of analysis utilities that generate and report cephalometric results that can help to direct treatment planning and to track patient progress at different stages of ongoing treatment.

SUMMARY OF THE INVENTION

It is an object of the present disclosure to address the need for improved ways to acquire 3-D anatomical data for cephalometric analysis. With this object in mind, the present disclosure provides a method for 3-D cephalometric analysis, the method executed at least in part on a computer processor and comprising a method for 3-D cephalometric analysis of a patient, the method executed at least in part on a computer processor and comprising: displaying reconstructed volume image data from a computed tomographic scan of a patient's head from at least a first 2-D view; accepting an operator instruction that positions and displays at least one reference mark on the at least the first displayed 2-D view; segmenting one or more dentition elements within the mouth of the patient; computing and displaying a plurality of cephalometric parameters for the patient according to data from the at least one reference mark and the one or more segmented dentition elements; computing, using the computed cephalometric parameters, one or more results indicative of maxillofacial asymmetry; and energizing a graphical or text display to show the computed results indicative of maxillofacial asymmetry.

A feature of the present disclosure is interaction with an operator to identify the locations of reference marks indicative of anatomical features.

Embodiments of the present disclosure, in a synergistic manner, integrate skills of a human operator of the system with computer capabilities for feature identification. This takes advantage of human skills of creativity, use of heuristics, flexibility, and judgment, and combines these with computer advantages, such as speed of computation, capability for exhaustive and accurate processing, and reporting and data access capabilities.

These and other aspects, objects, features and advantages of the present disclosure will be more clearly understood and appreciated from a review of the following detailed description of the preferred embodiments and appended claims, and by reference to the accompanying drawings.

BRIEF DESCRIPTION OF THE DRAWINGS

The foregoing and other objects, features, and advantages of the invention will be apparent from the following more particular description of the embodiments of the disclosure, as illustrated in the accompanying drawings. The elements of the drawings are not necessarily to scale relative to each other.

FIGS. 9A, 9B, and 9C show an operator interface for specifying the location of anatomical features using operator-entered reference marks.

FIG. 20A is a perspective view that shows teeth of a digital phantom with tooth exclusion.

FIG. 20B is a graph showing computed axes of inertia systems for upper and lower jaws for the example of FIG. 20A.

FIG. 29 shows pseudo-code for an algorithm using the independent network arrangement of FIG. 27.

FIG. 30 shows pseudo-code for an algorithm using the dependent network arrangement of FIG. 28.

FIG. 31A lists example parameters as numerical values and their interpretation.

FIGS. 31B, 31C and 31D list, for a particular patient, example parameters as numerical values and their interpretation with respect to maxilofacial asymmetry, based on exemplary total maxillofacial asymmetry parameters according to exemplary embodiments of this application.

FIG. 32C shows exemplary tabulated results for another example with assessment of biretrusion or biprotrusion.

FIG. 32D shows an exemplary summary listing of results for cephalometric analysis of a particular patient.

FIG. 32E shows a detailed listing for one of the conditions listed in FIG. 35.

FIG. 35 shows an exemplary report for asymmetry according to an embodiment of the present disclosure.

DETAILED DESCRIPTION OF THE INVENTION

Figure 1:
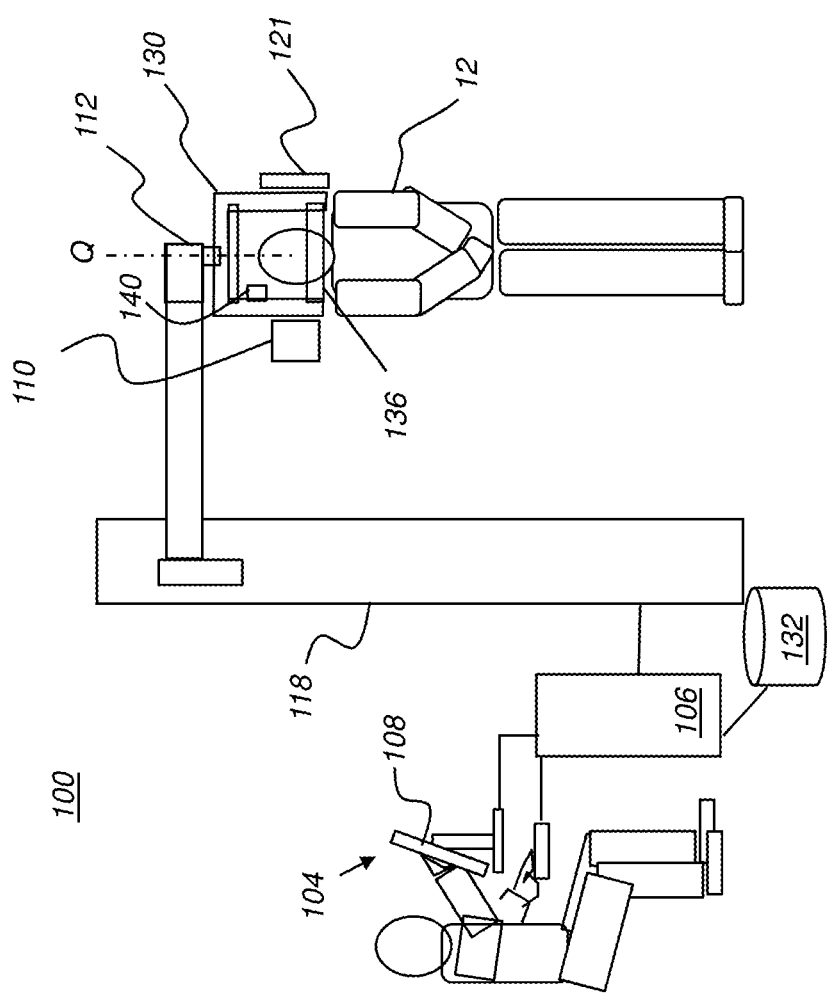
FIG. 1 is a schematic diagram showing an imaging system for providing cephalometric analysis.

In the following detailed description of embodiments of the present disclosure, reference is made to the drawings in which the same reference numerals are assigned to identical elements in successive figures. It should be noted that these figures are provided to illustrate overall functions and relationships according to embodiments of the present invention and are not provided with intent to represent actual size or scale.

Where they are used, the terms "first", "second", "third", and so on, do not necessarily denote any ordinal or priority relation, but may be used for more clearly distinguishing one element or time interval from another.

In the context of the present disclosure, the term "image" refers to multi-dimensional image data that is composed of discrete image elements. For 2-D images, the discrete image elements are picture elements, or pixels. For 3-D images, the discrete image elements are volume image elements, or voxels. The term "volume image" is considered to be synonymous with the term "3-D image".

In the context of the present disclosure, the term "code value" refers to the value that is associated with each 2-D image pixel or, correspondingly, each volume image data element or voxel in the reconstructed 3-D volume image. The code values for computed tomography (CT) or cone-beam computed tomography (CBCT) images are often, but not always, expressed in Hounsfield units that provide information on the attenuation coefficient of each voxel.

In the context of the present disclosure, the term "geometric primitive" relates to an open or closed shape such as a rectangle, circle, line, traced curve, or other traced pattern. The terms "landmark" and "anatomical feature" are considered to be equivalent and refer to specific features of patient anatomy as displayed.

In the context of the present disclosure, the terms "viewer", "operator", and "user" are considered to be equivalent and refer to the viewing practitioner or other person who views and manipulates an image, such as a dental image, on a display monitor. An "operator instruction" or "viewer instruction" is obtained from explicit commands entered by the viewer, such as using a computer mouse or touch screen or keyboard entry.

The term "highlighting" for a displayed feature has its conventional meaning as is understood to those skilled in the information and image display arts. In general, highlighting uses some form of localized display enhancement to attract the attention of the viewer. Highlighting a portion of an image, such as an individual organ, bone, or structure, or a path from one chamber to the next, for example, can be achieved in any of a number of ways, including, but not limited to, annotating, displaying a nearby or overlaying symbol, outlining or tracing, display in a different color or at a markedly different intensity or gray scale value than other image or information content, blinking or animation of a portion of a display, or display at higher sharpness or contrast.

In the context of the present disclosure, the descriptive term "derived parameters" relates to values calculated from processing of acquired or entered data values. Derived parameters may be a scalar, a point, a line, a volume, a vector, a plane, a curve, an angular value, an image, a closed contour, an area, a length, a matrix, a tensor, or a mathematical expression.

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members. For a set S, a subset may comprise the complete set S. A "proper subset" of set S, however, is strictly contained in set S and excludes at least one member of set S. Alternately, more formally stated, as the term is used in the present disclosure, a subset B can be considered to be a proper subset of set S if (i) subset B is non-empty and (ii) if B∩S is also non-empty and subset B further contains only elements that are in set S and has a cardinality that is less than that of set S.

In the context of the present disclosure, a "plan view" or "2-D view" is a 2-dimensional (2-D) representation or projection of a 3-dimensional (3-D) object from the position of a horizontal plane through the object. This term is synonymous with the term "image slice" that is conventionally used to describe displaying a 2-D planar representation from within 3-D volume image data from a particular perspective. 2-D views of the 3-D volume data are considered to be substantially orthogonal if the corresponding planes at which the views are taken are disposed at 90 (+/−10) degrees from each other, or at an integer multiple n of 90 degrees from each other (n*90 degrees, +/−10 degrees).

In the context of the present disclosure, the general term "dentition element" relates to teeth, prosthetic devices such as dentures and implants, and supporting structures for teeth and associated prosthetic device, including jaws.

The subject matter of the present disclosure relates to digital image processing and computer vision technologies, which is understood to mean technologies that digitally process data from a digital image to recognize and thereby assign useful meaning to human-understandable objects, attributes or conditions, and then to utilize the results obtained in further processing of the digital image.

As noted earlier in the background section, conventional 2-D cephalometric analysis has a number of significant drawbacks. It is difficult to center the patient's head in the cephalostat or other measuring device, making reproducibility unlikely. The two dimensional radiographs that are obtained produce overlapped head anatomy images rather than 3-D images. Locating landmarks on cephalograms can be difficult and results are often inconsistent (see the article entitled "Cephalometrics for the next millennium" by P. Planche and J. Treil in *The Future of Orthodontics*, ed. Carine Carels, Guy Willems, Leuven University Press, 1998, pp. 181-192). The job of developing and tracking a treatment plan is complex, in part, because of the significant amount of cephalometric data that is collected and calculated.

An embodiment of the present disclosure utilizes Treil's theory in terms of the selection of 3-D anatomic feature points, parameters derived from these feature points, and the way to use these derived parameters in cephalometric analysis. Reference publications authored by Treil include "The Human Face as a 3D Model for Cephalometric Analysis" Jacques Treil, B, Waysenson, J. Braga and J. Casteigt in *World Journal of Orthodontics*, 2005 Supplement, Vol. 6, issue 5, pp. 33-38; and "3D Tooth Modeling for Orthodontic Assessment" by J. Treil, J. Braga, J.-M. Loubes, E. Maza, J.-M. Inglese, J. Casteigt, and B. Waysenson in *Seminars in Orthodontics*, Vol. 15, No. 1, March 2009).

The schematic diagram of FIG. 1 shows an imaging apparatus 100 for 3-D CBCT cephalometric imaging. For imaging a patient 12, a succession of multiple 2-D projection images is obtained and processed using imaging apparatus 100. A rotatable mount 130 is provided on a column 118, preferably adjustable in height to suit the size of patient 12. Mount 130 maintains an x-ray source 110 and a radiation sensor 121 on opposite sides of the head of patient 12 and rotates to orbit source 110 and sensor 121 in a scan pattern about the head. Mount 130 rotates about an axis Q that corresponds to a central portion of the patient's head, so that components attached to mount 130 orbit the head. Sensor 121, a digital sensor, is coupled to mount 130, opposite x-ray source 110 that emits a radiation pattern suitable for CBCT volume imaging. An optional head support 136, such as a chin rest or bite element, provides stabilization of the patient's head during image acquisition. A computer 106 has an operator interface 104 and a display 108 for accepting operator commands and for display of volume images of the orthodontia image data obtained by imaging apparatus 100. Computer 106 is in signal communication with sensor 121 for obtaining image data and provides signals for control of source 110 and, optionally, for control of a rotational actuator 112 for mount 130 components. Computer 106 is also in signal communication with a memory 132 for storing image data. An optional alignment apparatus 140 is provided to assist in proper alignment of the patient's head for the imaging process.

Figure 2:
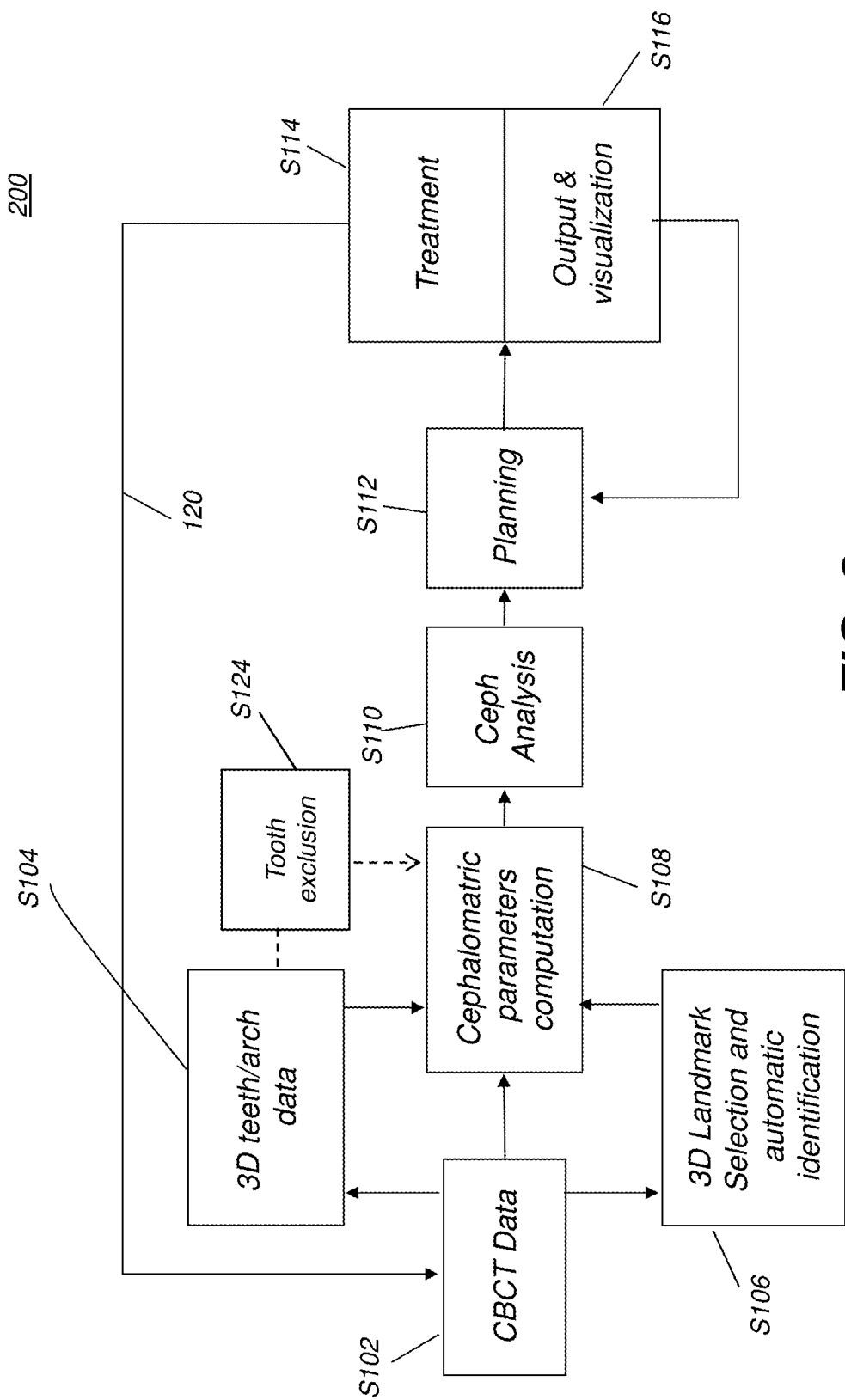
FIG. 2 is a logic flow diagram showing processes for 3-D cephalometric analysis according to an embodiment of the present disclosure.
Figure 3:
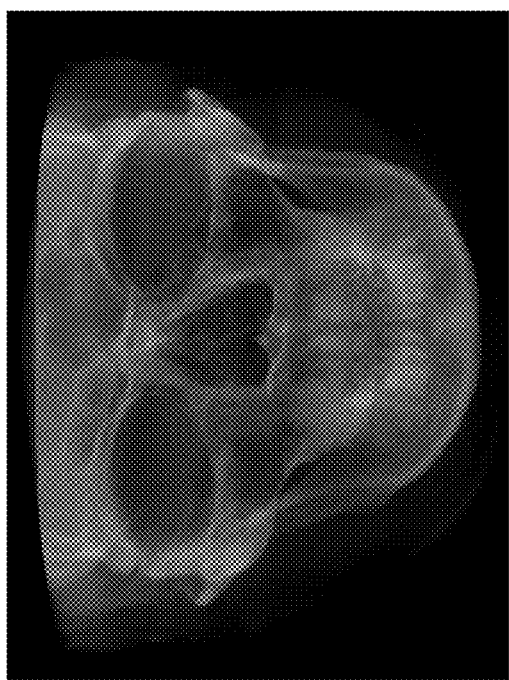
FIG. 3 is a view of 3-D rendered CBCT head volume images.

Referring to the logic flow diagram of FIG. 2, there is shown a sequence 200 of steps used for acquiring orthodontia data for 3-D cephalometric analysis with a dental CBCT volume according to an embodiment of the present disclosure. The CBCT volume image data is accessed in a data acquisition step S102. A volume contains image data for one or more 2-D images (or equivalently, slices). An original reconstructed CT volume is formed using standard reconstruction algorithms using multiple 2-D projections or sinograms obtained from a CT scanner. By way of example, FIG. 3 shows an exemplary dental CBCT volume 202 that contains bony anatomy, soft tissues, and teeth.

Continuing with the sequence of FIG. 2, in a segmentation step S104, 3-D dentition element data are collected by applying a 3-D tooth segmentation algorithm to the dental CBCT volume 202. Segmentation algorithms for teeth and related dentition elements are well known in the dental imaging arts. Exemplary tooth segmentation algorithms are described, for example, in commonly assigned U.S. Patent Application Publication No. 2013/0022252 entitled "PANORAMIC IMAGE GENERATION FROM CBCT DENTAL IMAGES" by Chen et al.; in U.S. Patent Application Publication No. 2013/0022255 entitled "METHOD AND SYSTEM FOR TOOTH SEGMENTATION IN DENTAL IMAGES" by Chen et al.; and in U.S. Patent Application Publication No. 2013/0022254 entitled "METHOD FOR TOOTH DISSECTION IN CBCT VOLUME" by Chen, incorporated herein by reference in its entirety.

Figure 4:
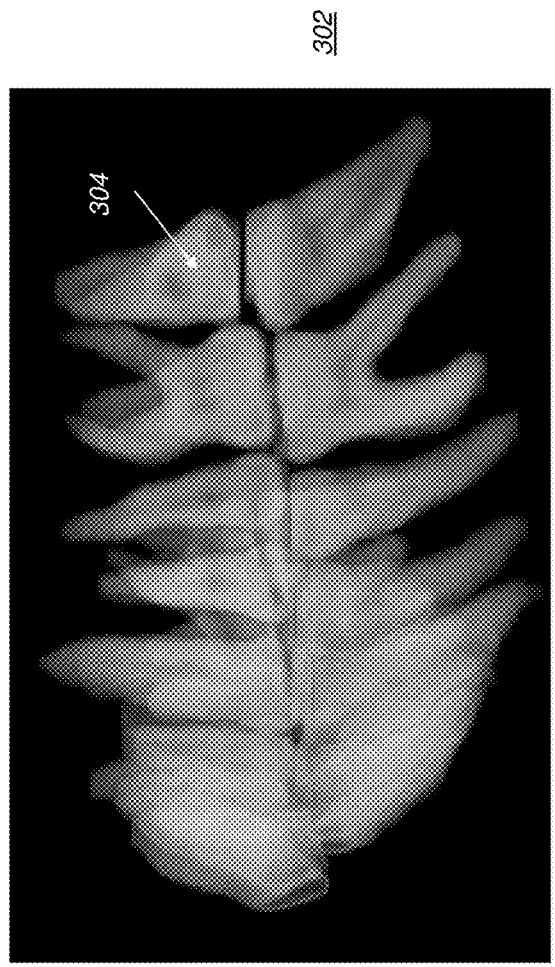
FIG. 4 is a view of a 3-D rendered teeth volume image after teeth segmentation.

As is shown in FIG. 4, tooth segmentation results are rendered with an image 302, wherein teeth are rendered as a whole but are segmented individually. Each tooth is a separate entity called a tooth volume, for example, tooth volume 304.

Each tooth of the segmented teeth or, more broadly, each dentition element that has been segmented has, at a minimum, a 3-D position list that contains 3-D position coordinates for each of the voxels within the segmented dentition element, and a code value list of each of the voxels within the segmented element. At this point, the 3-D position for each of the voxels is defined with respect to the CBCT volume coordinate system.

In a reference mark selection step S106 in the sequence of FIG. 2, the CBCT volume images display with two or more different 2-D views, obtained with respect to different view angles. The different 2-D views can be at different angles and may be different image slices, or may be orthographic or substantially orthographic projections, or may be perspective views, for example. According to an embodiment of the present disclosure, the three views are mutually orthogonal.

Figure 5:
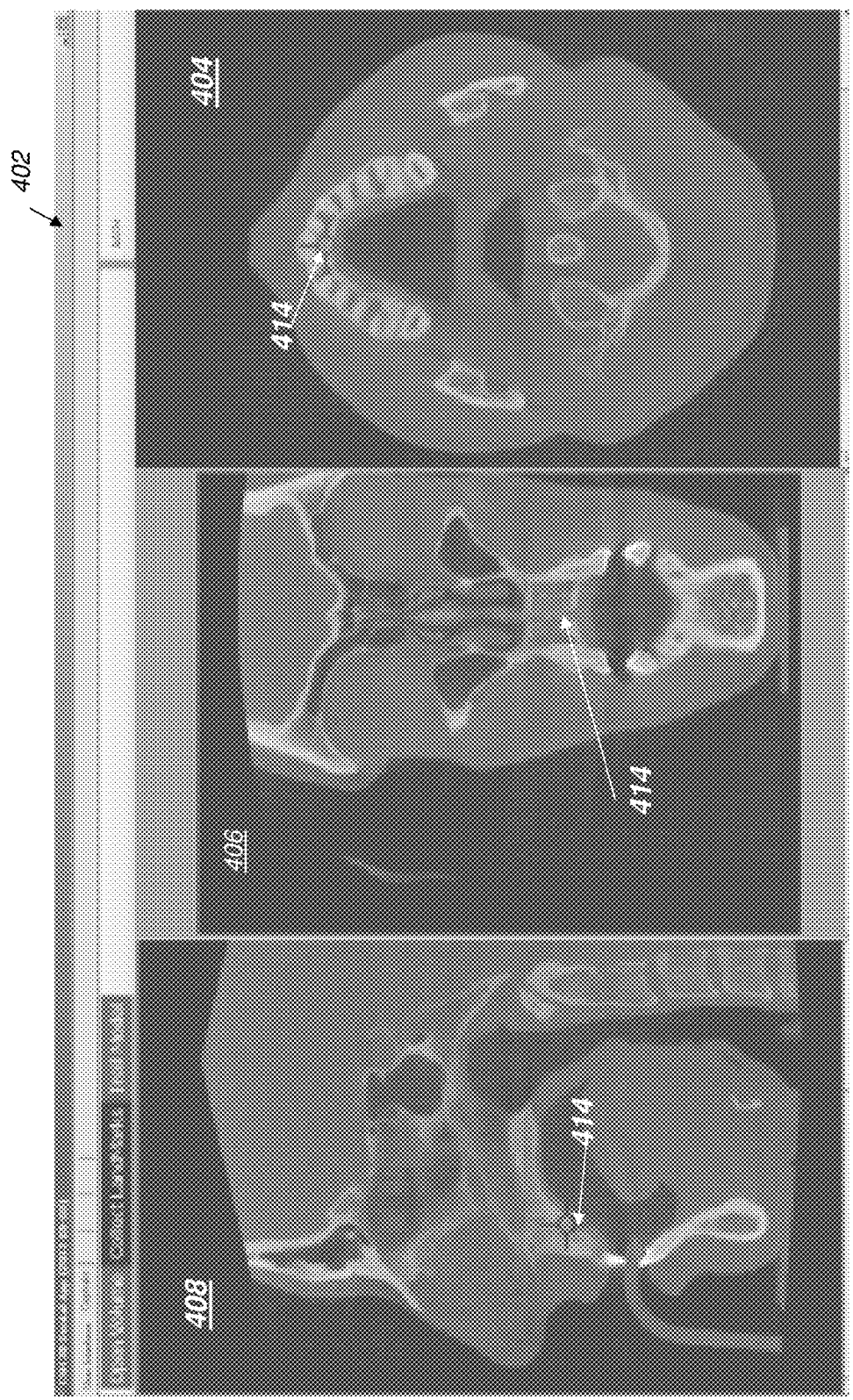
FIG. 5 is a view of a user interface that displays three orthogonal views of the CBCT head volume images and operator-entered reference marks.

FIG. 5 shows an exemplary format with a display interface 402 showing three orthogonal 2-D views. In display interface 402, an image 404 is one of the axial 2-D views of the CBCT volume image 202 (FIG. 3), an image 406 is one of the coronal 2-D views of the CBCT volume image 202, and an image 408 is one of the sagittal 2-D views of the CBCT volume image 202. The display interface allows a viewer, such as a practitioner or technician, to interact with the computer system that executes various image processing/computer algorithms in order to accomplish a plurality of 3-D cephalometric analysis tasks. Viewer interaction can take any of a number of forms known to those skilled in the user interface arts, such as using a pointer such as a computer mouse joystick or touchpad, or using a touch screen for selecting an action or specifying a coordinate of the image, for interaction described in more detail subsequently.

Figures 6, 7A:
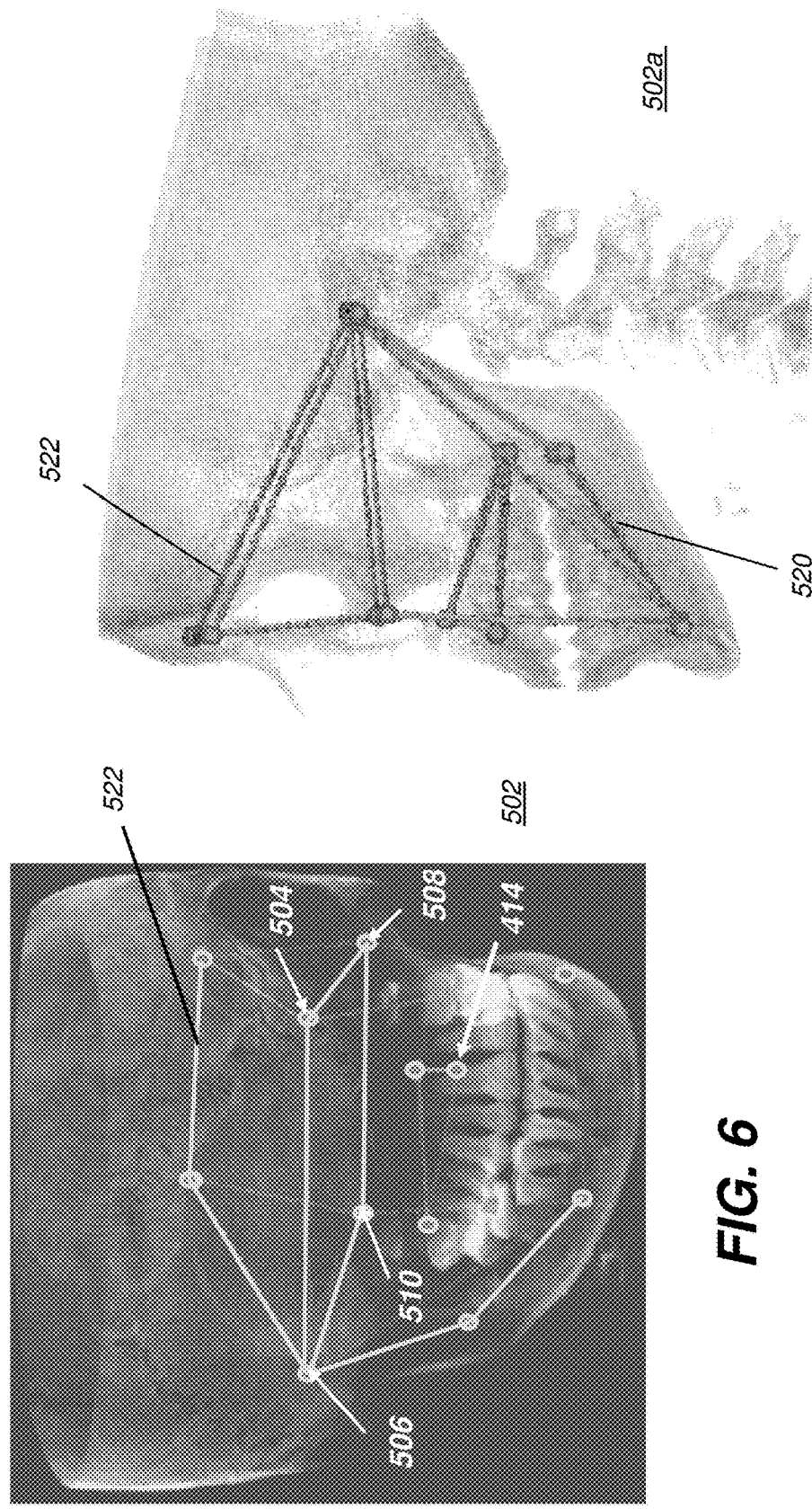
FIG. 6 is a view of 3-D rendered CBCT head volume images with a set of 3-D reference marks displayed.
FIGS. 7A, 7B, and 7C are perspective views that show identified anatomical features that provide a framework for cephalometric analysis.

One of the 3-D cephalometric analysis tasks is to perform automatic identification in 3-D reference mark selection step S106 of FIG. 2. The 3-D reference marks, equivalent to a type of 3-D landmark or feature point identified by the viewer on the displayed image, are shown in the different mutually orthogonal 2-D views of display interface 402 in FIG. 5. Exemplary 3-D anatomic reference marks shown in FIG. 5 are lower nasal palatine foramen at reference mark 414. As shown in the view of FIG. 6, other anatomic reference marks that can be indicated by the viewer on a displayed image 502 include infraorbital foramina at reference marks 508 and 510, and malleus at reference marks 504 and 506.

In step S106 of FIG. 2, the viewer uses a pointing device (such as a mouse or touch screen, for example) to place a reference mark as a type of geometric primitive at an appropriate position in any one of the three views. According to an embodiment of the present disclosure that is shown in figures herein, the reference mark displays as a circle. Using the display interface screen of FIG. 5, for example, the viewer places a small circle in the view shown as image 404 at location 414 as the reference mark for a reference point. Reference mark 414 displays as a small circle in image 404 as well as at the proper position in corresponding views in images 406 and 408. It is instructive to note that the viewer need only indicate the location of the reference mark 414 in one of the displayed views 404, 406 or 408; the system responds by showing the same reference mark 414 in other views of the patient anatomy. Thus, the viewer can identify the reference mark 414 in the view in which it is most readily visible.

After entering the reference mark 414, the user can use operator interface tools such as the keyboard or displayed icons in order to adjust the position of the reference mark 414 on any of the displayed views. The viewer also has the option to remove the entered reference mark and enter a new one.

The display interface 402 (FIG. 5) provides zoom in/out utilities for re-sizing any or all of the displayed views. The viewer can thus manipulate the different images efficiently for improved reference mark positioning.

The collection of reference marks made with reference to and appearing on views of the 3-D image content, provides a set of cephalometric parameters that can be used for a more precise characterization of the patient's head shape and structure. Cephalometric parameters include coordinate information that is provided directly by the reference mark entry for particular features of the patient's head. Cephalometric parameters also include information on various measurable characteristics of the anatomy of a patient's head that are not directly entered as coordinate or geometric structures but are derived from coordinate information, termed "derived cephalometric parameters". Derived cephalometric parameters can provide information on relative size or volume, symmetry, orientation, shape, movement paths and possible range of movement, axes of inertia, center of mass, and other data. In the context of the present disclosure, the term "cephalometric parameters" applies to those that are either directly identified, such as by the reference marks, or those derived cephalometric parameters that are computed according to the reference marks. For example, as particular reference points are identified by their corresponding reference marks, framework connecting lines 522 are constructed to join the reference points for a suitable characterization of overall features, as is more clearly shown in FIG. 6. Framework connecting lines 522 can be considered as vectors in 3-D space; their dimensional and spatial characteristics provide additional volume image data that can be used in computation for orthodontia and other purposes.

Figure 7C:
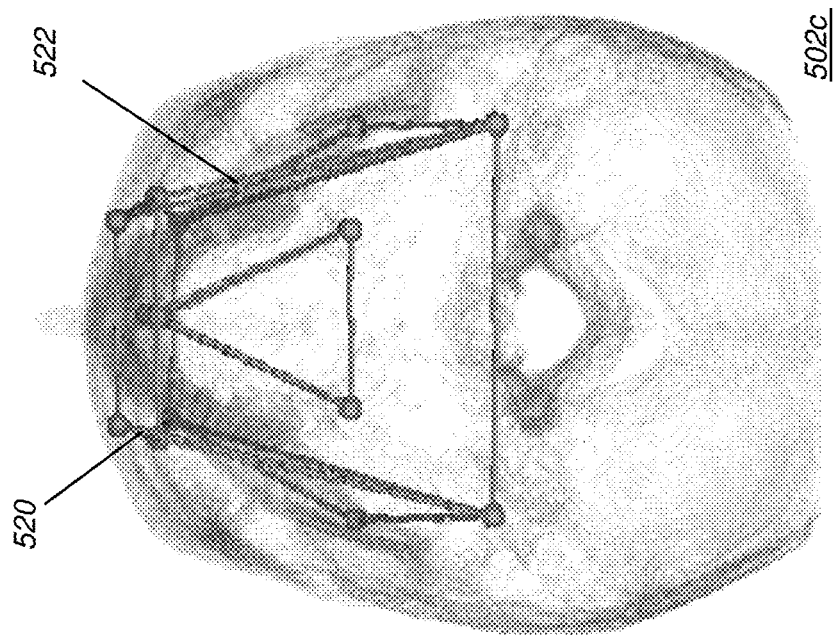
Figure 7B:
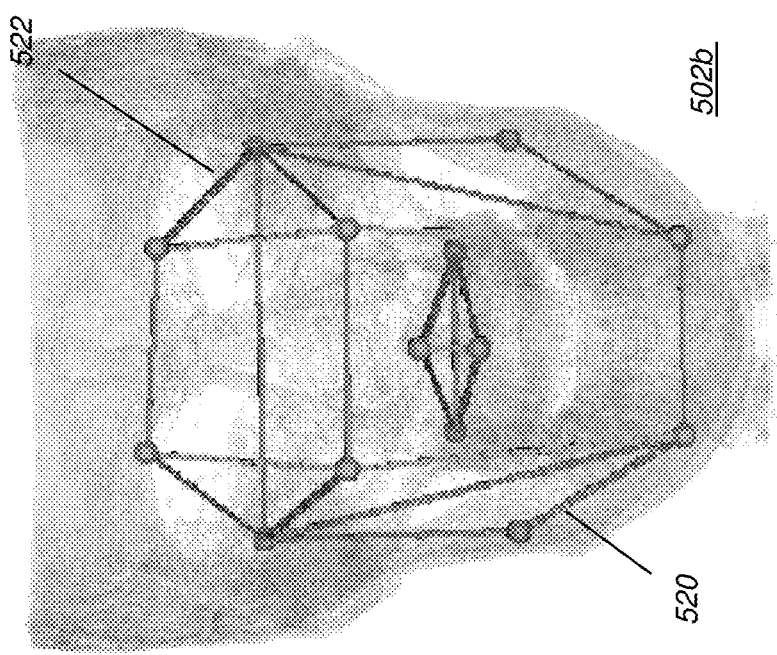

Each reference mark 414, 504, 506, 508, 510 is the terminal point for one or more framework connecting lines 522, generated automatically within the volume data by computer 106 of image processing apparatus 100 and forming a framework that facilitates subsequent analysis and measurement processing. FIGS. 7A, 7B, and 7C show, for displayed 3-D images 502a, 502b, and 502c from different perspective views, how a framework 520 of selected reference points, with the reference points at the vertices, helps to define dimensional aspects of the overall head structure. According to an embodiment of the present disclosure, an operator instruction allows the operator to toggle between 2-D views similar to those shown in FIG. 5 and the volume representation shown in FIG. 6, with partial transparency for voxels of the patient's head. This enables the operator to examine reference mark placement and connecting line placement from a number of angles; adjustment of reference mark position can be made on any of the displayed views. In addition, according to an embodiment of the present disclosure, the operator can type in more precise coordinates for a specific reference mark.

Figure 8:
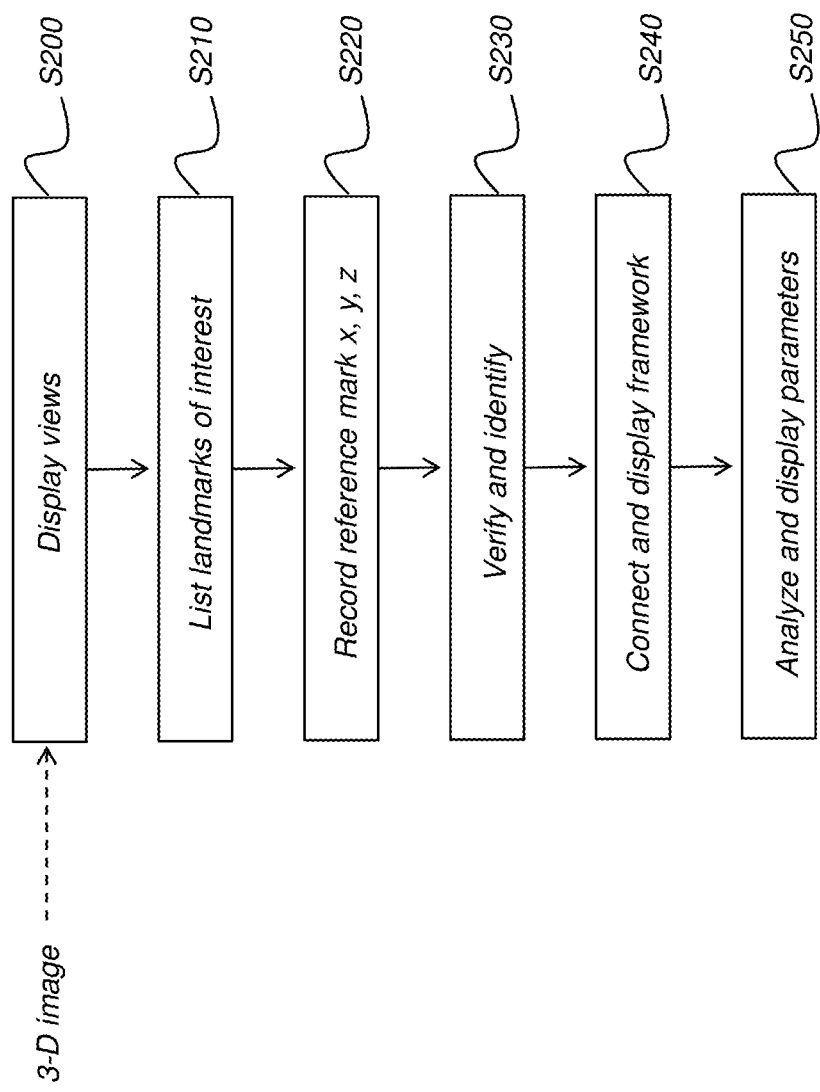
FIG. 8 is a logic flow diagram that shows steps for accepting operator instructions that generate the framework used for cephalometric analysis.

The logic flow diagram of FIG. 8 shows steps in a sequence for accepting and processing operator instructions for reference mark entry and identification and for providing computed parameters according to the image data and reference marks. A display step S200 displays one or more 2-D views, from different angles, such as from mutually orthogonal angles, for example, of reconstructed 3-D image data from a computed tomographic scan of a patient's head. In an optional listing step S210, the system provides a text listing such as a tabular list, a series of prompts, or a succession of labeled fields for numeric entry that requires entry of positional data for a number of landmarks or anatomical features in the reconstructed 3-D image. This listing may be explicitly provided for the operator in the form of user interface prompts or menu selection, as described subsequently. Alternately, the listing may be implicitly defined, so that the operator need not follow a specific sequence for entering positional information. Reference marks that give the x, y, z positional data for different anatomical features are entered in a recording step S220. Anatomical features can lie within or outside of the mouth of the patient. Embodiments of the present disclosure can use a combination of anatomical features identified on the display, as entered in step S220, and segmentation data automatically generated for teeth and other dentition elements, as noted previously with reference to FIG. 2.

In recording step S220 of FIG. 8, the system accepts operator instructions that position a reference mark corresponding to each landmark feature of the anatomy. The reference mark is entered by the operator on either the first or the second 2-D view, or on any of the other views if more than two views are presented and, following entry, displays on each of the displayed views. An identification step S230 identifies the anatomical feature or landmark that corresponds to the entered reference mark and, optionally, verifies the accuracy of the operator entry. Proportional values are calculated to determine the likelihood that a given operator entry accurately identifies the position of a reference mark for a particular anatomical feature. For example, the infraorbital foramen is typically within a certain distance range from the palatine foramen; the system checks the entered distance and notifies the operator if the corresponding reference mark does not appear to be properly positioned.

Continuing with the sequence of FIG. 8, in a construction step S240, framework connecting lines are generated to connect reference marks for frame generation. A computation and display step S250 is then executed, computing one or more cephalometric parameters according to the positioned reference marks. The computed parameters are then displayed to the operator.

Figure 9A:
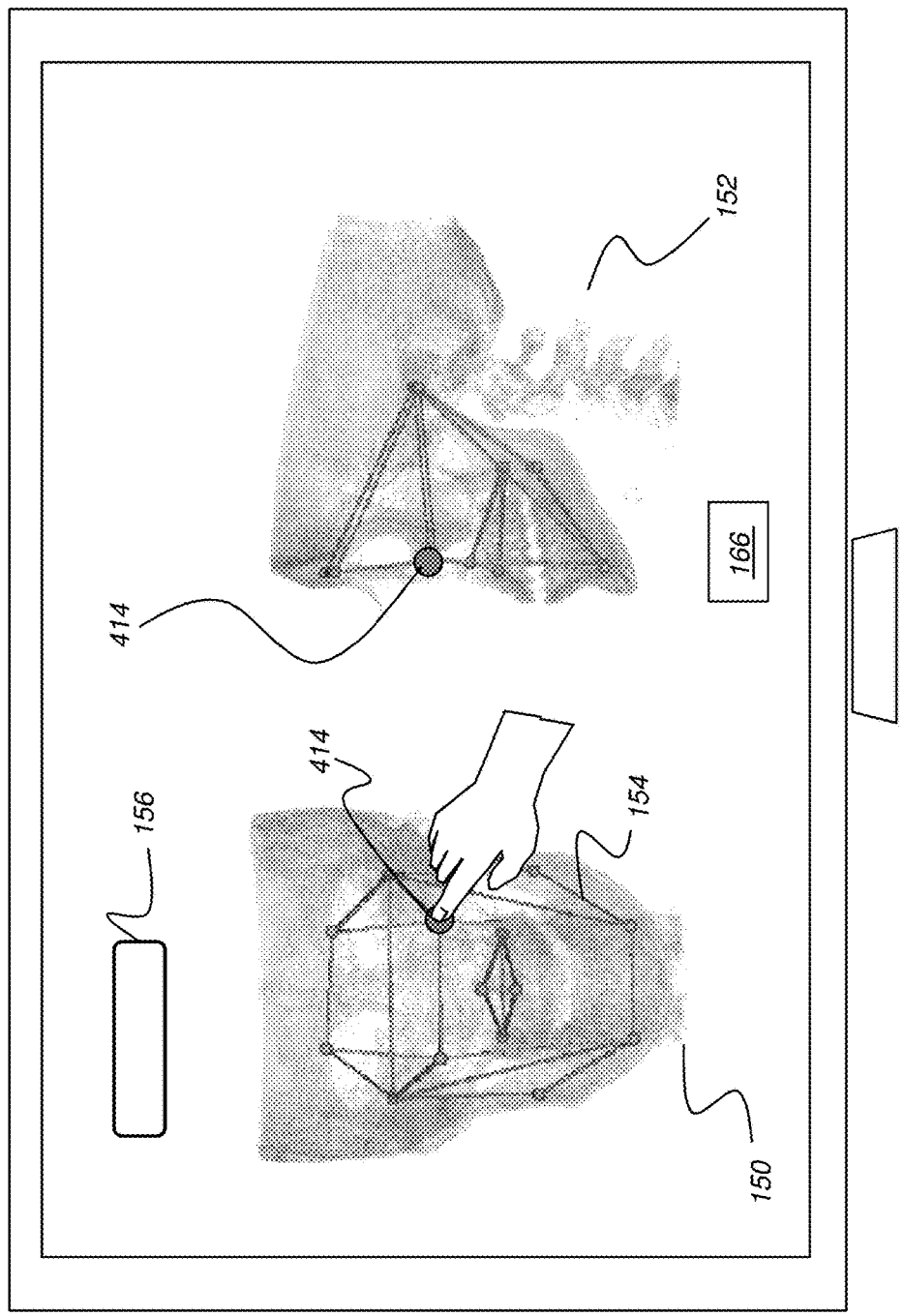

FIGS. 9A, 9B, and 9C show an operator interface appearing on display 108. The operator interface provides, on display 108, an interactive utility for accepting operator instructions and for displaying computation results for cephalometric parameters of a particular patient. Display 108 can be a touch screen display for entry of operator-specified reference marks and other instructions, for example. Display 108 simultaneously displays at least one 2-D view of the volume image data or two or more 2-D views of the volume image data from different angles or perspectives. By way of example, FIG. 9A shows a frontal or coronal view 150 paired with a side or sagittal view 152. More than two views can be shown simultaneously and different 2-D views can be shown, with each of the displayed views independently positioned according to an embodiment of the present disclosure. Views can be mutually orthogonal or may simply be from different angles. As part of the interface of display 108, an optional control 166 enables the viewer to adjust the perspective angle from which one or more of the 2-D views are obtained, either by toggling between alternate fixed views or by changing the relative perspective angle in increments along any of the 3-D axes (x, y, z). A corresponding control 166 can be provided with each 2-D view, as shown in FIG. 9-C. Using the operator interface shown for display 108, each reference mark 414 is entered by the operator using a pointer of some type, which may be a mouse or other electronic pointer or may be a touchscreen entry as shown in FIG. 9A. As part of the operator interface, an optional listing 156 is provided to either guide the operator to enter a specific reference mark according to a prompt, or to identify the operator entry, such as by selection from a drop-down menu 168 as shown in the example of FIG. 9B. Thus, the operator can enter a value in listing 156 or may enter a value in field 158, then select the name associated with the entered value from drop-down menu 168. FIGS. 9A-9C show a framework 154 constructed between reference points. As FIG. 9A shows, each entered reference mark 414 may be shown in both views 150 and 152. A selected reference mark 414 is highlighted on display 108, such as appearing in bold or in another color. A particular reference mark is selected in order to obtain or enter information about the reference mark or to perform some action, such as to shift its position, for example.

In the embodiment shown in FIG. 9B, the reference mark 414 just entered or selected by the operator is identified by selection from a listing 156. For the example shown, the operator selects the indicated reference mark 414, then makes a menu selection such as "infraorbital foramen" from menu 168. An optional field 158 identifies the highlighted reference mark 414. Calculations based on a model or based on standard known anatomical relationships can be used to identify reference mark 414, for example.

FIG. 9C shows an example in which the operator enters a reference mark 414 instruction that is detected by the system as incorrect or unlikely. An error prompt or error message 160 displays, indicating that the operator entry appears to be in error. The system computes a probable location for a particular landmark or anatomical feature based on a model or based on learned data, for example. When the operator entry appears to be inaccurate, message 160 displays, along with an optional alternate location 416. An override instruction 162 is displayed, along with a repositioning instruction 164 for repositioning the reference mark according to the calculated information from the system. Repositioning can be done by accepting another operator entry from the display screen or keyboard or by accepting the system-computed reference mark location, at alternate location 416 in the example of FIG. 9C.

According to an alternate embodiment of the present disclosure, the operator does not need to label reference marks as they are entered. Instead the display prompts the operator to indicate a specific landmark or anatomical feature on any of the displayed 2-D views and automatically labels the indicated feature. In this guided sequence, the operator responds to each system prompt by indicating the position of the corresponding reference mark for the specified landmark.

According to another alternate embodiment of the present disclosure, the system determines which landmark or anatomical feature has been identified as the operator indicates a reference mark; the operator does not need to label reference marks as they are entered. The system computes the most likely reference mark using known information about anatomical features that have already been identified and, alternately, by computation using the dimensions of the reconstructed 3-D image itself.

Using the operator interface shown in the examples of FIGS. 9A-9C, embodiments of the present disclosure provide a practical 3-D cephalometric analysis system that synergistically integrates the skills of the human operator of the system with the power of the computer in the process of 3-D cephalometric analysis. This takes advantage of human skills of creativity, use of heuristics, flexibility, and judgment, and combines these with computer advantages, such as speed of computation, capability for accurate and repeatable processing, reporting and data access and storage capabilities, and display flexibility.

Referring back to the sequence of FIG. 2, derived cephalometric parameters are computed in a computation step S108 once a sufficient set of landmarks is entered. FIGS. 10A through 10E show a processing sequence for computing and analyzing cephalometric data and shows how a number of cephalometric parameters are obtained from combined volume image data and anatomical features information according to operator entered instructions and according to segmentation of the dentition elements. According to an embodiment of the present disclosure, portions of the features shown in FIGS. 10A through 10E are displayed on display 108 (FIG. 1).

Figure 10A:
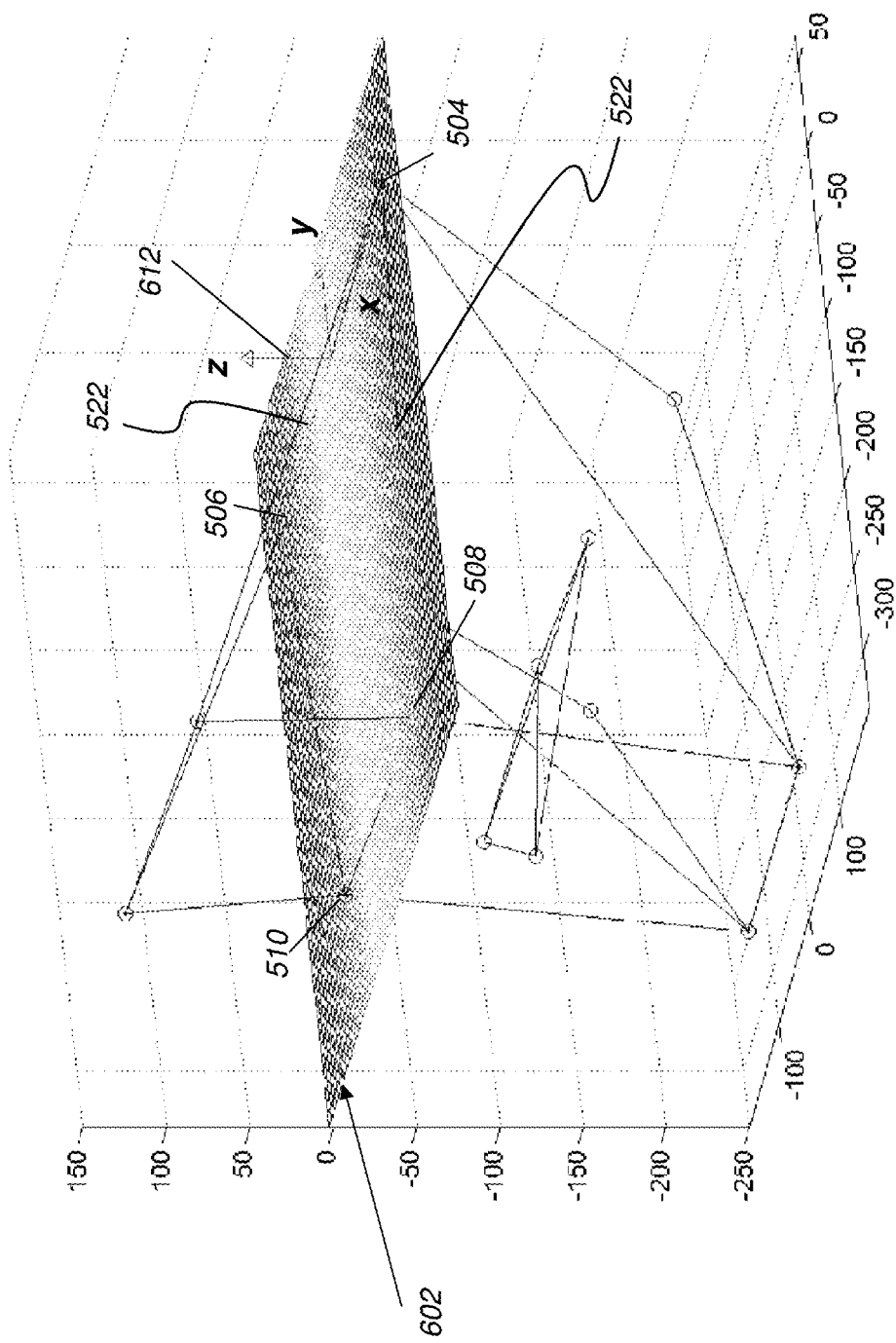
FIGS. 10A, 10B, 10C, 10D, and 10E are graphs that show how various derived parameters are calculated using the volume image data and corresponding operator-entered reference marks.

An exemplary derived cephalometric parameter shown in FIG. 10A is a 3-D plane 602 (termed a t-reference plane in cephalometric analysis) that is computed by using a subset of the set of first geometric primitives with reference marks 504, 506, 508 and 510 as previously described with reference to FIG. 6. A further derived cephalometric parameter is 3-D coordinate reference system 612 termed a t-reference system and described by Treil in publications noted previously. The z axis of the t-reference system 612 is chosen as perpendicular to the 3-D t-reference plane 602. The y axis of the t-reference system 612 is aligned with framework connecting line 522 between reference marks 508 and 504. The x axis of the t-reference system 612 is in plane 602 and is orthogonal to both z and x axes of the t-reference system. The directions of t-reference system axes are indicated in FIG. 10A and in subsequent FIGS. 10B, 10C, 10D, and 10E. The origin of the t-reference system is at the middle of framework connecting line 522 that connects reference marks 504 and 506.

With the establishment of t-reference system 612, 3-D reference marks from step S106 and 3-D teeth data (3-D position list of a tooth) from step S104 are transformed from the CBCT volume coordinate system to t-reference system 612. With this transformation, subsequent computations of derived cephalometric parameters and analyses can now be performed with respect to t-reference system 612.

Figure 10B:
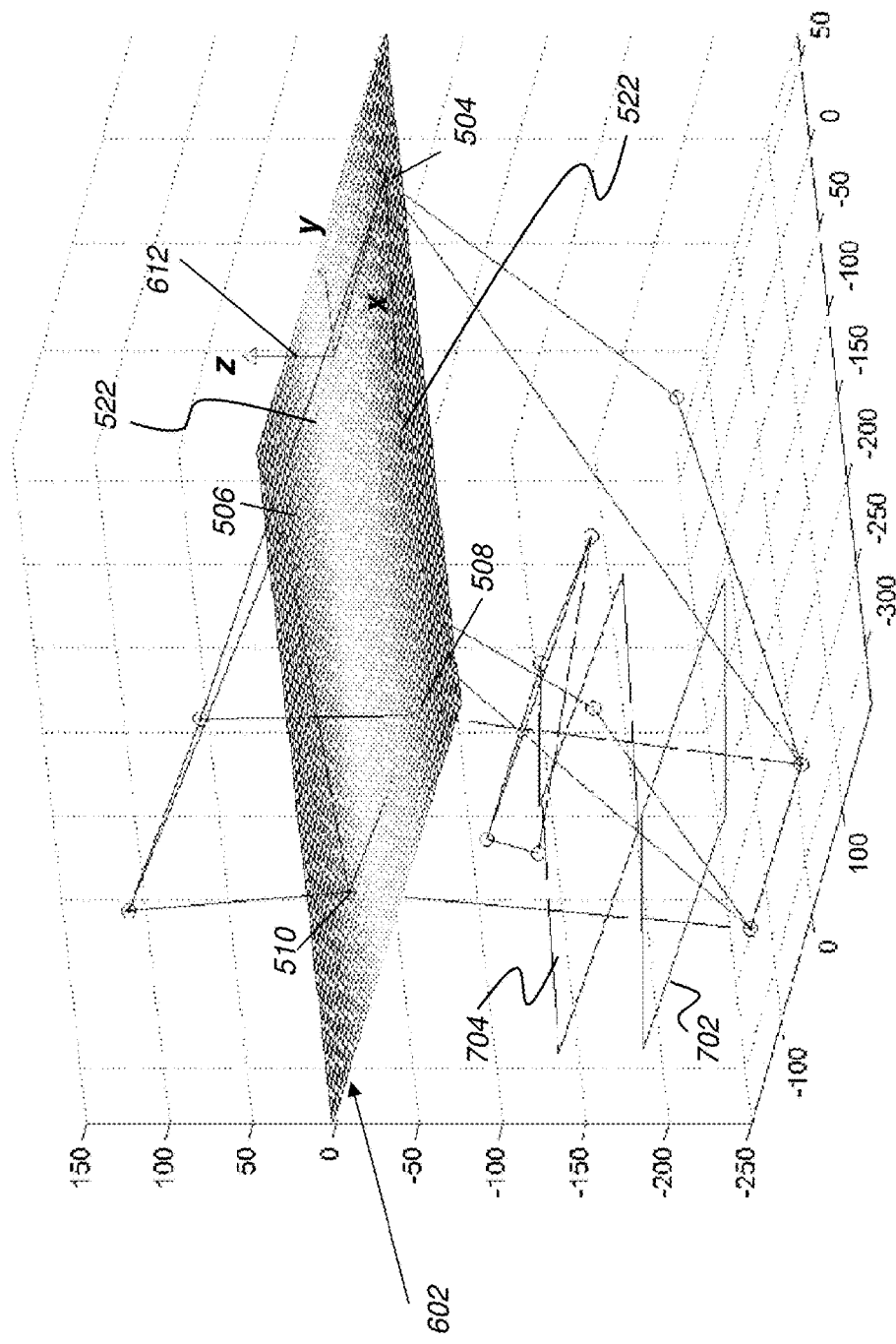

Referring to FIG. 10B, a 3-D upper jaw plane 704 and a 3-D lower jaw plane 702 can be derived from cephalometric parameters from the teeth data in t-reference system 612. The derived upper jaw plane 704 is computed according to teeth data segmented from the upper jaw (maxilla). Using methods familiar to those skilled in cephalometric measurement and analysis, derived lower jaw plane 702 is similarly computed according to the teeth data segmented from the lower jaw (mandibular).

For an exemplary computation of a 3-D plane from the teeth data, an inertia tensor is formed by using the 3-D position vectors and code values of voxels of all teeth in a jaw (as described in the cited publications by Treil); eigenvectors are then computed from the inertia tensor. These eigenvectors mathematically describe the orientation of the jaw in the t-reference system 612. A 3-D plane can be formed using two of the eigenvectors, or using one of the eigenvectors as the plane normal.

Figure 10C:
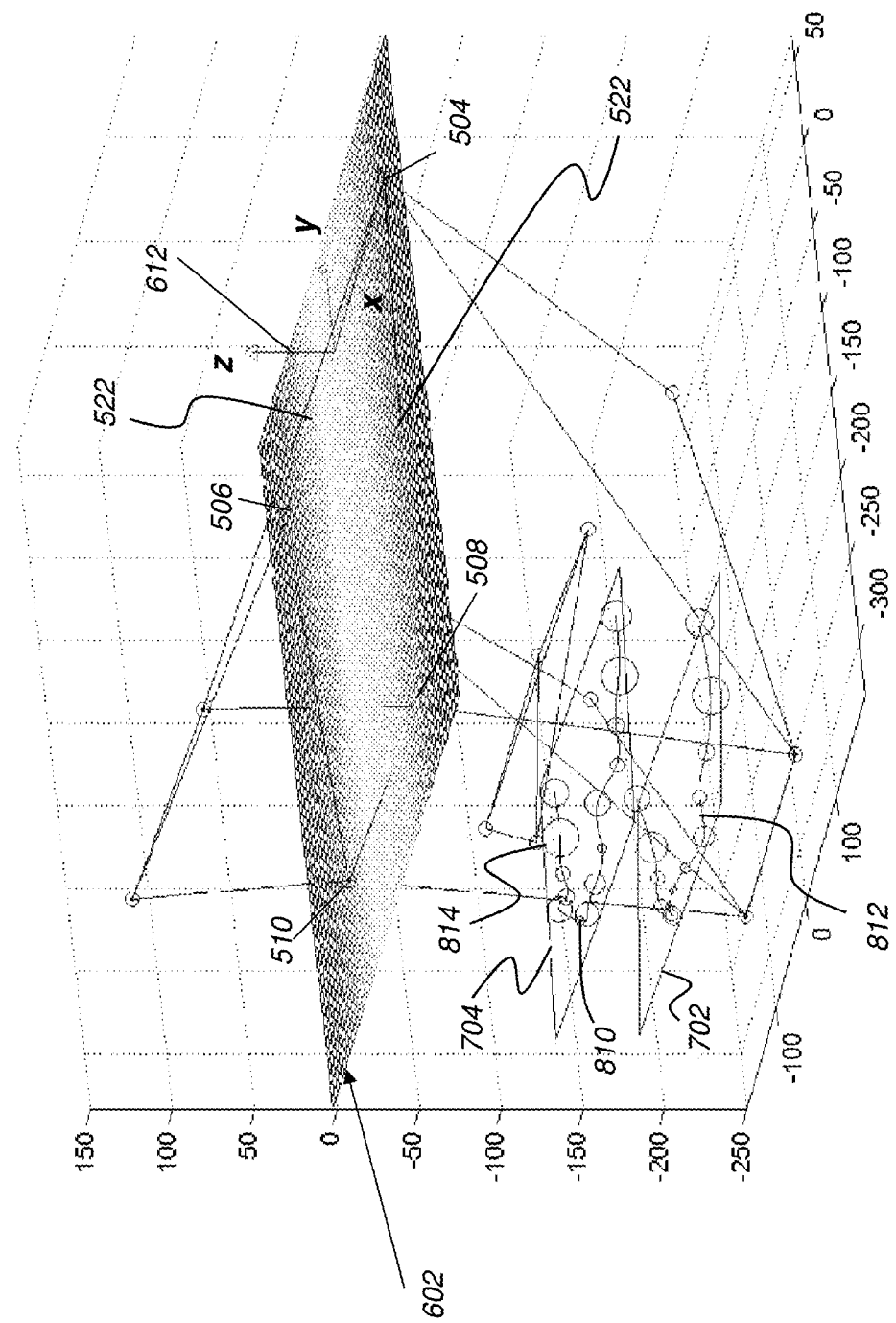

Referring to FIG. 10C, further derived parameters are shown. For each jaw, jaw curves are computed as derived parameters. An upper jaw curve 810 is computed for the upper jaw; a lower jaw curve 812 is derived for the lower jaw. The jaw curve is constructed to intersect with the mass center of each tooth in the respective jaw and to lie in the corresponding jaw plane. The mass center of the tooth can be calculated, in turn, using the 3-D position list and the code value list for the segmented teeth.

The mass of a tooth is also a derived cephalometric parameter computed from the code value list of a tooth. In FIG. 10C, an exemplary tooth mass is displayed as a circle 814 or other type of shape for an upper jaw tooth. According to an embodiment of the present disclosure, one or more of the relative dimensions of the shape, such as the circle radius, for example, indicates relative mass value, the mass value of the particular tooth in relation to the mass of other teeth in the jaw. For example, the first molar of the upper jaw has a mass value larger than the neighboring teeth mass values.

According to an embodiment of the present disclosure, for each tooth, an eigenvector system is also computed. An inertia tensor is initially formed by using the 3-D position vectors and code values of voxels of a tooth, as described in the cited publications by Treil. Eigenvectors are then computed as derived cephalometric parameters from the inertia tensor. These eigenvectors mathematically describe the orientation of a tooth in the t-reference system.

Figure 10D:
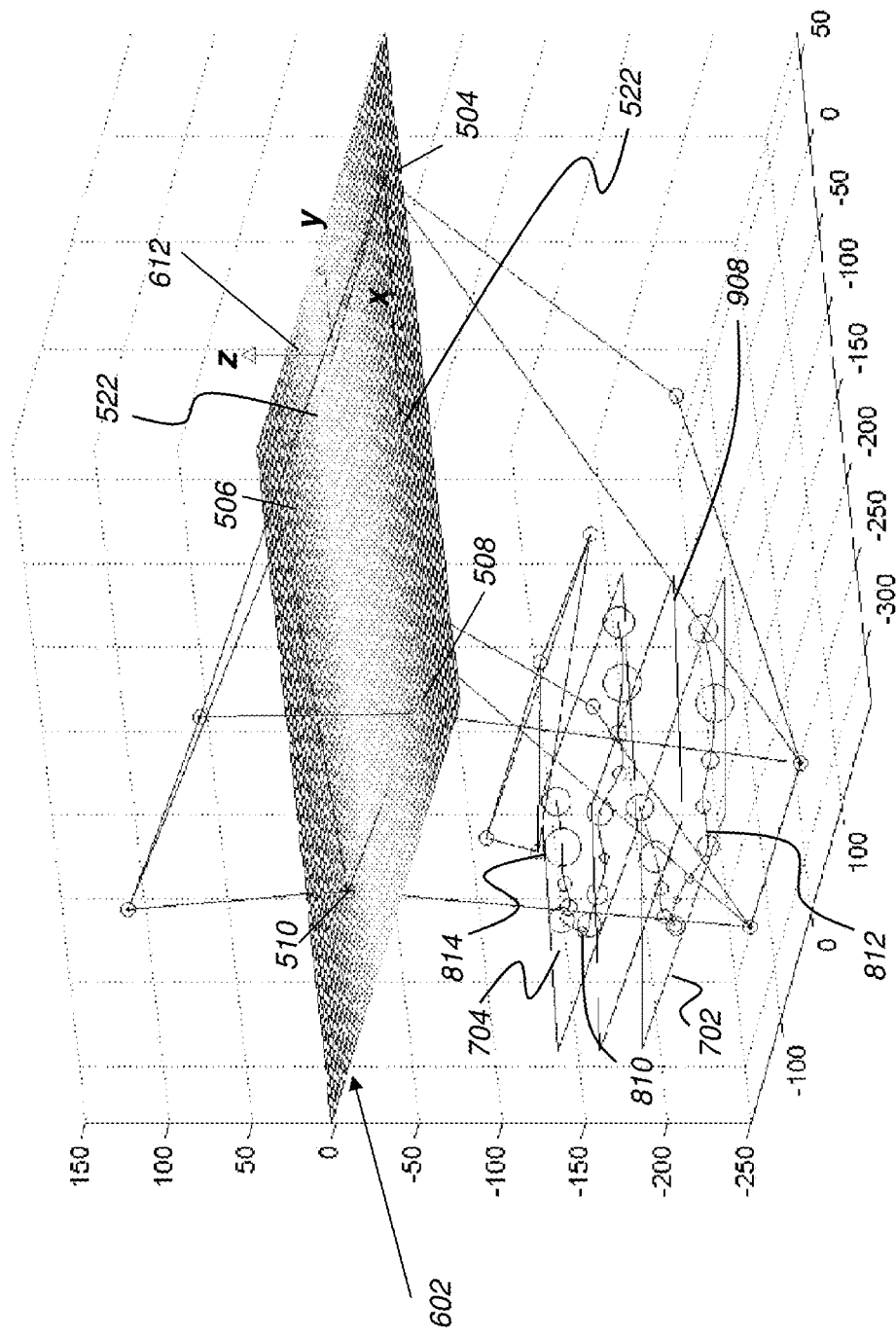

As shown in FIG. 10D, another derived parameter, an occlusal plane, 3-D plane 908, is computed from the two jaw planes 702 and 704. Occlusal plane, 3-D plane 908, lies between the two jaw planes 702 and 704. The normal of plane 908 is the average of the normal of plane 702 and normal of plane 704.

Figure 10E:
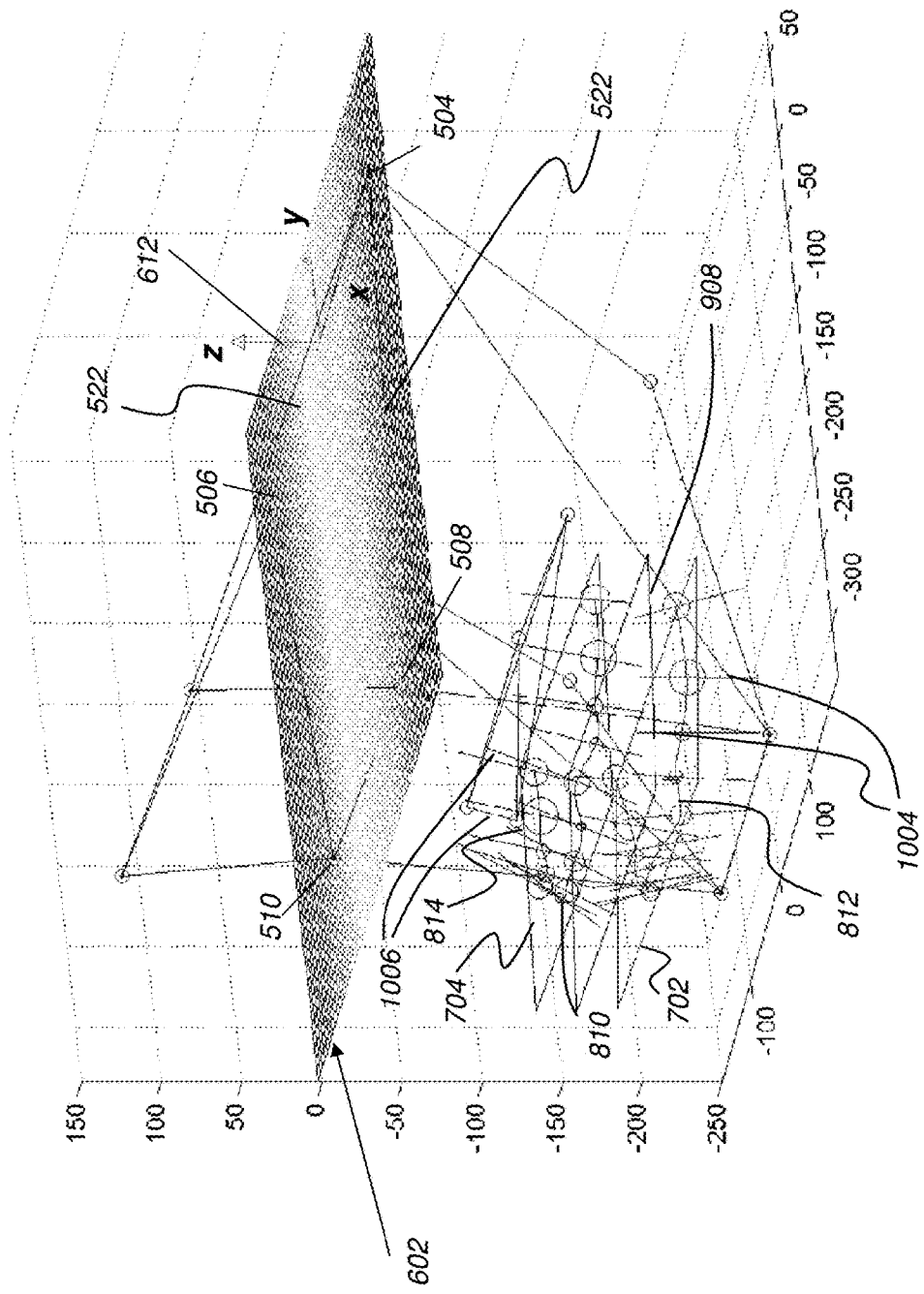

For an individual tooth, in general, the eigenvector corresponding to the largest computed eigenvalue is another derived cephalometric parameter that indicates the medial axis of the tooth. FIG. 10E shows two types of exemplary medial axes for teeth: medial axes 1006 for upper incisors and medial axes 1004 for lower incisors.

The calculated length of the medial axis of a tooth is a useful cephalometric parameter in cephalometric analysis and treatment planning along with other derived parameters. It should be noted that, instead of using the eigenvalue to set the length of the axis as proposed in the cited publication by Triel, embodiments of the present disclosure compute the actual medial axis length as a derived parameter using a different approach. A first intersection point of the medial axis with the bottom slice of the tooth volume is initially located. Then, a second intersection point of the medial axis with the top slice of the tooth volume is identified. An embodiment of the present disclosure then computes the length between the two intersection points.

Figure 11:
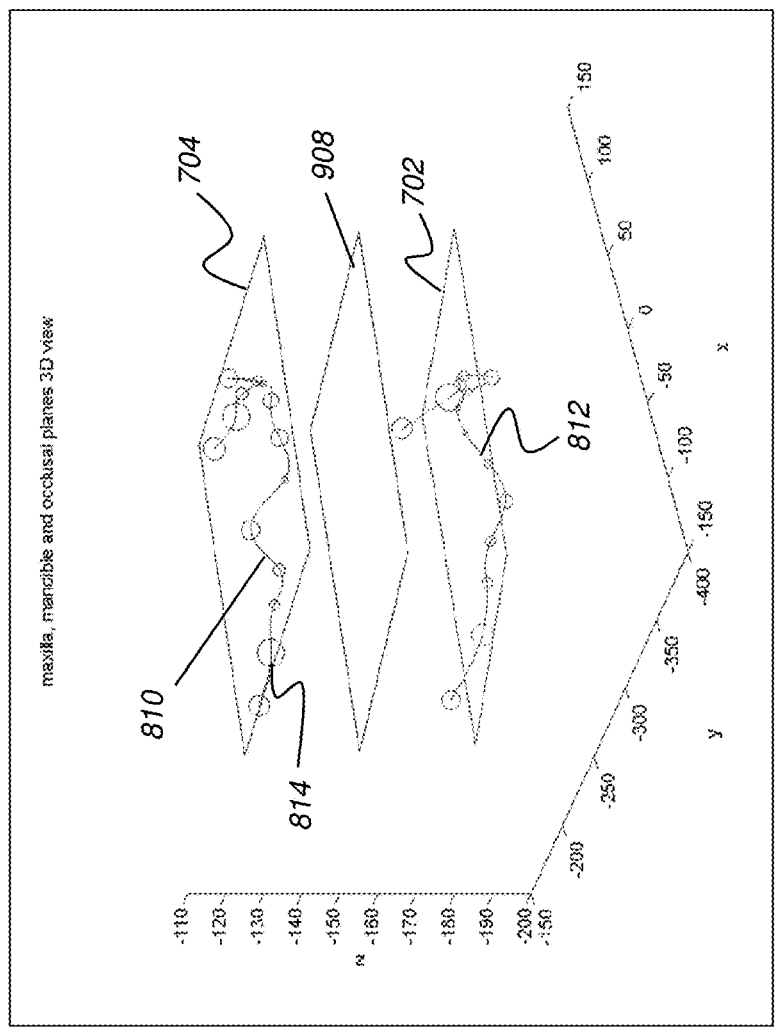
FIG. 11 is a 3-D graph showing a number of derived cephalometric parameters from segmented teeth data.

FIG. 11 shows a graph 1102 that provides a closeup view that isolates the occlusal plane 908 in relation to upper jaw plane 704 and lower jaw plane 702 and shows the relative positions and curvature of jaw curves 810 and 812.

Figure 12:
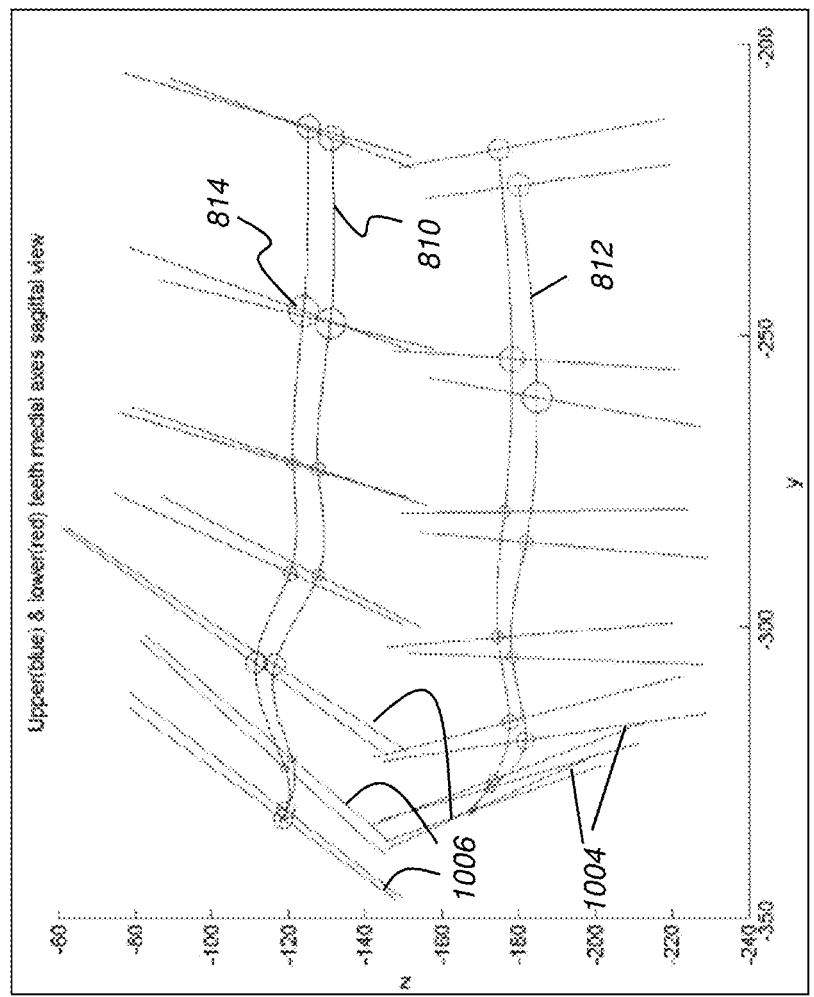
FIG. 12 is a 2-D graph showing the derived cephalometric parameters from segmented teeth data.

FIG. 12 shows a graph 1202 that shows the positional and angular relationships between the upper teeth medial axes 1006 and the lower teeth medial axes 1004.

As noted in the preceding descriptions and shown in the corresponding figures, there are a number of cephalometric parameters that can be derived from the combined volume image data, including dentition element segmentation, and operator-entered reference marks. These are computed in a computer-aided cephalometric analysis step S110 (FIG. 2).

One exemplary 3-D cephalometric analysis procedure in step S110 that can be particularly valuable relates to the relative parallelism of the maxilla (upper jaw) and mandibular (lower jaw) planes 702 and 704. Both upper and lower jaw planes 702 and 704, respectively, are derived parameters, as noted previously. The assessment can be done using the following sequence:

Project the x axis of the maxilla inertia system (that is, the eigenvectors) to the x-z plane of the t-reference system and compute an angle MX1_RF between the z axis of the t-reference system and the projection;

Project the x axis of the mandibular inertia system (that is, the eigenvectors) to the x-z plane of the t-reference system and compute an angle MD1_RF between the z axis of the t-reference system and the projection;

MX1_MD1_RF=MX1_RF−MD1_RF gives a parallelism assessment of upper and lower jaws in the x-z plane of the t-reference system;

Project the y axis of the maxilla inertia system (that is, the eigenvectors) to the y-z plane of the t-reference system and compute the angle MX2_RS between the y axis of the t-reference system and the projection;

Project the y axis of the mandibular inertia system (that is, the eigenvectors) to the y-z plane of the t-reference system and compute an angle MD2_RS between the y axis of the t-reference system and the projection;

MX2_MD2_RS=MX2_RS−MD2_RS gives a parallelism assessment of upper and lower jaws in the y-z plane of the t-reference system.

Another exemplary 3-D cephalometric analysis procedure that is executed in step S110 is assessing the angular property between the maxilla (upper jaw) incisor and mandible (lower jaw) incisor using medial axes 1006 and 1004 (FIGS. 10E, 12). The assessment can be done using the following sequence:

Project the upper incisor medial axis 1006 to the x-z plane of the t-reference system and compute an angle MX1_AF between the z axis of the t-reference system and the projection;

Project the lower incisor medial axis 1004 to the x-z plane of the t-reference system and compute an angle MD1_AF between the z axis of the t-reference system and the projection;

MX1_MD1_AF=MX1_AF−MD1_AF gives the angular property assessment of the upper and lower incisors in the x-z plane of the t-reference system;

Project the upper incisor medial axis 1006 to the y-z plane of the t-reference system and compute an angle MX2_AS between the y axis of the t-reference system and the projection;

Project the lower incisor medial axis 1004 to the y-z plane of the t-reference system and compute an angle MD2_AS between the y axis of the t-reference system and the projection;

MX2_MD2_AS=MX2_AS−MD2_AS gives the angular property assessment of upper and lower incisors in the y-z plane of the t-reference system.

Figure 13:
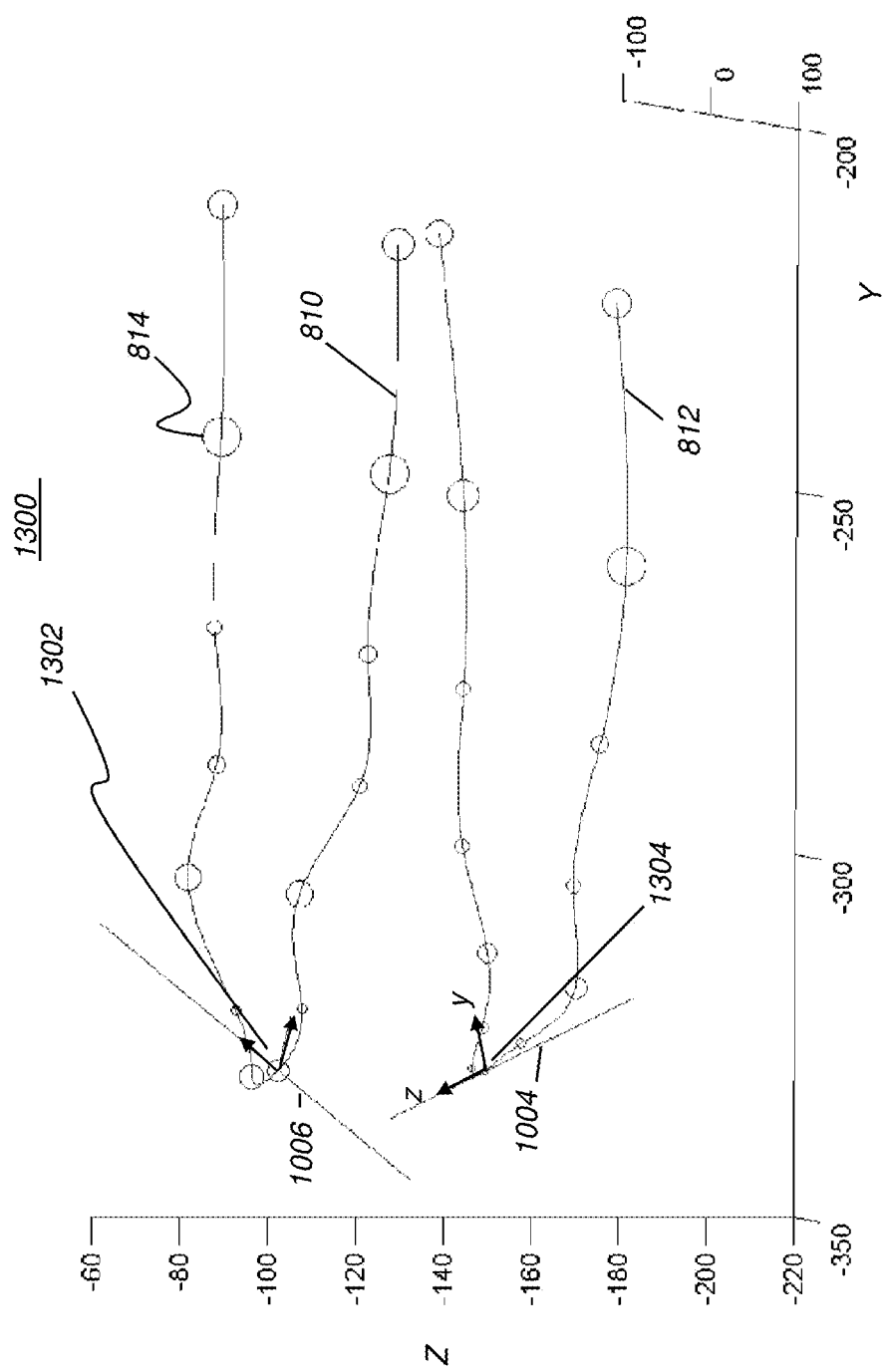
FIG. 13 is another 3-D graph showing the derived cephalometric parameters from segmented teeth data.

FIG. 13 shows a graph 1300 that shows a local x-y-z coordinate system 1302 for an upper incisor, and a local x-y-z coordinate system 1304 for a lower incisor. The local axes of the x-y-z coordinate system align with the eigenvectors associated with that particular tooth. The x axis is not shown but satisfies the right-hand system rule.

In FIG. 13, the origin of system 1302 can be selected at any place along axis 1006. An exemplary origin for system 1302 is the mass center of the tooth that is associated with axis 1006. Similarly, the origin of system 1304 can be selected at any place along axis 1004. An exemplary origin for system 1304 is the mass center of the tooth that is associated with axis 1004.

Figure 14:
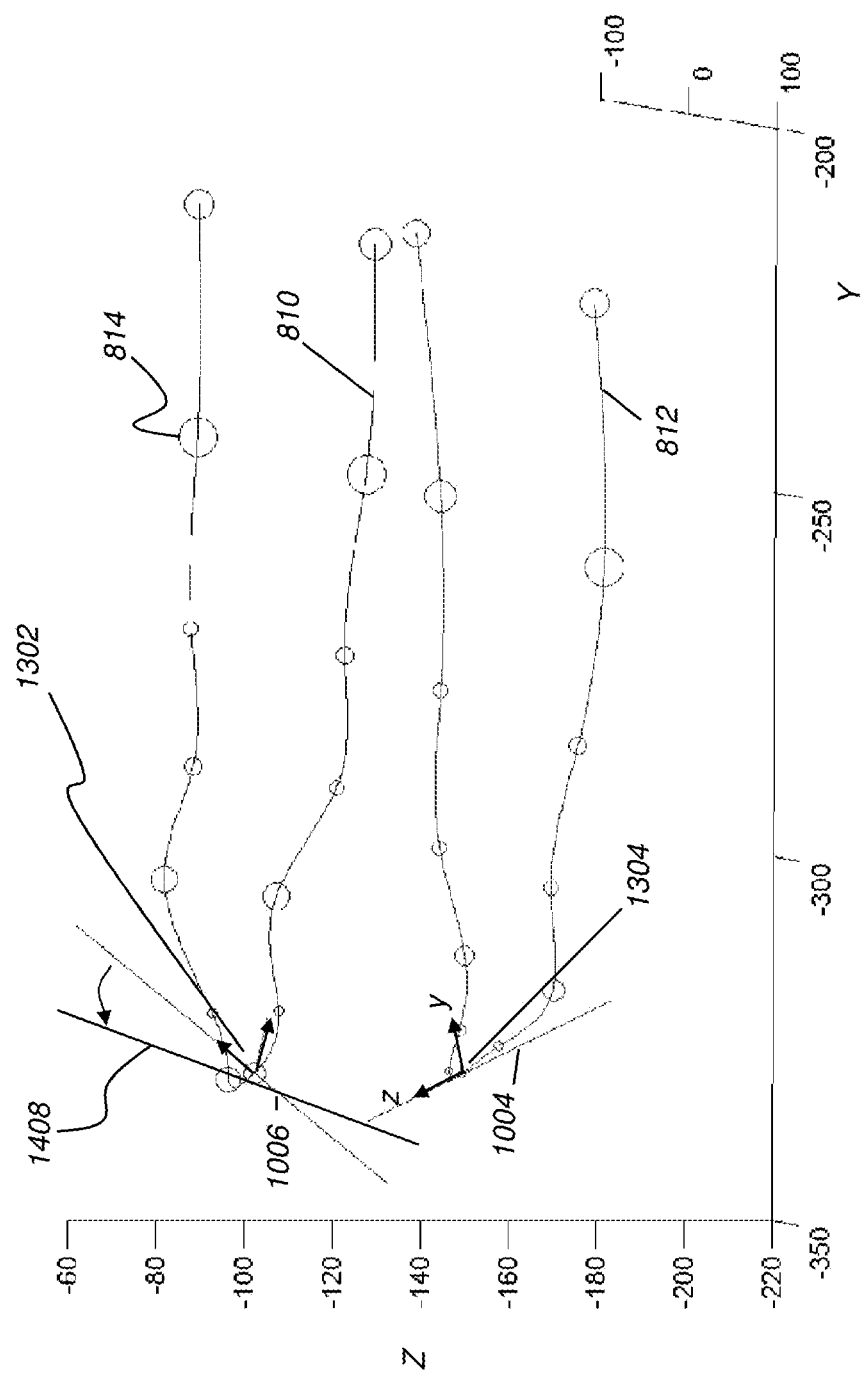
FIG. 14 is a graph showing the derived cephalometric parameters from segmented teeth data and treatment parameter.

Based on the analysis performed in Step S110 (FIG. 2), an adjustment or treatment plan is arranged in a planning step S112. An exemplary treatment plan is to rotate the upper incisor counter clockwise at a 3-D point, such as at its local coordinate system origin, and about an arbitrary 3-D axis, such as about the x axis of the local x-y-z system. The graph of FIG. 14 shows rotation to an axis position 1408.

In a treatment step S114 of FIG. 2, treatment is performed based on the planning, for example, based on upper incisor rotation. The treatment planning can be tested and verified visually in a visualization step S116 before the actual treatment takes place.

Referring back to FIG. 2, there is shown a line 120 from Step S114 to Step S102. This indicates that there is a feedback loop in the sequence 200 workflow. After the patient undergoes treatment, an immediate evaluation or, alternately, a scheduled evaluation of the treatment can be performed by entering relevant data as input to the system. Exemplary relevant data for this purpose can include results from optical, radiographic, MRI, or ultrasound imaging and/or any meaningful related measurements or results.

Figure 15:
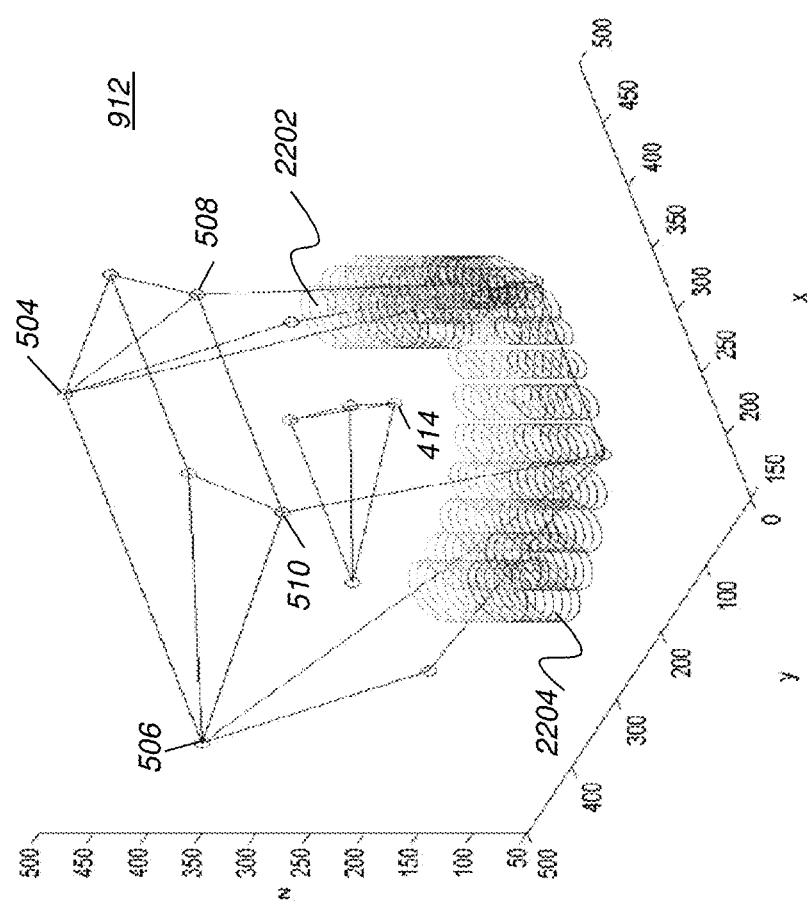
FIG. 15 is a 3-D graph that shows how tooth exclusion is learned by the system.

An optional tooth exclusion step S124 is also shown in sequence 200 of FIG. 2. For example, if the patient has had one or more teeth removed, then the teeth that complement the removed teeth can be excluded. For this step, the operator specifies one or more teeth, if any, to be excluded from the rest of the processing steps based on Treil's theory of jaw planes parallelism. The graph of FIG. 15 shows how tooth exclusion can be learned by the system, using a virtual or digital phantom 912. Digital phantom 912 is a virtual model used for computation and display that is constructed using a set of landmarks and a set of upper teeth of a digital model of an upper jaw and a set of lower teeth of a digital model of a lower jaw. Digital phantom 912 is a 3-D or volume image data model that is representative of image data that is obtained from patient anatomy and is generated using the landmark and other anatomical information provided and can be stored for reference or may be generated for use as needed. The use of various types of digital phantom is well known to those skilled in the digital radiography arts. The landmarks such as reference marks 504, 506, 508 and 510 of the digital phantom 912 correspond to the actual reference marks identified from the CBCT volume 202 (FIG. 3). These landmarks are used to compute the t-reference system 612 (FIGS. 10A-10E).

The operator can exclude one or more teeth by selecting the teeth from a display or by entering information that identifies the excluded teeth on the display.

In the FIG. 15 representation, the upper and lower teeth, such as digital teeth 2202 and 2204 of digital phantom 912 are digitally generated. The exemplary shape of a digital tooth is a cylinder, as shown. The exemplary voxel value for a digital tooth in this example is 255. It can be appreciated that other shapes and values can be used for phantom 912 representation and processing.

Figure 16A:
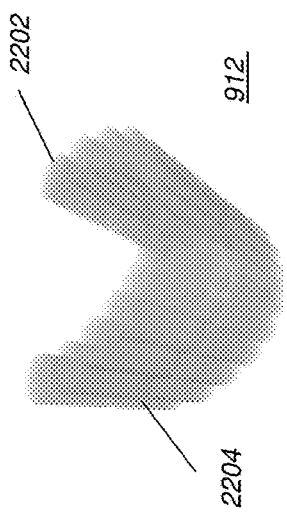
FIG. 16A is a perspective view that shows teeth of a digital phantom.

FIG. 16A shows digital teeth 2202 and 2204 of digital phantom 912. The corresponding digital teeth in the upper digital jaw and lower digital jaw are generated in a same way, with the same size and same code value.

To assess parallelism of the upper and lower digital jaws, an inertia tensor for each digital jaw is formed by using the 3-D position vectors and code values of voxels of all digital teeth in a digital jaw (see the Treil publications, cited previously). Eigenvectors are then computed from the inertia tensor. These eigenvectors, as an inertial system, mathematically describe the orientation of the jaw in the t-reference system 612 (FIG. 10A). As noted earlier, the eigenvectors, computed from the inertial tensor data, are one type of derived cephalometric parameter.

Figure 16B:
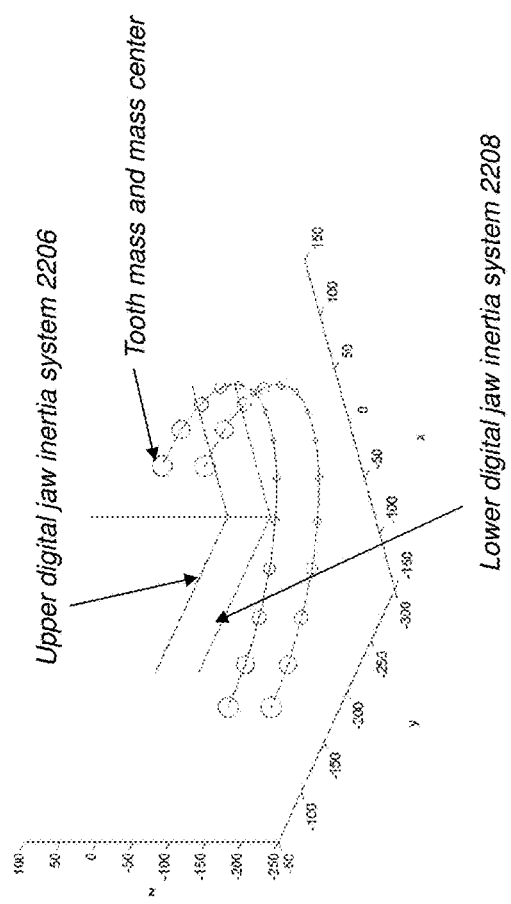
FIG. 16B is a 3-D graph showing computed axes of inertia systems for upper and lower jaws.
Figure 17B:
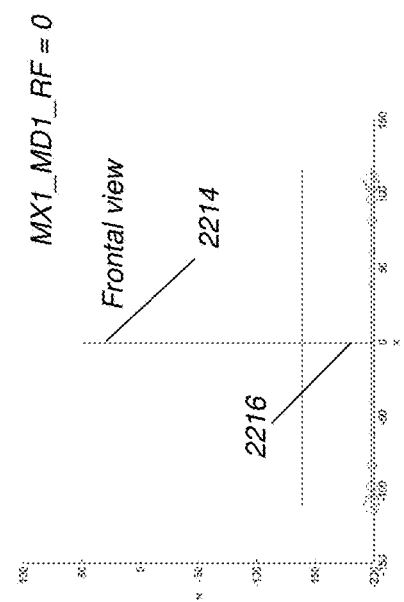
FIG. 17B is a graph showing parallelism for specific tooth structures.
Figure 17A:
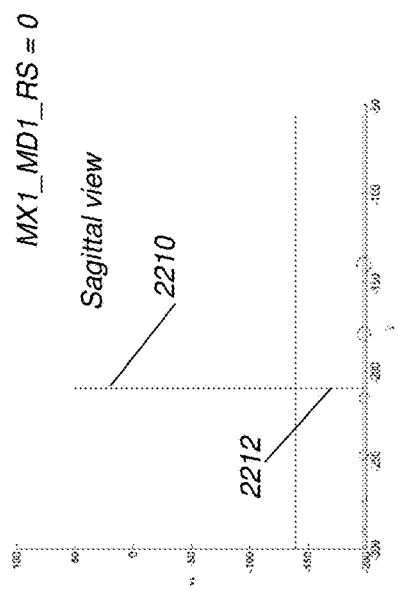
FIG. 17A is a graph showing parallelism for specific tooth structures.

As shown in FIG. 16B, the computed axes of an upper digital jaw inertia system 2206 and a lower digital jaw inertia system 2208 are in parallel for the generated digital phantom 912 as expected, since the upper and lower jaw teeth are created in the same way. FIG. 17A shows this parallelism in the sagittal view along a line 2210 for the upper jaw and along a line 2212 for the lower jaw; FIG. 17B shows parallelism in the frontal (coronal) view at a line 2214 for the upper jaw and at a line 2216 for the lower jaw.

Figure 18B:
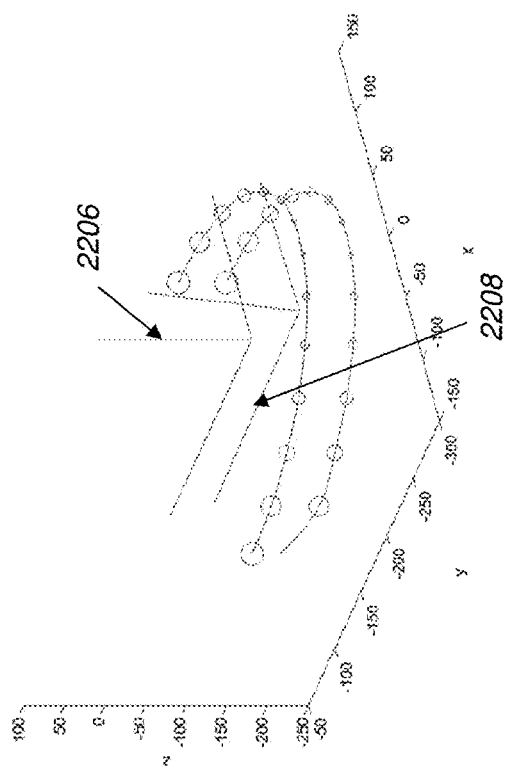
FIG. 18B is a graph showing computed axes of inertia systems for upper and lower jaws for the example of FIG. 18A.
Figure 18A:
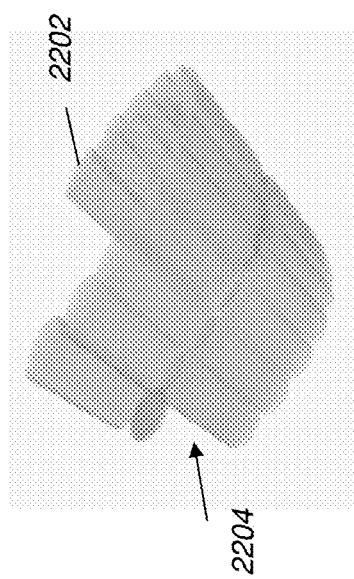
FIG. 18A is a perspective view that shows teeth of a digital phantom with a tooth missing.
Figure 19B:
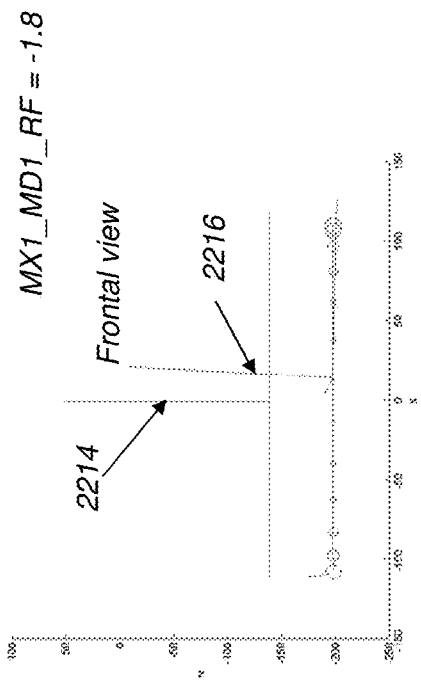
FIG. 19B is a graph showing lack of parallelism for specific tooth structures.
Figure 19A:
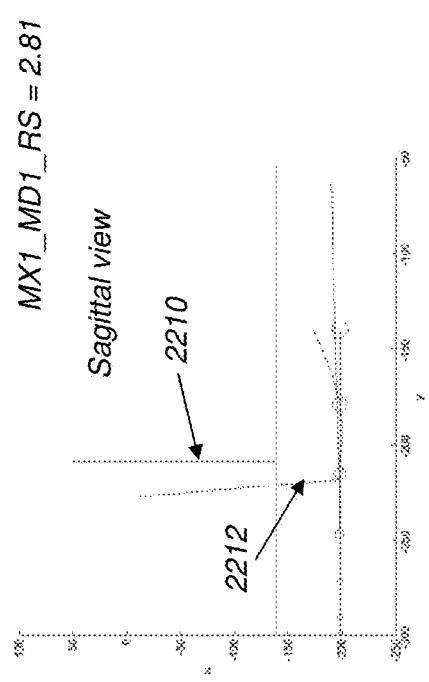
FIG. 19A is a graph showing lack of parallelism for specific tooth structures.
Figures 20A, 20B:
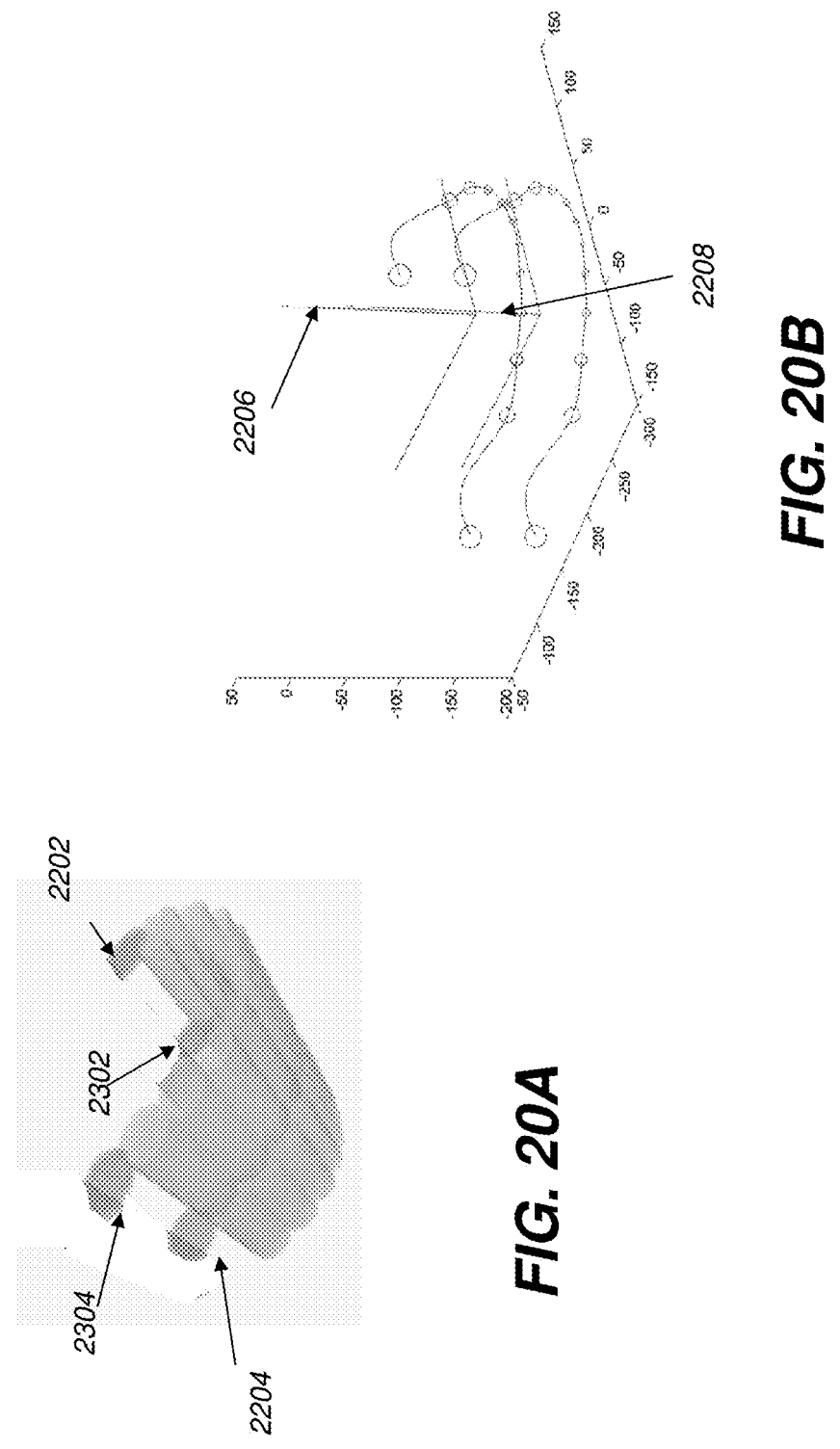

Referring to FIGS. 18A and 18B, there is shown a case in which digital tooth 2204 is missing. The computed axes of upper digital jaw inertia system 2206 and lower digital jaw inertia system 2208 are no longer in parallel. In corresponding FIGS. 19A and 19B, this misalignment can also be examined in a sagittal view along a line 2210 for the upper jaw and a line 2212 for the lower jaw; in the frontal view along a line 2214 for the upper jaw and a line 2216 for the lower jaw. According to an embodiment of the present disclosure, this type of misalignment of upper and lower jaw planes (inertia system) due to one or more missing teeth can be corrected by excluding companion teeth of each missing tooth as illustrated in FIGS. 20A and 20B. The companion teeth for tooth 2204 are teeth 2304, 2302 and 2202. Tooth 2304 is the corresponding tooth in the upper jaw for tooth 2204. Teeth 2202 and 2302 are the corresponding teeth at the other side for the teeth 2304 and 2204. After excluding the companion teeth for the missing tooth 2204, the computed axes of inertia system 2206 for the upper jaw and inertia system 2208 for the lower jaw are back in parallel.

Figure 21B:
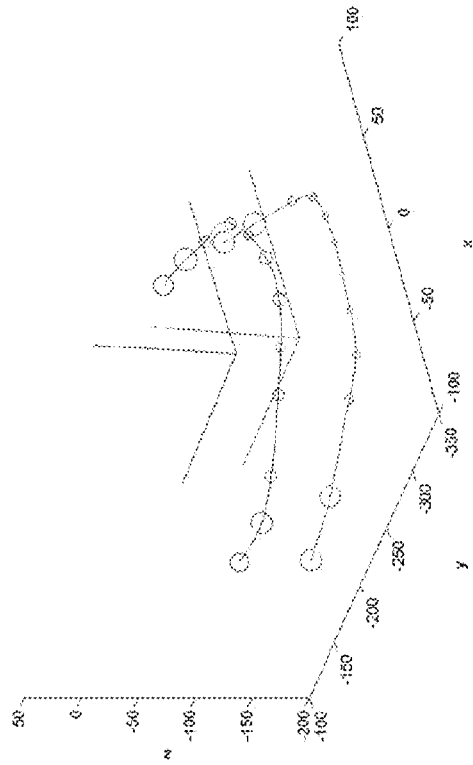
FIG. 21B is a graph showing computed axes of inertia systems for upper and lower jaws for the example of FIG. 21A.
Figure 21A:
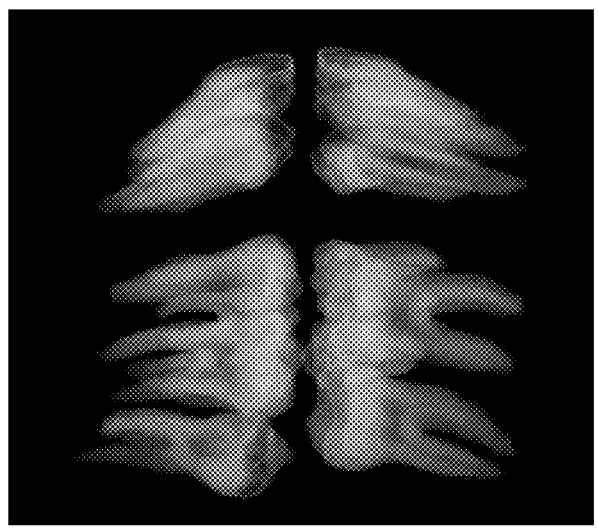
FIG. 21A is an example showing tooth exclusion for a missing tooth.

FIGS. 21A and 21B illustrate segmented teeth from a CBCT volume in a case where companion teeth are excluded for a missing tooth. The segmentation results are shown in an image 2402. The computed axes of inertia systems for the upper and lower jaws are in parallel as demonstrated in a graph 2404.

Figure 22A:
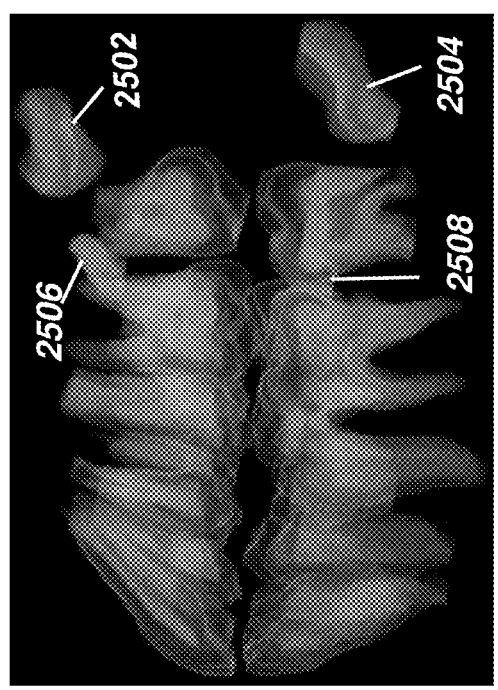
FIG. 22A is an example showing tooth exclusion for a missing tooth.
Figure 22B:
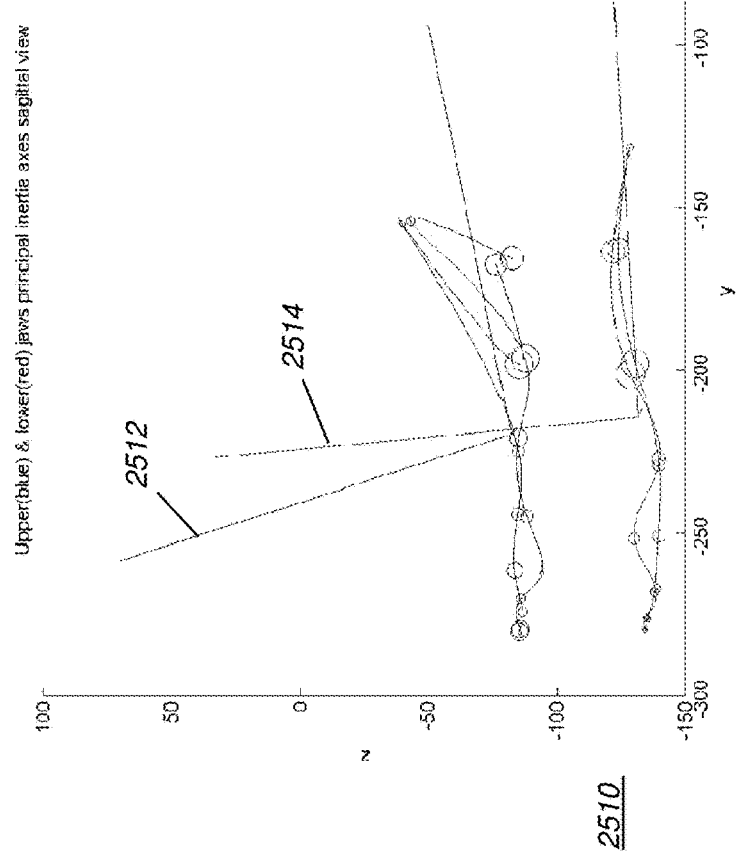
FIG. 22B is a graph showing computed axes of inertia systems for upper and lower jaws for the example of FIG. 22A.

FIGS. 22A and 22B show the method of exclusion of companion teeth applied to another patient using tooth exclusion step S124 (FIG. 2). As shown in an image 2500, teeth 2502, 2504, 2506 and 2508 are not fully developed. Their positioning, size, and orientation severely distort the physical properties of the upper jaw and lower jaw in terms of inertia system computation. A graph 2510 in FIG. 22B depicts the situation where upper jaw inertia system 2512 and lower jaw inertia system 2514 are severely misaligned (not in parallel).

Figure 23A:
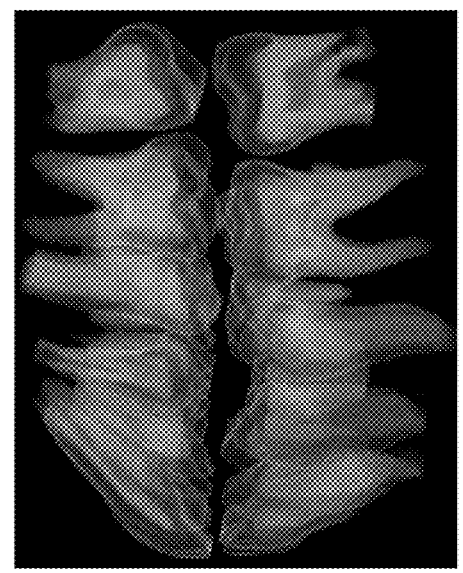
FIG. 23A is an image that shows the results of excluding specific teeth.
Figure 23B:
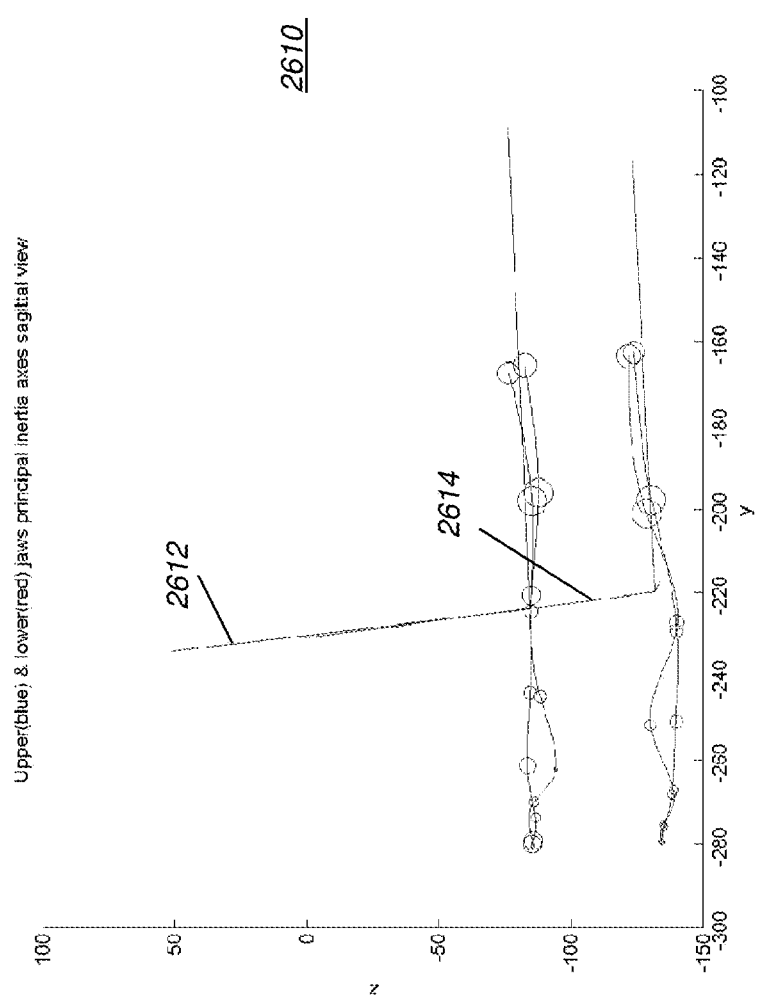
FIG. 23B is a graph showing computed axes of inertia systems for upper and lower jaws for the example of FIG. 23A.

FIGS. 23A and 23B show the results of excluding specific teeth from the image. An image 2600 shows the results of excluding teeth 2502, 2504, 2506 and 2508 from image 2500 of FIG. 22A. Without the disturbance of these teeth, the axes of inertia system 2612 of the upper jaw and inertia system 2614 lower jaw of the teeth shown in image 2600 are in parallel as depicted in a graph 2610.

Biometry Computation

Given the entered landmark data for anatomic reference points, segmentation of dentition elements such as teeth, implants, and jaws and related support structures, and the computed parameters obtained as described previously, detailed biometry computation can be performed and its results used to assist setup of a treatment plan and monitoring ongoing treatment progress. Referring back to FIG. 8, the biometry computation described subsequently gives more details about step S250 for analyzing and displaying parameters generated from the recorded reference marks.

Figure 24:
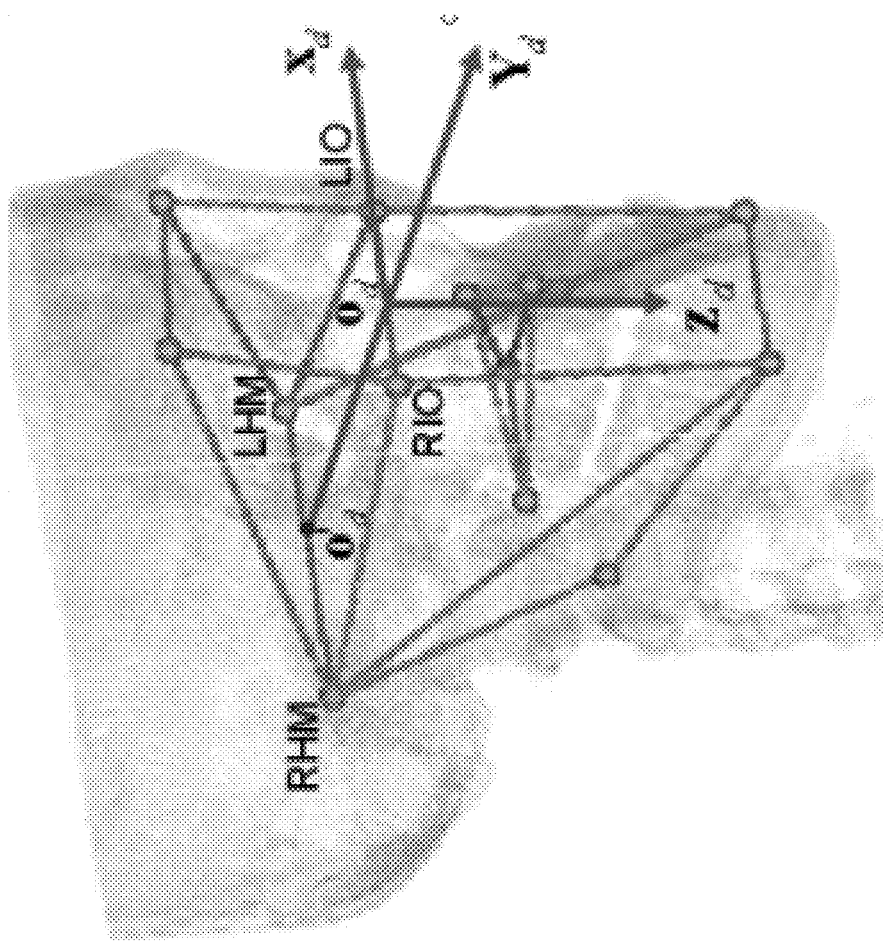
FIG. 24 shows a number of landmarks and coordinate axes or vectors of the DOL reference system.

According to an embodiment of the present disclosure, the entered landmarks and computed inertia systems of teeth are transformed from the original CBCT image voxel space to an alternate reference system, termed the direct orthogonal landmark (DOL) reference system, with coordinates ($x_d$, $y_d$, $z_d$). FIG. 24 shows a number of landmarks and coordinate axes or vectors of the DOL reference system. Landmarks RIO and LIO indicate the infraorbital foramen; landmarks RHM and LHM mark the malleus. The origin $o_d$ of ($x_d$, $y_d$, $z_d$) is selected at the middle of the line connecting landmarks RIO and LIO. Vector $x_d$ direction is defined from landmark RIO to LIO. A YZ plane is orthogonal to vector $x_d$ at point $o_d$. There is an intersection point $o'_d$ of plane YZ and the line connecting RHM and LHM. Vector $y_d$ direction is from $o'_d$ to $o_d$. Vector $z_d$ is the cross product of $x_d$ and $y_d$.

Figure 25:
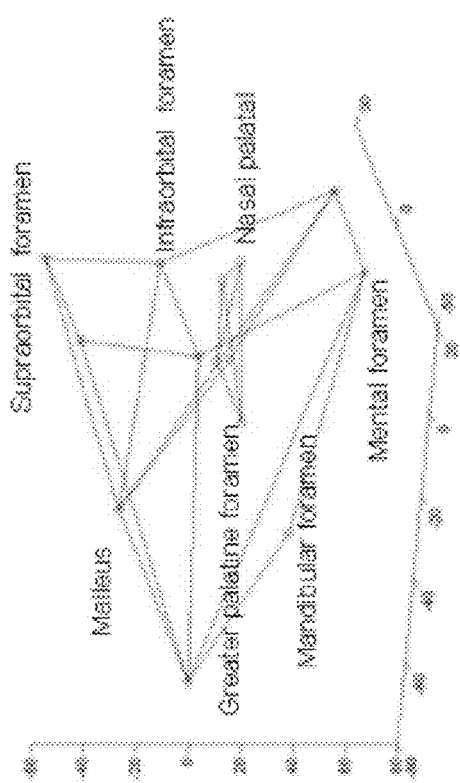
FIG. 25 shows landmark remapping to the alternate space of the DOL reference system.
Figure 26:
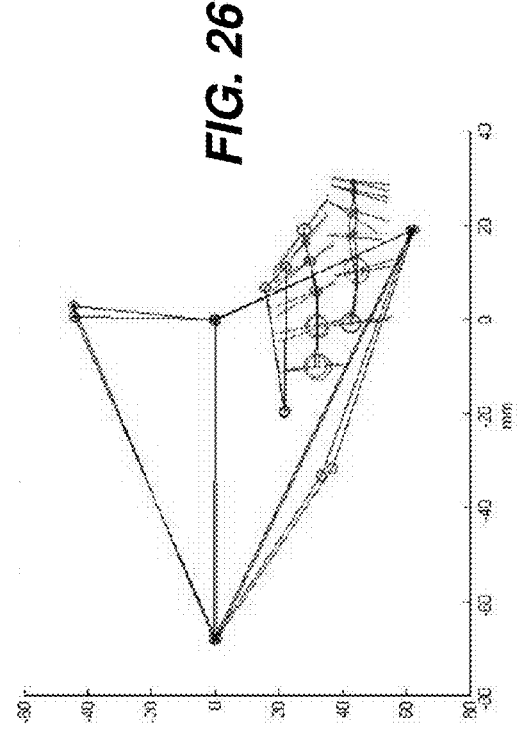
FIG. 26 shows, from a side view, an example with transformed teeth inertia systems using this re-mapping.

Using this transformation, the identified landmarks can be re-mapped to the coordinate space shown in FIG. 25. FIG. 26 shows, from a side view, an example with transformed inertia systems using this re-mapping.

By way of example, and not of limitation, the following listing identifies a number of individual data parameters that can be calculated and used for further analysis using the transformed landmark, dentition segmentation, and inertial system data.

A first grouping of data parameters that can be calculated using landmarks in the transformed space gives antero-posterior values:
1. Antero-posterior.alveolar.GIM-Gim: y position difference between the mean centers of inertia of upper and lower incisors.
2. Antero-posterior.alveolar.GM-Gm: difference between the mean centers of inertia of upper and lower teeth.
3. Antero-posterior.alveolar.TqIM: mean torque of upper incisors.
4. Antero-posterior.alveolar.Tqim: mean torque of lower incisors.
5. Antero-posterior.alveolar.(GIM+Gim)/2: average y position of GIM and Gim.
6. Antero-posterior.basis.MNP-MM: y position difference between mean nasal palatal and mean mental foramen.
7. Antero-posterior.basis.MFM-MM: actual distance between mean mandibular foramen and mean mental foramen.
8. Antero-posterior.architecture.MMy: y position of mean mental foramen.
9. Antero-posterior.architecture.MHM-MM: actual distance between mean malleus and mean mental foramen.

A second grouping gives vertical values:
10. Vertical.alveolar.Gdz: z position of inertial center of all teeth.
11. Vertical.alveolar.MxII-MdII: difference between the angles of second axes of upper and lower arches.
12. Vertical.basis.<MHM-MIO,MFM-MM>: angle difference between the vectors MHM-MIO and MFM-MM.
13. Vertical. architecture.MMz: z position of mean mental foramen.
14. Vertical. architecture.13: angle difference between the vectors MHM-MIO and MHM-MM.

Transverse values are also provided:
15. Transverse.alveolar.dM-dm: difference between upper right/left molars distance and lower right/left molars distance
16. Transverse.alveolar.TqM-Tqm: difference between torque of upper $1^{st}$ & $2^{nd}$ molars and torque of lower $1^{st}$ & $2^{nd}$ molars.
17. Transverse.basis.(RGP-LGP)/(RFM-LFM): ratio of right/left greater palatine distance and mandibular foramen distance.
18. Transverse.architecture.(RIO-LIO)/(RM-LM): ratio of right/left infraorbital foramen and mental foramen distances.

Other calculated or "deduced" values are given as follows:
19. Deduced.hidden.GIM: mean upper incisors y position.
20. Deduced.hidden.Gim: mean lower incisors y position.
21. Deduced.hidden.(TqIM+Tqim)/2: average of mean torque of upper incisors and mean torque of lower incisors.
22. Deduced.hidden.TqIM-Tqim: difference of mean torque of upper incisors and mean torque of lower incisors.
23. Deduced.hidden.MNPy: mean nasal palatal y position.
24. Deduced.hidden.GIM-MNP(y): difference of mean upper incisors y position and mean nasal palatal y position.
25. Deduced.hidden.Gim-MM(y): mean mental foramen y position.
26. Deduced.hidden.Gdz/(MMz-Gdz): ratio between value of Gdz and value of MMz-Gdz.

It should be noted that this listing is exemplary and can be enlarged, edited, or changed in some other way within the scope of the present disclosure.

In the exemplary listing given above, there are 9 parameters in the anterior-posterior category, 5 parameters in the vertical category and 4 parameters in the transverse category. Each of the above categories, in turn, has three types: alveolar, basis, and architectural. Additionally, there are 8 deduced parameters that may not represent a particular spatial position or relationship but that are used in subsequent computation. These parameters can be further labeled as normal or abnormal.

Normal parameters have a positive relationship with anterior-posterior disharmony, that is, in terms of their values:

Class III<Class I<Class II.

wherein Class I values indicate a normal relationship between the upper teeth, lower teeth and jaws or balanced bite; Class II values indicate that the lower first molar is posterior with respect to the upper first molar; Class III values indicate that the lower first molar is anterior with respect to the upper first molar.

Abnormal parameters have a negative relationship with anterior-posterior disharmony, that is, in terms of their bite-related values:

Class II<Class I<Class III.

Embodiments of the present disclosure can use an analysis engine in order to compute sets of probable conditions that can be used for interpretation and as guides to treatment planning. FIGS. 27-38 show various aspects of analysis engine operation and organization and some of the text, tabular, and graphical results generated by the analysis engine. It should be noted that a computer, workstation, or host processor can be configured as an analysis engine according to a set of preprogrammed instructions that accomplish the requisite tasks and functions.

Figure 27:
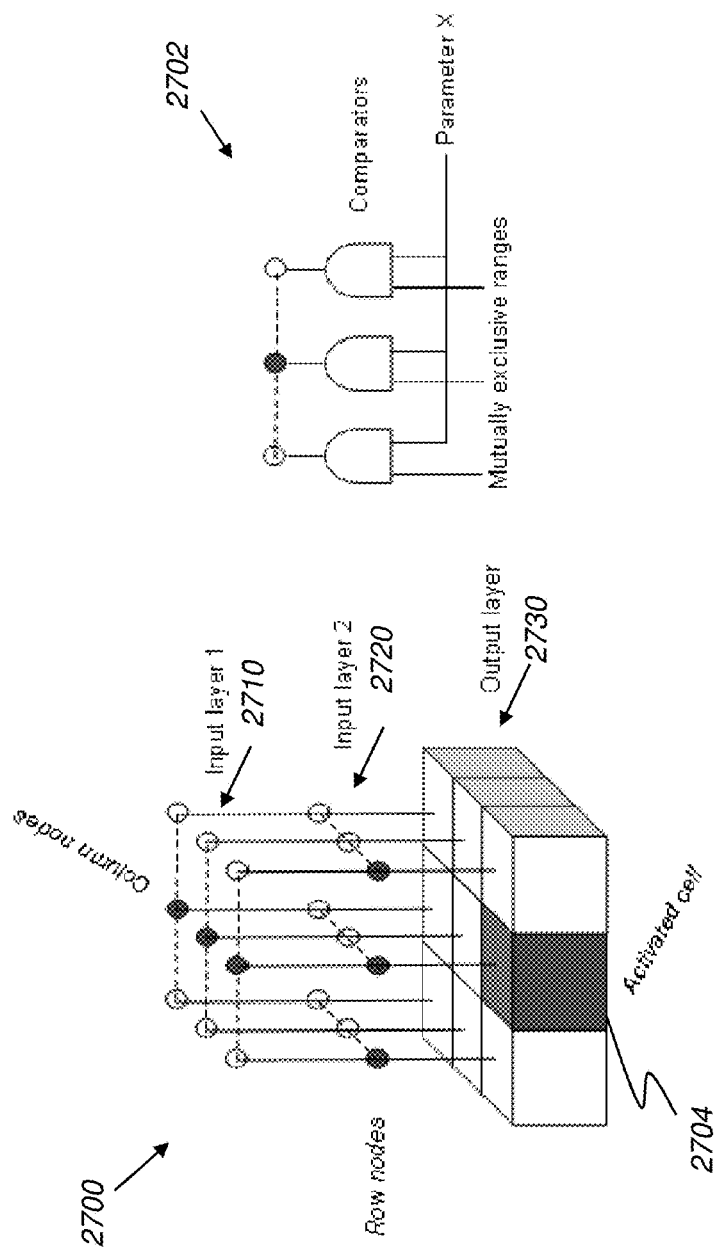
FIG. 27 is a schematic diagram that shows an independent network for the analysis engine according to an embodiment of the present disclosure.

According to an embodiment of the present disclosure, an analysis engine can be modeled as a three-layer network 2700 as shown in FIG. 27. In this model, row and column node inputs can be considered to be directed to a set of comparators 2702 that provide a binary output based on the row and column input signals. One output cell 2704 is activated for each set of possible input conditions, as shown. In the example shown, an input layer 1 2710 is fed with one of the 26 parameters listed previously and an input layer 2

2720 is fed with another one of the 26 parameters. An output layer 2730 contains 9 cells each one of which represents one probable analysis if the two inputs meet certain criterion, that is, when their values are within particular ranges.

Figure 28:
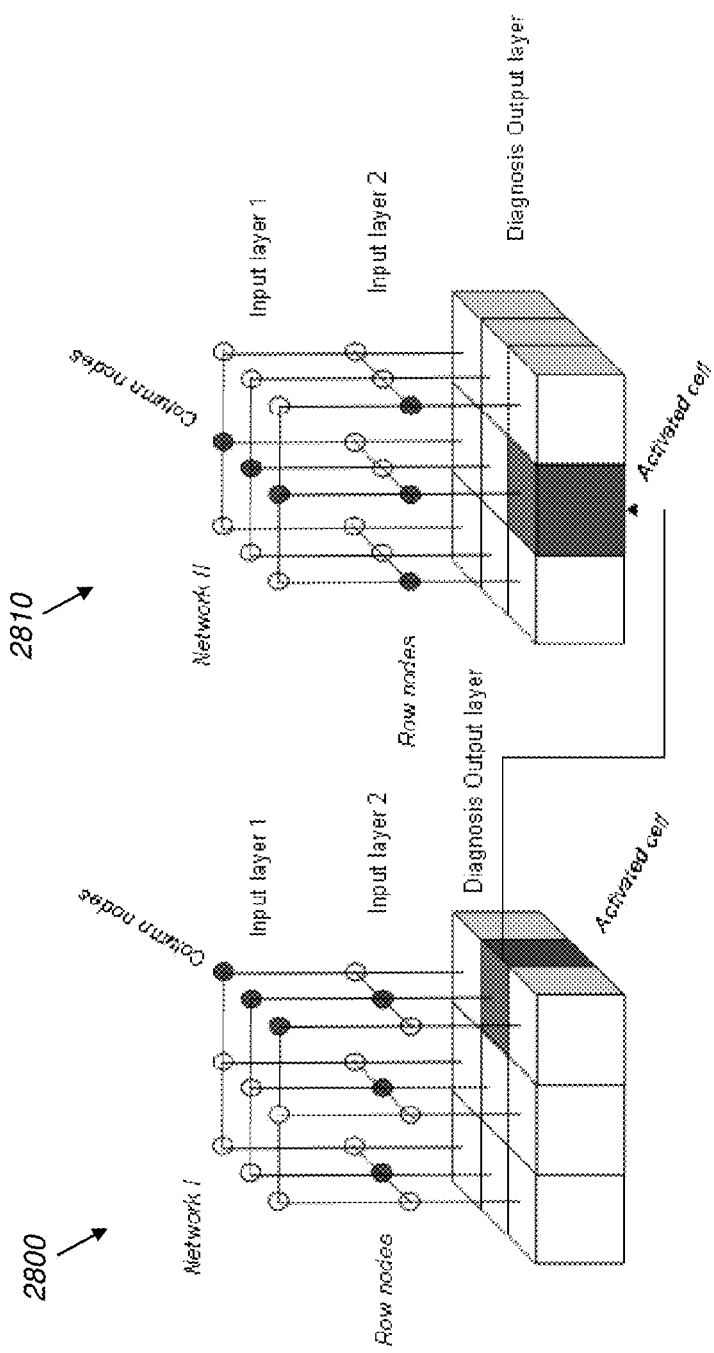
FIG. 28 is a schematic diagram that shows a dependent or coupled network for the analysis engine according to an embodiment of the present disclosure.

According to an embodiment of the present disclosure, the analysis engine has thirteen networks. These include independent networks similar to that shown in FIG. 27 and coupled networks 2800 and 2810 as shown in FIG. 28. An algorithm shown in FIG. 29 describes the operation of an independent analysis network, such as that shown in the example of FIG. 27. Here, values x and y are the input parameter values; m represents the network index; D(i,j) is the output cell. The steps of "evaluate vector $c_m$" for column values and "evaluate vector $r_m$" for row values check to determine what evaluation criterion the input values meet. For example, in the following formula, if $-\infty < x_m \leq \mu_{x_m}$ then $c_m$=[true, false, false].

The coupled network of FIG. 28 combines results from two other networks and can operate as described by the algorithm in FIG. 30. Again, values x and y are the input values; m represents the network index; D(i,j) is the output cell. The steps of "evaluate vector $c_k$" for column values and "evaluate vector $r_k$" for row values check to determine what evaluation criterion the input values meet.

In a broader aspect, the overall arrangement of networks using the independent network model described with reference to FIG. 27 or the coupled network model described with reference to FIG. 28 allow analysis to examine, compare, and combine various metrics in order to provide useful results that can be reported to the practitioner and used for treatment planning.

Figure 31A:
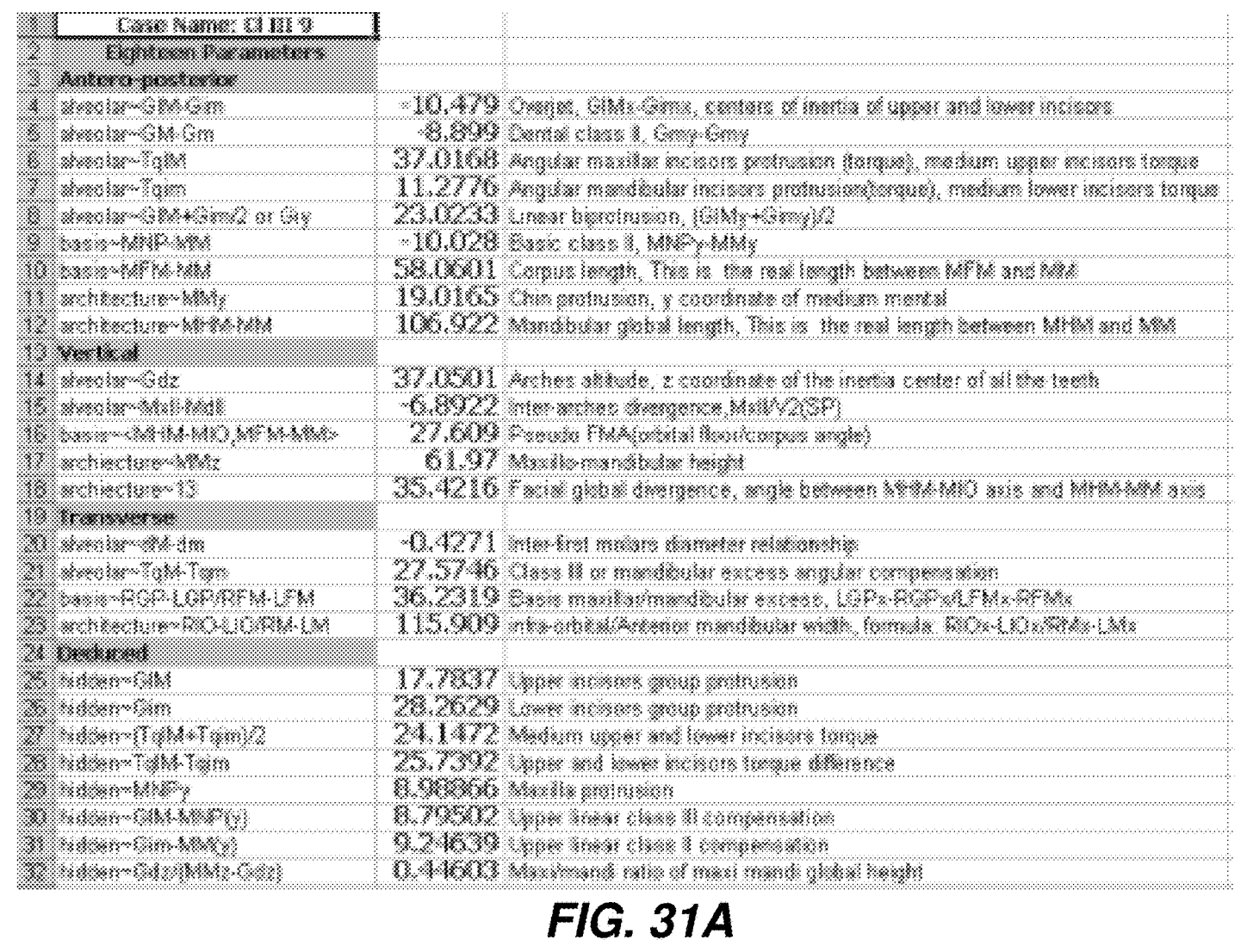
Figure 31B:
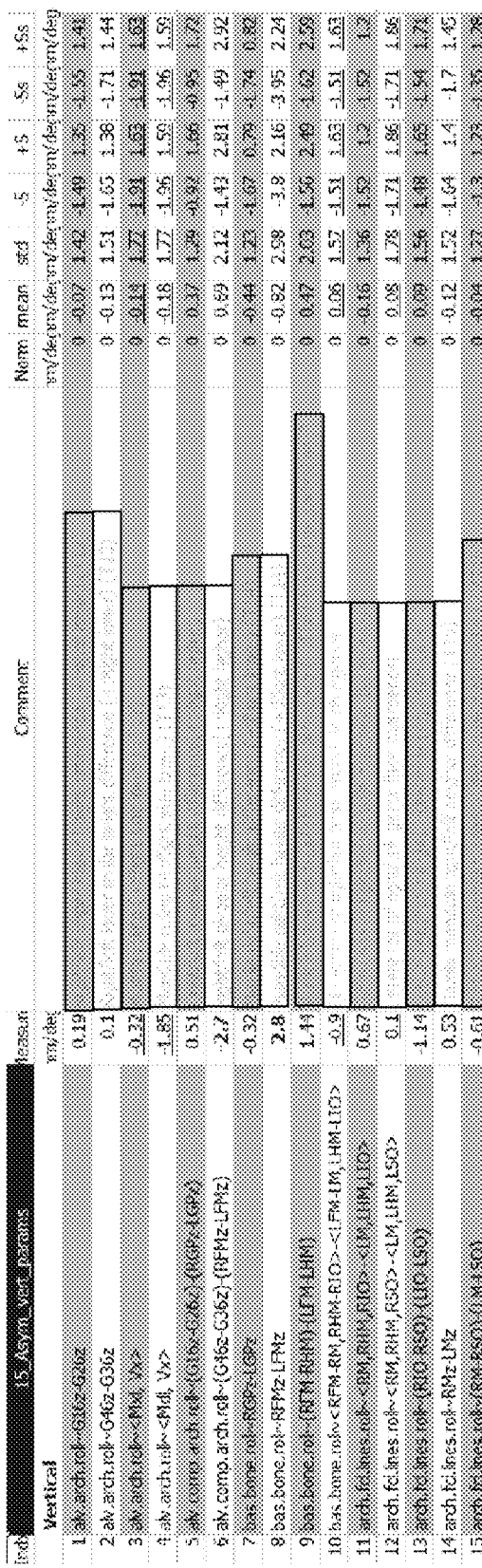
Figure 31C:
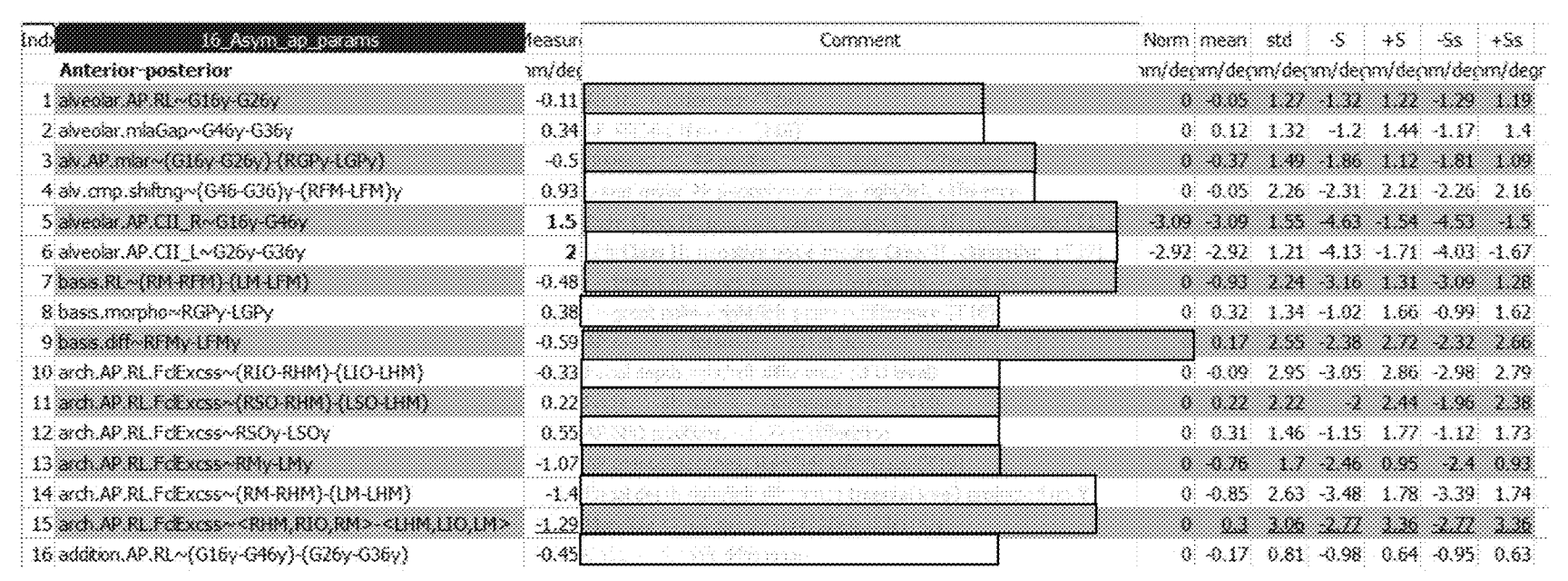
Figure 31D:
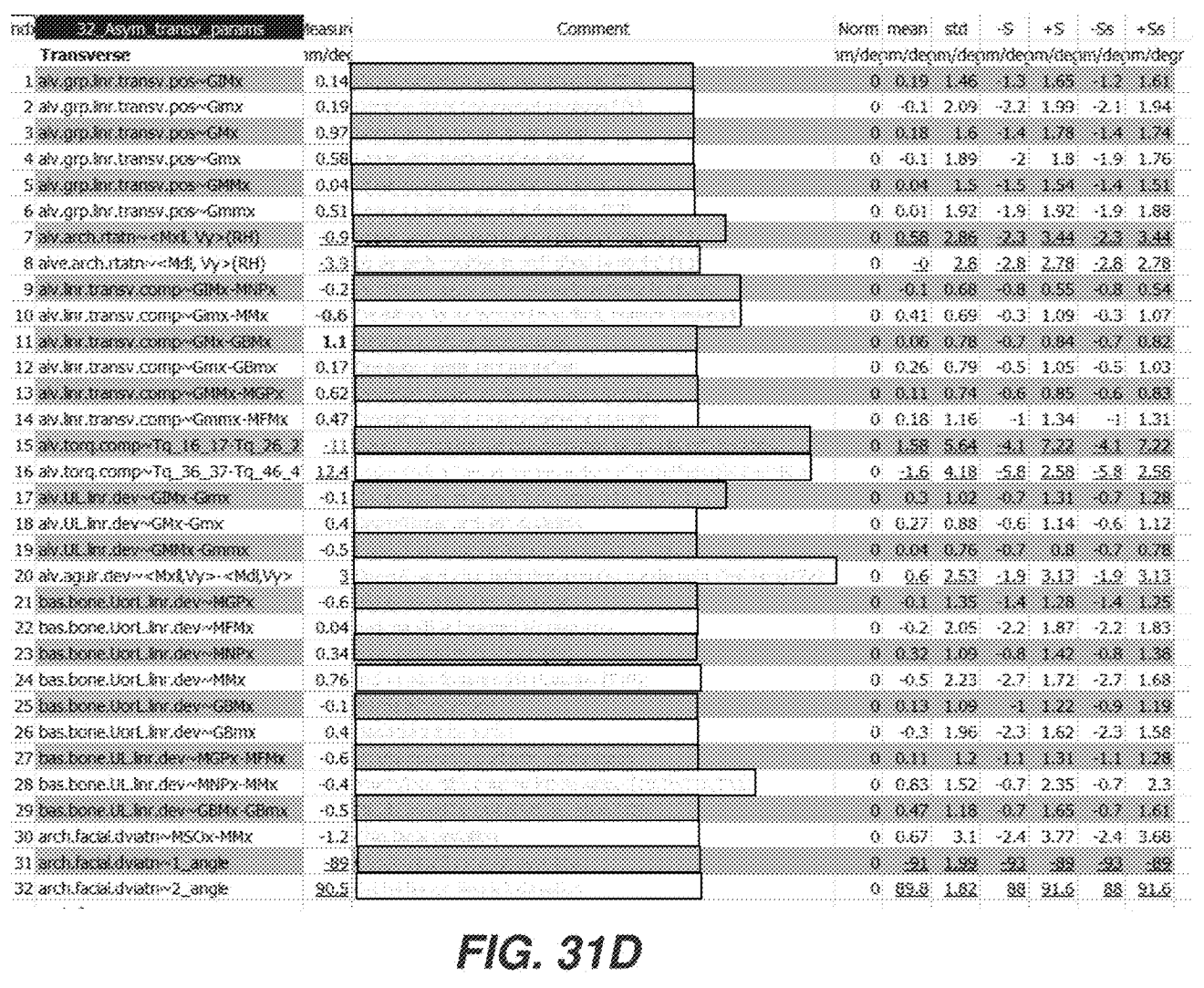
Figures 32A, 32B:
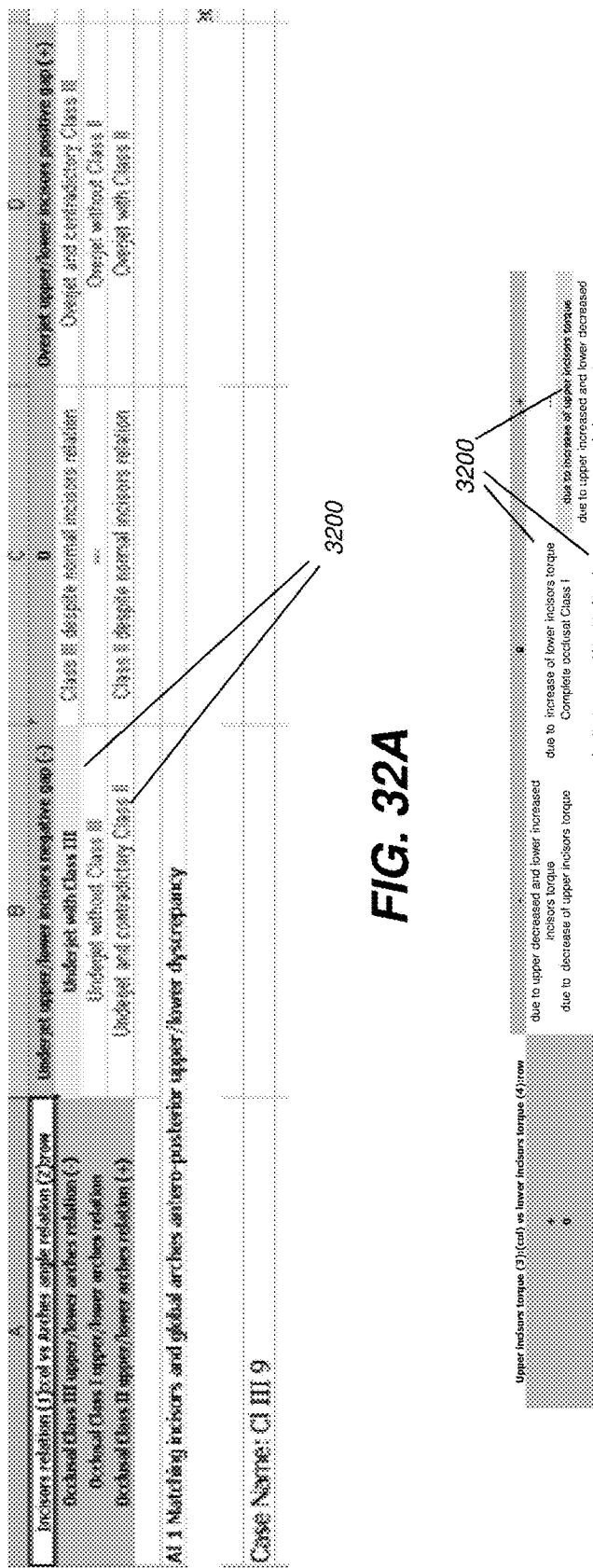
FIG. 32A shows exemplary tabulated results for a particular example with bite analysis and arches angle characteristics.
FIG. 32B shows exemplary tabulated results for a particular example for torque of upper and lower incisors.

FIG. 31A lists, for a particular patient, example parameters as numerical values and their interpretation with respect mainly to malocclusion of teeth, based on the listing of 26 parameters given previously. FIGS. 31B, 31C and 31D list, for a particular patient, example parameters as numerical values and their interpretation with respect to maxilofacial asymmetry, based on the listing of total 63 parameters given in an exemplary embodiment of this application. FIG. 32A shows exemplary tabulated results 3200 for a particular example with bite analysis and arches angle characteristics. In the example of FIG. 32A, the columns indicate an underjet, normal incisors relation, or overjet condition. Rows represent occlusal classes and arches angle conditions. As FIG. 32A shows, highlighting can be used to accentuate the display of information that indicates an abnormal condition or other condition of particular interest. For the particular patient in the FIG. 32A example, analysis indicates, as a result, an underjet condition with Class III bite characteristics. This result can be used to drive treatment planning, depending on severity and practitioner judgment.

FIG. 32B shows exemplary tabulated results 3200 for another example with analysis of torque for upper and lower incisors, using parameters 3 and 4 from the listing given previously.

FIG. 32C shows exemplary tabulated results 3200 for another example with assessment of biretrusion or biprotrusion using calculated parameters given earlier as parameters (5) and (21).

FIG. 32D shows an exemplary summary listing of results for cephalometric analysis of a particular patient. The listing that is shown refers to analysis indications taken relative to parameters 1-26 listed previously. In the particular example of FIG. 32D, there are 13 results for parameter comparisons using biometric parameters and dentition information derived as described herein. Additional or fewer results could be provided in practice. FIG. 32E shows a detailed listing for one of the conditions reported in a tabular listing with a table 3292 with cells 3294 as shown subsequently (FIG. 35).

Results information from the biometry computation can be provided for the practitioner in various different formats. Tabular information such as that shown in FIGS. 31A-32E can be provided in file form, such as in a comma-separated value (CSV) form that is compatible for display and further calculation in tabular spreadsheet arrangement, or may be indicated in other forms, such as by providing a text message. A graphical display, such as that shown in FIG. 26, can alternately be provided as output, with particular results highlighted, such as by accentuating the intensity or color of the display for features where measured and calculated parameters show abnormal biometric relations, such as overjet, underjet, and other conditions.

The computed biometric parameters can be used in an analysis sequence in which related parameters are processed in combination, providing results that can be compared against statistical information gathered from a patient population. The comparison can then be used to indicate abnormal relationships between various features. This relationship information can help to show how different parameters affect each other in the case of a particular patient and can provide resultant information that is used to guide treatment planning.

Referring back to FIG. 1, memory 132 can be used to store a statistical database of cephalometric information gathered from a population of patients. Various items of biometric data that provides dimensional information about teeth and related supporting structures, with added information on bite, occlusion, and interrelationships of parts of the head and mouth based on this data can be stored from the patient population and analyzed. The analysis results can themselves be stored, providing a database of predetermined values capable of yielding a significant amount of useful information for treatment of individual patients. According to an embodiment of the present disclosure, the parameter data listed in FIGS. 31A and 31B are computed and stored for each patient, and may be stored for a few hundred patients or for at least a statistically significant group of patients. The stored information includes information useful for determining ranges that are considered normal or abnormal and in need of correction. Then, in the case of an individual patient, comparison between biometric data from the patient and stored values calculated from the database can help to provide direction for an effective treatment plan.

As is well known to those skilled in the orthodontic and related arts, the relationships between various biometric parameters measured and calculated for various patients can be complex, so that multiple variables must be computed and compared in order to properly assess the need for corrective action. The analysis engine described in simple form with respect to FIGS. 27 and 28 compares different pairs of parameters and provides a series of binary output values. In practice, however, more complex processing can be performed, taking into account the range of conditions and values that are seen in the patient population.

Highlighting particular measured or calculated biometric parameters and results provides useful data that can guide development of a treatment plan for the patient.

Figure 33:
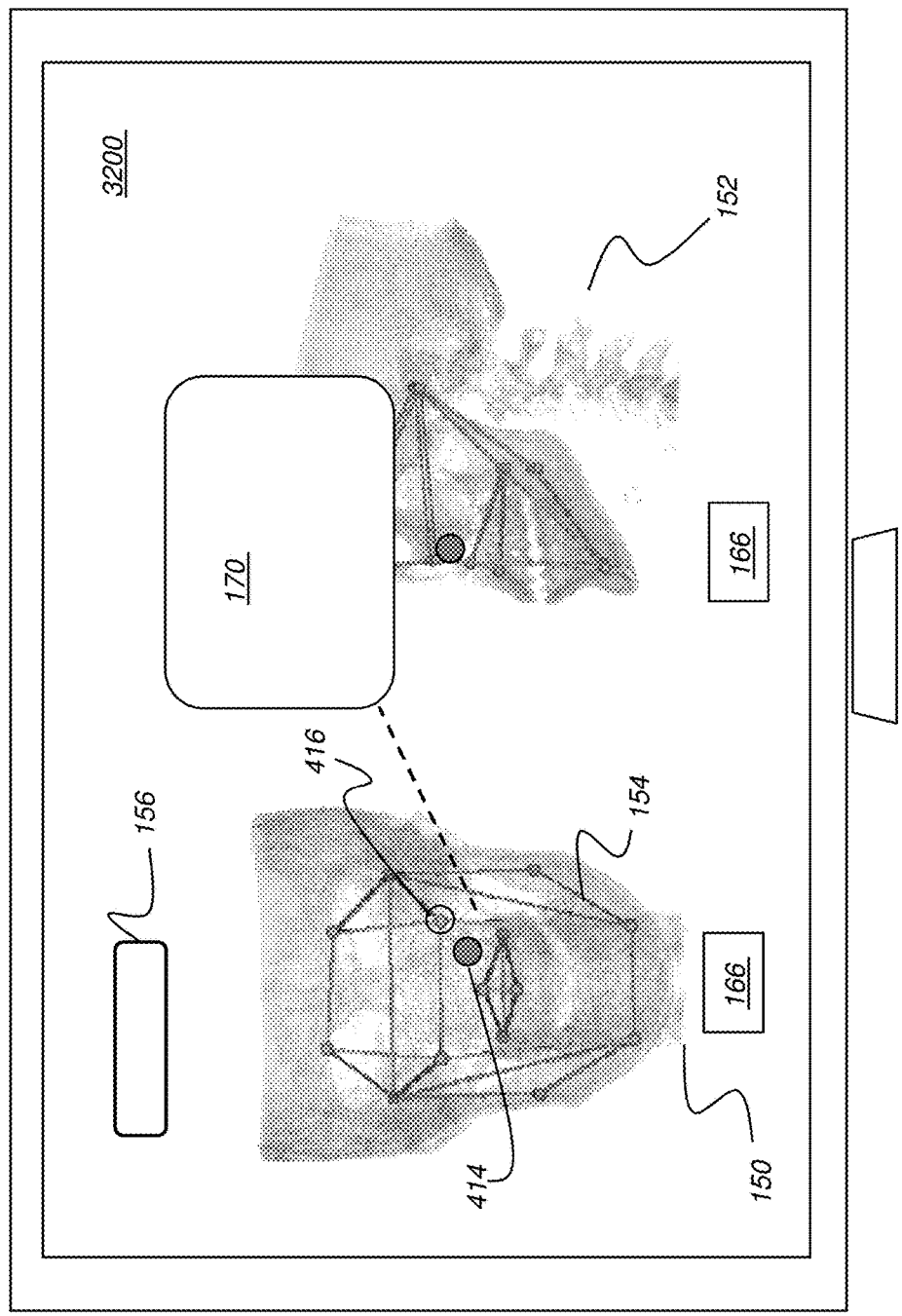
FIG. 33 shows a system display with a recommendation message based on analysis results.
Figure 34:
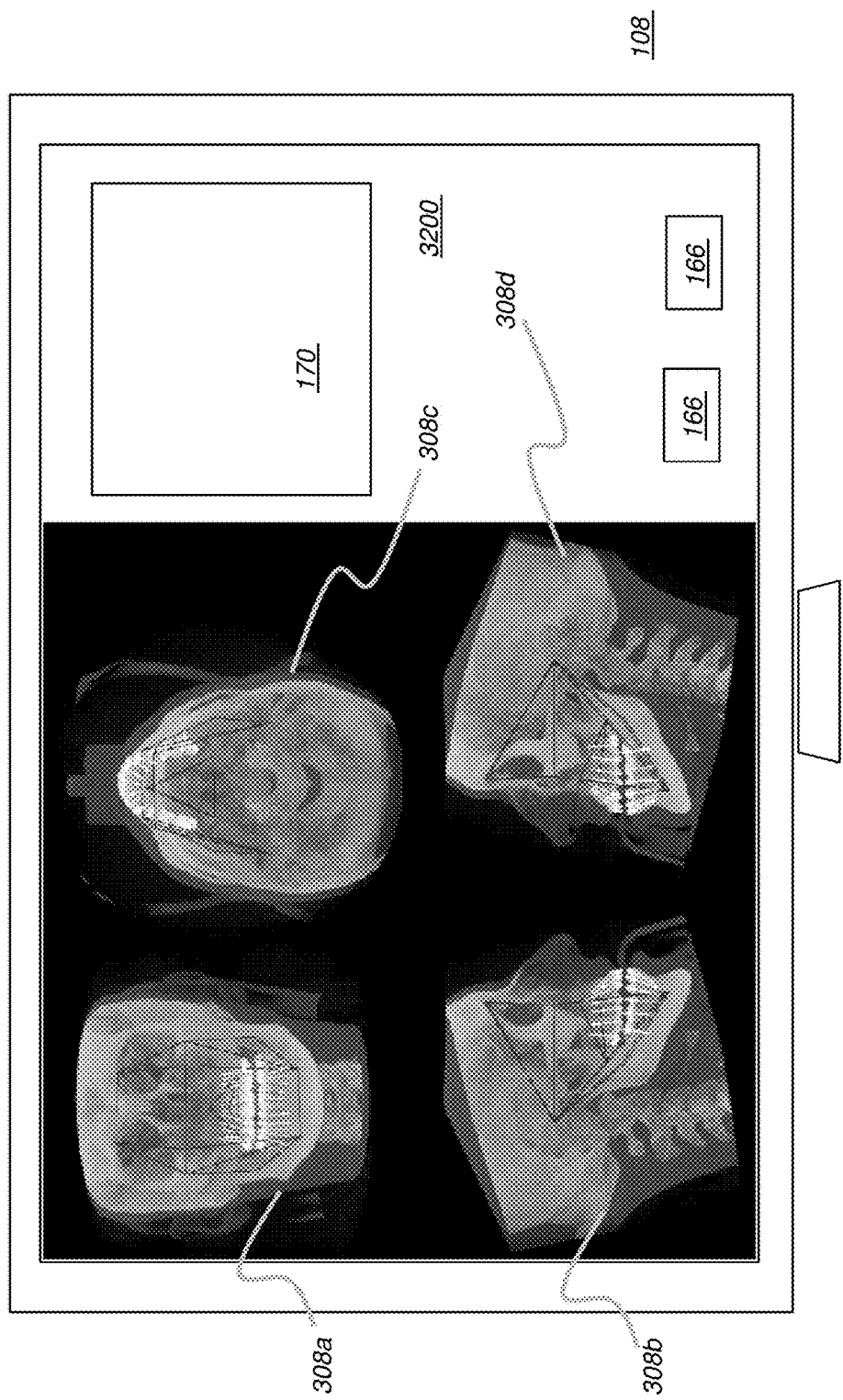
FIG. 34 shows a system display with a graphical depiction to aid analysis results.

FIG. 33 shows a system display of results 3200 with a recommendation message 170 based on analysis results and highlighting features of the patient anatomy related to the recommendation. FIG. 34 shows a system display 108 with a graphical depiction of analysis results 3200. Annotated 3-D views (e.g., 308a-308d) are shown, arranged at different angles, along with recommendation message 170 and controls 166.

Certain exemplary method and/or apparatus embodiments according to the present disclosure can address the need for objective metrics and displayed data that can be used to help evaluate asymmetric facial/dental anatomic structure. Advantageously, exemplary method and/or apparatus embodiments present measured and analyzed results displayed in multiple formats suitable for assessment by the practitioner.

FIG. 35 shows an exemplary text report for maxillofacial asymmetry assessment according to an embodiment of the present disclosure. The report lists a set of assessment tables (T1-T19) available from the system, with cell entries (denoted by C with row and column indices, C(row, column)) providing maxillofacial/dental structural asymmetry property assessment comments organized based on the calculations related to relationships between obtained parameters, such as parameters P1-P15 in FIG. 31B. An exemplary assessment table 3292 is depicted in FIG. 32E, having four rows and four columns.

In one embodiment, for each exemplary assessment table (e.g., 19 assessment tables), only one cell 3294 can be activated at a time; the activated cell content is highlighted, such as by being displayed in red font. In the exemplary table 3292, the activated cell is C(2,2) (3294) with a content "0" indicating that asymmetry is not found for the property of incisors and molars upper/lower deviations.

For a quick reference to the exemplary assessment tables, the system of the present disclosure generates a checklist type concise summary page (e.g., FIG. 35) that provides information with respect to table numbers (Tn), parameter numbers (Pk, j), cell indices (Cs, t), and actual assessment comments from assessment tables T1-T19. The information obtained from this type of text report can be helpful for the practitioner, providing at least some objective metrics that can be useful in developing a treatment plan for a particular patient or evaluating treatment progress. Further beneficial to the practitioner can be cumulative summative evaluations directed to overall condition assessments of a patient. This can be the situation, in particular, when numbers of conditional reference points and relationships therebetween utilized to determine asymmetric facial/dental anatomic structures or relationships for a patient involve large numbers of view-oriented and 3D-oriented treatment conditions, with variable underlying causes.

In one exemplary asymmetric determination table embodiment, 19 assessment tables can be included with hundreds of reference points and several hundreds of relationships therebetween. In this exemplary asymmetric determination table embodiment, tables include: T1: Asymmetric matching incisors and molars upper/lower deviations; T2: Arch rotation; T3: Upper/lower arch right rotation and upper or lower arch responsibility; T4: Asymmetric matching incisors upper/lower deviations with upper inc transverse deviation, response of upper or lower arch in the upper/lower incisors trans deviation; T5: Asymmetric matching incisors upper/lower deviations with anterior bases transverse deviation, response of upper or lower arch anterior deviation in the upper/lower incisors trans deviation; T6: Asymmetric matching incisors upper/lower molar deviations with upper molars transverse deviation, response of upper or lower molars trans deviation; T7: Asymmetric matching incisors upper/lower molar deviations with lower molars transverse deviation; T8: Asymmetric matching basic bones upper/lower deviations; T9: Asymmetric matching basic bones upper/lower anterior relations with anterior maxilla deviation; T10: Asymmetric matching basic bones upper/lower anterior relations with anterior mandible deviation; T11: Asymmetric matching incisors upper/lower deviations with anterior bases transverse deviation; T12: Vertical asymmetric comparing L/R molars altitudes difference with maxillary arch rolling; T13: Asymmetric comparing L/R molars altitudes difference with mandible arch rolling; T14: Vertical asymmetric comparing basic bones R/L posterior differences (maxillary & mandible); T15: Vertical asymmetric comparing L/R difference at mental points level (measuring maxilla-facial area and global face); T16: Anterior-posterior asymmetric comparing R/L upper/lower molars anterior-posterior difference with lower ones; T17: Anterior-posterior asymmetric comparing R/L upper/lower molars anterior-posterior relationship difference with lower ones; T18: Anterior-posterior asymmetric comparing L/R upper basis lateral landmarks anterior-posterior difference with lower ones; T19: Anterior-posterior asymmetric matching mandibular horizontal branch with R/L global hemifaces;

In such complex asymmetric facial/dental anatomic structures or relationships determinations according to this application, optional cumulative summative evaluations directed to overall condition assessments of a patient are preferably used. In some embodiments, exemplary cumulative summative or overall diagnosis comments can include: Asymmetry anterior posterior direction (AP comment or S1), Asymmetry vertical direction (VT comment or S2), and Asymmetry Transverse direction (TRANS comment or S3). Still further, highest level evaluation score(s) can be used by using one or more or combining S1, S2 and S3 to determine an Asymmetry global score (Asymmetry Global determination). For example, the exemplary Asymmetry global score can be a summary (e.g., overall class I, II, III), broken into few, limited, categories (e.g., normal, limited evaluation, detailed assessment suggested) or represented/characterized by dominant asymmetry condition (e.g., S1, S2, S3).

As shown in FIG. 35, the exemplary text report also presents S1 anterior-posterior direction "synthetic" asymmetry comment, S2 vertical direction synthetic asymmetry comment, and S3 transversal direction synthetic asymmetry comment.

The "synthetic" terminology is derived in this application to from a pair of tables in each direction. In certain exemplary embodiments, the "synthetic" terminology can be determined from a combination of a plurality of tables from each assessment type (e.g., AP, V, Trans involving or representing substantial (e.g., >50%) portions of the skull) or a pair of tables in each direction.

For example, S1 synthetic comment is derived from Table 17 and Table 19. The derivation first assigns a score to each of the cells of Table 17 and Table 19. An exemplary score assignment is explained as follows For Table 17, C(1,3)=−2; C(1,2)=C(2,3)=−1; C(2,1)=C(3,2)=1; C(3,1)=2; other cells are assigned with a value 0.

For Table 19, C(1,1)=−2; C(1,2)=C(2,1)=−1; C(2,3)=C(3,2)=1; C(3,3)=2; other cells are assigned with a value 0.

The derivation of S1 synthetic comment evaluates the combined score by adding the scores from Table 17 and Table 19.

For instance, if C(1,3) in Table 17 is activated and C(1,1) in Table 19 is activated then the combined score will be the summation of the scores of C(1,3) of Table 17 and C(1,1) of Table 19. Since C(1,3) in Table 17 is assigned with a value −2 and C(1,1) in Table 19 is assigned with a value −2, therefore, the combined the score is −4. Obviously, the possible combined sore values for S1 are −4, −3, −2, −1, 0, 1, 2, 3 and 4.

The exemplary S1 synthetic comments can be based on the combined score value are summarized below.

If the combined score=−4 or −3, the S1 synthetic comment=strong left anterior-posterior excess.

If the combined score=−2, the S1 synthetic comment=left anterior-posterior excess tendency.

If the combined score=2, the S1 synthetic comment=right anterior-posterior excess tendency.

If the combined score=4 or 3, the S1 synthetic comment=strong right anterior-posterior excess.

If the combined score=0, no comment.

Similar synthetic comment derivations are applied to the vertical direction and transversal direction.

Referring back to FIG. 35, the exemplary text report displays S1=strong right anteroposterior excess, S2=none and S3=left upper deviation tendency.

In very rare cases, synthetic comments show up in all three directions, or the comments present some type of mixture of synthetic comments, which can prompt further extended diagnosis and/or treatment.

Further, selected exemplary method and/or apparatus embodiments according to the application can also provide a quick visual assessment of the asymmetry property of the maxillofacial/dental structural of a patient.

Figure 36:
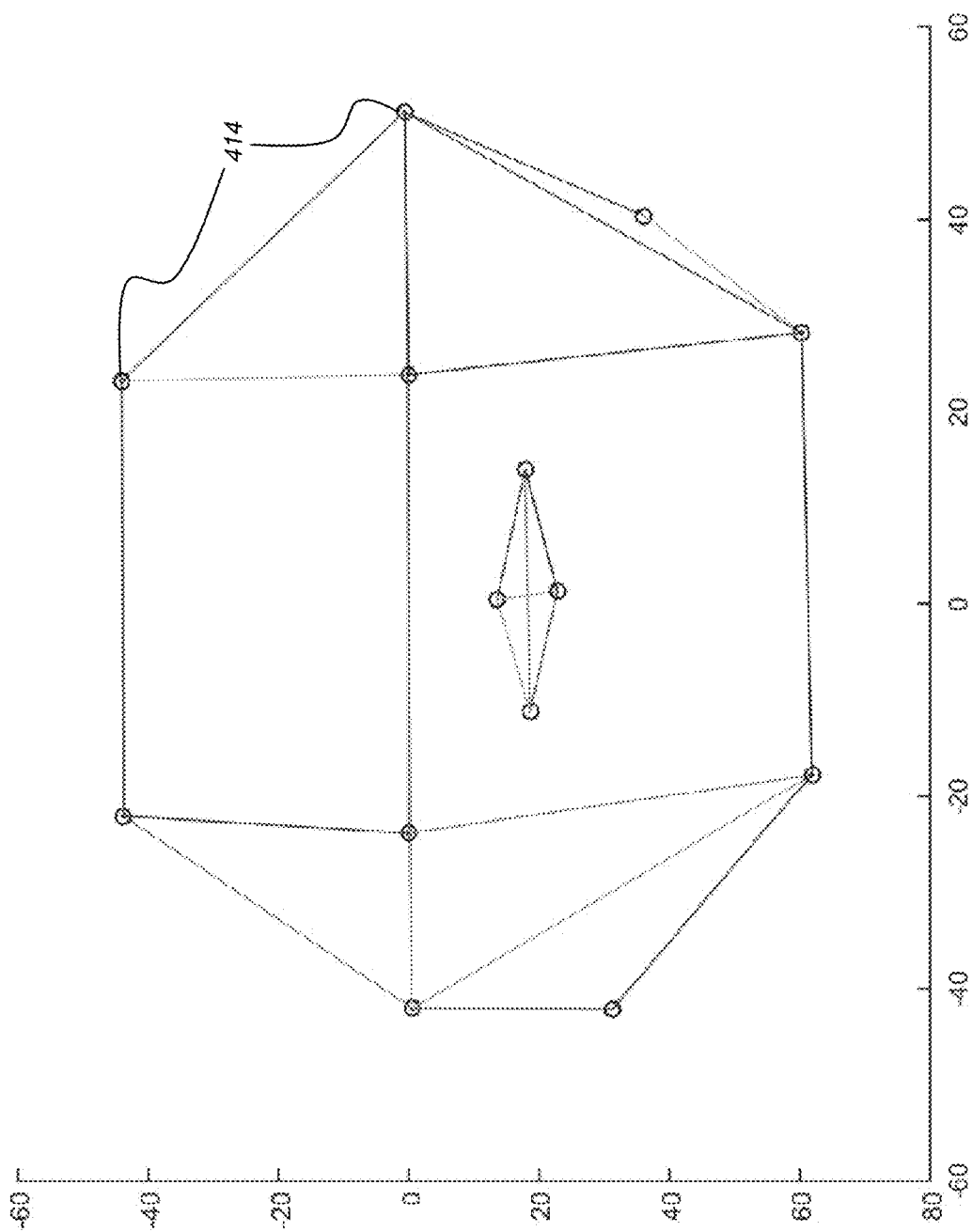
FIG. 36 is a graph that shows relative left-right asymmetry for a patient in a front view.

FIG. 36 is a plot or graph that shows the maxillofacial/dental structural features for a patient with respect to a front view, plotted using the landmarks, reference marks 414, selected by the operator (see FIG. 5). This type of displayed plot clearly shows asymmetry (left vs. right) in an objective fashion for this exemplary patient.

Figure 37:
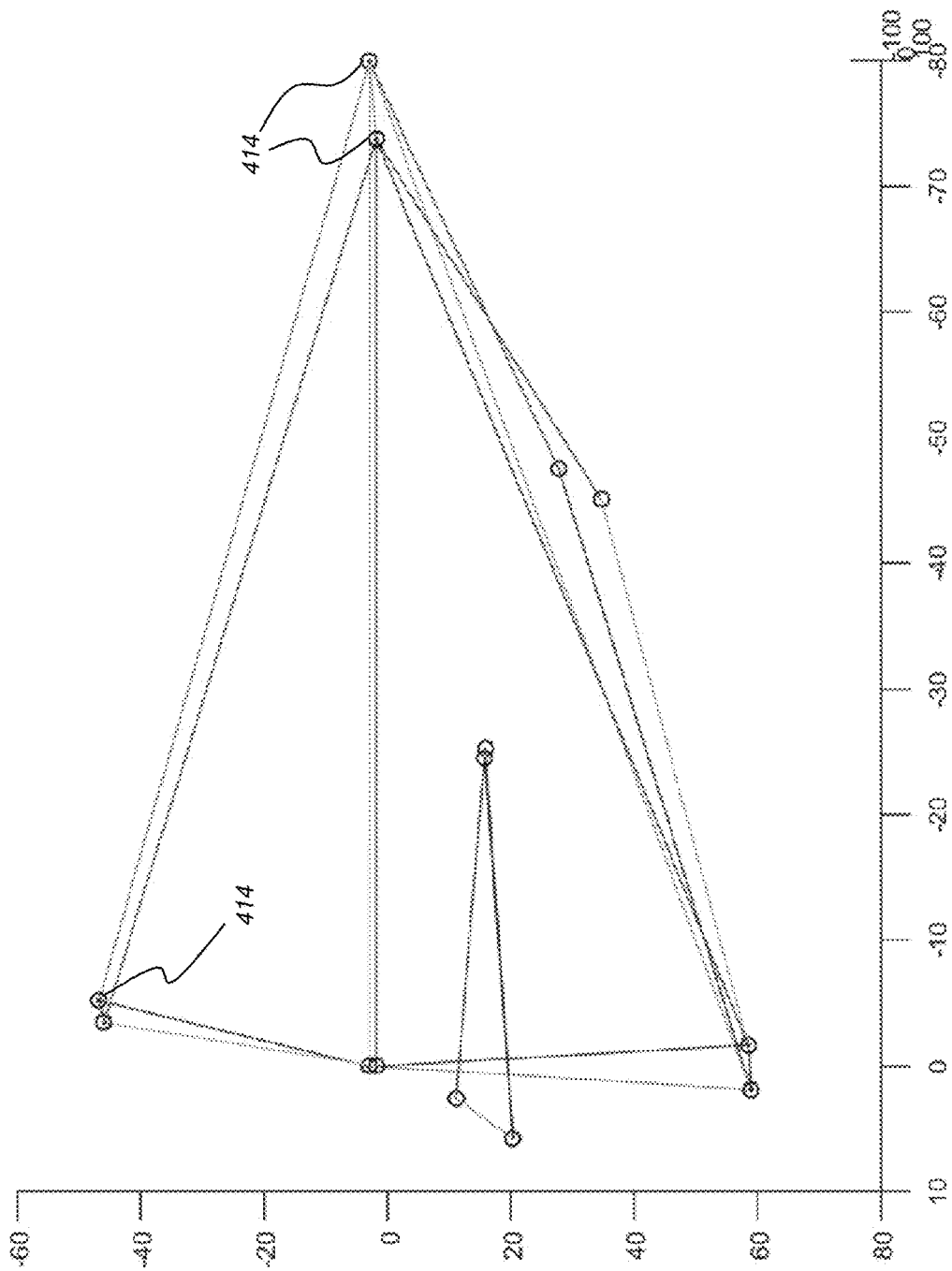
FIG. 37 is a graph showing relative overlap of left and right sides of a patient's face.

Likewise, FIG. 37 is a plot or graph of a sagittal view, with reference marks 414 showing how closely the left and right sides of a patient's face overlap, as another objective indicator of asymmetry.

Figure 38:
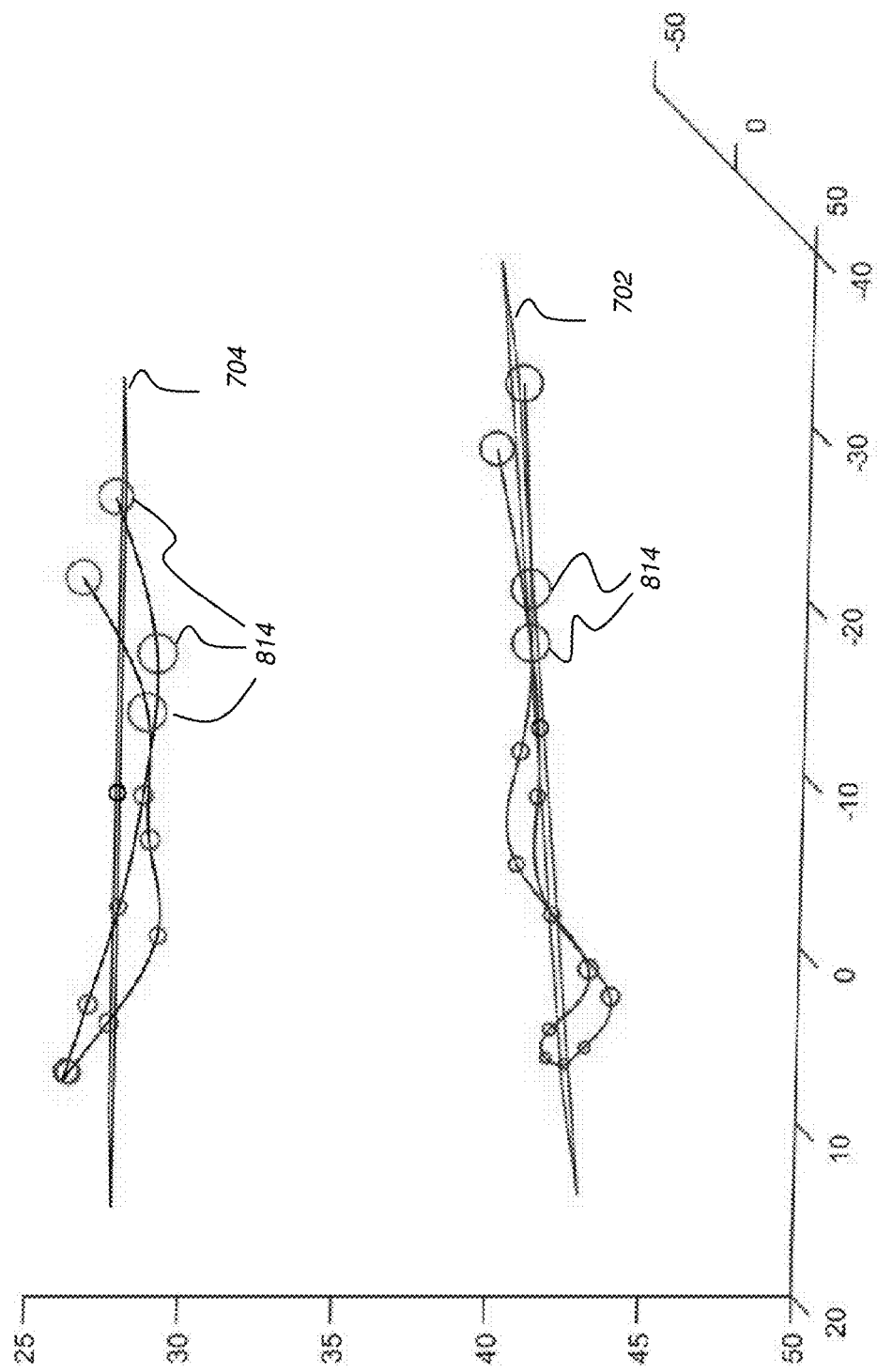
FIG. 38 is a graph showing facial divergence.

FIG. 38 is a plot or graph providing a quick visual assessment of noticeable improper alignment of the bite of a patient in a sagittal view of upper and lower jaw planes 704 and 702. Jaw plane 704 is computed based on the derived upper jaw marks 814, lower jaw plane 702 is computed based on the derived lower jaw marks 814. Derived marks 814 are computed based on the segmented teeth 304 shown in FIG. 4 and show the location of the tooth. The example shown in FIG. 38 depicts exemplary visual cues for a patient with a hyperdivergent pattern.

Described herein is a computer-executed method for 3-D cephalometric analysis of maxillofacial asymmetry for a patient. The method acquires and displays reconstructed volume image data from a computed tomographic scan of a patient's head from at least a first 2-D view. An operator instruction positions and displays at least one reference mark on the at least the first displayed 2-D view. One or more dentition elements within the mouth of the patient are then segmented. The method computes and displays cephalometric parameters for the patient according to data from the at least one reference mark and the one or more segmented dentition elements and computes, using the computed cephalometric parameters, one or more results indicative of maxillofacial asymmetry. The method then energizes a graphical or text display to show the computed results indicative of maxillofacial asymmetry.

Consistent with exemplary embodiments herein, a computer program can use stored instructions that perform 3D biometric analysis on image data that is accessed from an electronic memory. As can be appreciated by those skilled in the image processing arts, a computer program for operating the imaging system and probe and acquiring image data in exemplary embodiments of the application can be utilized by a suitable, general-purpose computer system operating as control logic processors as described herein, such as a personal computer or workstation. However, many other types of computer systems can be used to execute the computer program of the present invention, including an arrangement of networked processors, for example. The computer program for performing exemplary method embodiments may be stored in a computer readable storage medium. This medium may include, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary method embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products of the application may make use of various image manipulation algorithms and processes that are well known. Additional aspects of such algorithms and systems, and hardware and/or software for producing and otherwise processing the images or co-operating with the computer program product exemplary embodiments of the application, are not specifically shown or described herein and may be selected from such algorithms, systems, hardware, components and elements known in the art.

Certain exemplary method and/or apparatus embodiments according to the application can allow the practitioner to take advantage of objective metrics and/or displayed data to help evaluate asymmetric facial/dental anatomic structure(s). Advantageously, exemplary method and/or apparatus embodiments can provide multiple graduated or hierarchical measured and analyzed results displayed in successively higher order formats suitable for assessment by the practitioner. Although embodiments of the present disclosure are illustrated using dental imaging apparatus, similar principles can be applied for other types of diagnostic imaging and for other anatomy. Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. A method for 3-D cephalometric analysis of a patient, the method executed at least in part on a computer processor and comprising:
    displaying reconstructed volume image data from a computed tomographic scan of a patient's head from at least a first 2-D view or a 3-D view;
    accepting an operator instruction that positions and displays at least one reference mark on the at least the first displayed 2-D view or the 3-D view;
    segmenting one or more dentition elements within the mouth of the patient;
    computing and displaying a plurality of anatomical cephalometric parameters and a plurality of derived cephalometric parameters for the patient according to data from the at least one reference mark and the one or more segmented dentition elements;
    computing, using the computed cephalometric parameters, one or more results indicative of maxillofacial asymmetry; and
    energizing a graphical or text display to show the computed results indicative of maxillofacial asymmetry, where the display includes:
        a first plurality of entries representing different selected maxillofacial asymmetric anterior posterior relations, maxillofacial asymmetric vertical relations and maxillofacial asymmetric transverse relations,
        a second plurality of entries representing synthesized maxillofacial asymmetric cumulative anterior posterior condition, synthesized maxillofacial asymmetric cumulative vertical condition, and synthesized maxillofacial asymmetric cumulative transverse condition, which are generated using the first plurality of entries, and
        a third entry representing a combination of the synthesized maxillofacial asymmetric cumulative anterior posterior condition, the synthesized maxillofacial asymmetric cumulative vertical condition, and the synthesized maxillofacial asymmetric cumulative transverse condition.

2. The method of claim 1 wherein the plurality of cephalometric parameters graphically show asymmetry from a frontal view or a sagittal view.

3. The method of claim 1 further comprising comparing the computed results with previously computed results and displaying a message related to the comparison.

4. The method of claim 1 further comprising displaying one or more of the reference marks on a second 2-D view that is substantially orthogonal to the first 2-D view.

5. The method of claim 1 wherein computing and displaying a plurality of cephalometric parameters comprises generating a three-dimensional framework related to the computed cephalometric parameters.

6. The method of claim 1 where showing the computed results comprises evaluating one or more of the computed results against a value calculated from a sampling of a patient population, and where the at least one reference mark identifies an anatomical feature that is outside the mouth of the patient.

7. The method of claim 1 further comprising generating and displaying a tabular report according to calculations from the computed cephalometric parameters for each of the first plurality of entries, where said each of the first plurality of entries correspond to a one active cell of cells in the tabular report corresponding thereto.

8. The method of claim 1 further comprising displaying a graphical plot that shows the at least one reference mark and the computed results indicative of maxillofacial asymmetry.

9. The method of claim 8 where the displayed graphical plot shows computed results from a sagittal view, where the one or more results are indicative of tooth deviation.

10. A logic processor that is configured with encoded instructions for:
    displaying reconstructed volume image data from a computed tomographic scan of a patient's head from at least a first 2-D view or a 3-D view;
    segmenting one or more dentition elements within the mouth of the patient;
    computing and displaying a plurality of anatomical cephalometric parameters and a plurality of derived cephalometric parameters for the patient according to data from at least one maxillofacial reference mark and the one or more segmented dentition elements;
    computing, using the computed cephalometric parameters, one or more results indicative of maxillofacial asymmetry; and
    energizing a graphical or text display to show the computed results indicative of asymmetry, energizing a graphical or text display to show the computed results indicative of maxillofacial asymmetry, where the display includes:
        a first plurality of entries representing different selected maxillofacial asymmetric anterior posterior relations, maxillofacial asymmetric vertical relations and maxillofacial asymmetric transverse relations, and
        a second plurality of entries representing synthesized maxillofacial asymmetric cumulative anterior posterior condition, synthesized maxillofacial asymmetric cumulative vertical condition, and synthesized maxillofacial asymmetric cumulative transverse condition, which are generated using the first plurality of entries, and
        a third entry representing a combination of the synthesized maxillofacial asymmetric cumulative anterior posterior condition, the synthesized maxillofacial asymmetric cumulative vertical condition, and the synthesized maxillofacial asymmetric cumulative transverse condition.

11. The logic processor of claim 10 configured for cephalometric parameters using an analysis engine model having a plurality of networks.

* * * * *